(12) United States Patent
Atobe et al.

(10) Patent No.: US 7,960,392 B2
(45) Date of Patent: Jun. 14, 2011

(54) NITROGEN-CONTAINING HETEROCYCLIC COMPOUNDS

(75) Inventors: Masakazu Atobe, Tokyo (JP); Kenji Naganuma, Tokyo (JP); Akifumi Morimoto, Tokyo (JP); Teruki Kobayashi, Tokyo (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

(21) Appl. No.: 12/502,529

(22) Filed: Jul. 14, 2009

(65) Prior Publication Data

US 2010/0029690 A1 Feb. 4, 2010

Related U.S. Application Data

(60) Provisional application No. 61/081,501, filed on Jul. 17, 2008.

(51) Int. Cl.
C07D 401/14 (2006.01)
C07D 277/00 (2006.01)
A61K 31/4436 (2006.01)
A61K 31/427 (2006.01)

(52) U.S. Cl. ........ 514/256; 514/341; 514/370; 544/333; 546/270.7; 548/198

(58) Field of Classification Search .................. 514/256, 514/341, 370; 544/333; 546/270.7; 548/198
See application file for complete search history.

(56) References Cited

U.S. PATENT DOCUMENTS

| | | |
|---|---|---|
| 6,291,505 B1 | 9/2001 | Huebner et al. |
| 6,727,273 B2 | 4/2004 | Huebner et al. |
| RE39,708 E | 6/2007 | Huebner et al. |
| 7,446,222 B2 | 11/2008 | Bit et al. |
| 7,678,823 B2 | 3/2010 | Slade et al. |
| 2002/0111374 A1 | 8/2002 | Huebner et al. |
| 2002/0137746 A1 | 9/2002 | Carl et al. |
| 2004/0034081 A9 | 2/2004 | Huebner et al. |
| 2004/0077701 A1 | 4/2004 | Huebner et al. |
| 2005/0020646 A1 | 1/2005 | Newgreen et al. |
| 2006/0084681 A1 | 4/2006 | Parmee et al. |
| 2006/0100254 A1 | 5/2006 | Betzemeier et al. |
| 2006/0106013 A1 | 5/2006 | Breitfelder et al. |
| 2006/0235057 A1 | 10/2006 | Bit et al. |
| 2007/0072906 A1 | 3/2007 | Giblin et al. |
| 2008/0108620 A1 | 5/2008 | Brockunier et al. |
| 2008/0207708 A1 | 8/2008 | Bit et al. |
| 2008/0249135 A1 | 10/2008 | Slade et al. |
| 2008/0275053 A1 | 11/2008 | Giblin et al. |
| 2009/0156554 A1 | 6/2009 | Breitfelder et al. |
| 2010/0120749 A1 | 5/2010 | Page et al. |

FOREIGN PATENT DOCUMENTS

| | | |
|---|---|---|
| CN | 101062916 | 10/2007 |
| JP | 2002/020286 | 1/2002 |
| WO | 00/07996 A2 | 2/2000 |
| WO | 00/69465 A1 | 11/2000 |
| WO | 02/15902 A1 | 2/2002 |
| WO | 2004/033432 A1 | 4/2004 |
| WO | 2004/039753 A2 | 5/2004 |
| WO | 2004/069158 A2 | 8/2004 |
| WO | 2004/083185 A2 | 9/2004 |
| WO | 2005/010534 A1 | 2/2005 |
| WO | 2006/014618 A2 | 2/2006 |
| WO | 2006/041874 | 4/2006 |
| WO | 2007/115306 | 10/2007 |
| WO | 2008/006790 A1 | 1/2008 |
| WO | 2008/006793 A1 | 1/2008 |
| WO | 2008/006794 A1 | 1/2008 |
| WO | 2008/006795 A2 | 1/2008 |
| WO | 2008/049875 | 5/2008 |

OTHER PUBLICATIONS

Li, Ze. Design, Synthesis, and Biological Evaluation of Antiviral Agents Targeting Flavivirus Envelope Proteins. J. Med. Chem. 2008 (51) 4660-4671.*
American Urogynecologic Society. Bladder Control Problems: Prevention. Published May 2008. Accessed Dec. 30, 2010. <http://www.mypelvichealth.org/TreatmentPrevention/BladderControlProblems/Prevention/tabid/115/Default.aspx>.*
E. Ann Hallinan et al., "2,4-Disubstituted Oxazoles and Thiazoles as Latent Pharmacophores for Diacylhydrazine of SC-51089, a Potent $PGE_2$ Antagonist", Bioorganic & Medicinal Chemistry, vol. 9, pp. 1-6, 2001.
Adrian Hall et al., "Novel Methylene-Linked Heterocyclic $EP_1$ Receptor Antagonists", Bioorganic & Medicinal Chemistry Letters, vol. 18, pp. 1592-1597, 2008.
Adrian Hall et al., "Discovery of a Novel Indole Series of $EP_1$ Receptor Antagonists by Scaffold Hopping" Bioorganic & Medicinal Chemistry Letters, vol. 18 , pp. 2684-2690, 2008.

(Continued)

*Primary Examiner* — Rebecca L Anderson
*Assistant Examiner* — Samantha L Shterengarts
(74) *Attorney, Agent, or Firm* — Greenblum & Bernstein, PLC

(57) ABSTRACT

Nitrogen-containing heterocyclic compounds represented by the following Formula (1) are provided. The compounds or salts thereof have a strong EP1 antagonistic activity when they are administered to a human or an animal, and they are useful as an effective component of a pharmaceutical agent for prophylaxis and/or treatment of an overactive bladder, for example. Furthermore, they are useful as an effective component of a pharmaceutical agent for the prophylaxis and/or treatment of symptoms including frequent urination, urinary urgency and urinary incontinence.

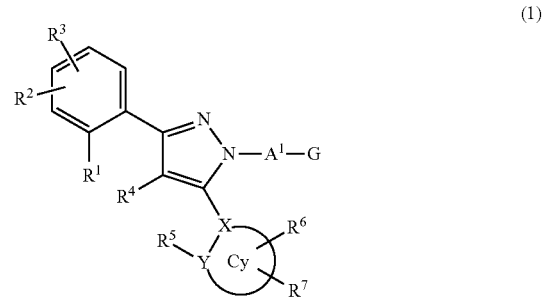

(1)

26 Claims, No Drawings

OTHER PUBLICATIONS

A. Ziganshin, "Synthesis and Purine P2X Receptor Anangonist Activity of Thiazole Derivatives" Pharmaceutical Chemistry Journal, vol. 39, No. 6, pp. 303-307, 2005.

U.S. Appl. No. 12/502,557 to Atobe et al., entitled Bicyclic Nitrogen-Containing Heterocyclic Compounds, filed Jul. 14, 2009.

U.S. Office Action (Requirement for Restriction) that issued with respect to U.S. Appl. No. 12/502,557, mailed Aug. 12, 2010.

U.S. Office Action that issued with respect to U.S. Appl. No. 12/502,557, mailed Dec. 1, 2010.

Freeman et al., Best Practice & Research Clinical Obstetrics and Gynaecology, 2005, 19, 829-841.

* cited by examiner

NITROGEN-CONTAINING HETEROCYCLIC COMPOUNDS

CROSS REFERENCE TO RELATED APPLICATIONS

This application claims the benefit of U.S. Provisional Application No. 61/081,501, filed Jul. 17, 2008.

TECHNICAL FIELD

The present invention is directed to novel compounds that have an EP1 antagonistic activity and are useful as an effective component of a pharmaceutical agent.

DESCRIPTION OF THE RELATED ART

Overactive bladder is defined by The International Continence Society as a "disorder which includes urinary urgency with or without urge incontinence, urinary frequency, and nocturia" (Non-Patent Document 1). In addition, urinary incontinence is generally defined as a "involuntary loss of urine that is objectively demonstratable and is a social or hygienic problem" and urinary urgency is generally understood as a "state at which strong and sudden desire to urinate occurs and the urge cannot be controlled." (Non-Patent Document 2).

Cause of an overactive bladder may include a change in bladder function due to aging, cerebral hemorrhage, cerebral infarction, Parkinson's disease, a neuronal disorder such as spinal injury, etc., lower urinary tract obstruction due to prostatic hypertrophy, etc. and a sensitive bladder due to expression of an irritative voiding symptom caused by hypersensitive bladder resulting from chronic cystitis, interstitial cystitis, etc. However, for most cases, the cause remains unknown.

Prostaglandin E2 (herein below, it can be sometimes abbreviated as PGE2) is one metabolite of an arachidonic acid cascade and is known to be involved with a cell protection activity, an oxytocic activity, a pain-generating activity, an activity of promoting peristaltic movement of a digestive tract, an analeptic activity, an activity of inhibiting secretion of gastric acid, an anti-hypertensive activity, a diuretic activity, etc.

It has been known that urothelium or smooth muscle of a bladder produces PGE2 and such production is increased by bladder disorder caused by various physiological irritation or inflammation, etc. (Non-Patent Documents 3 and 4). It is believed that PGE2 not only can contract smooth muscle of a bladder but also can increase voiding reflex by increasing afferent impulse as it acts on a sensory nerve of a bladder (Non-Patent Documents 5 and 6). According to recent studies, it was found that there are subtypes of PGE2 receptor which have a function different to each other. At the present moment, four subtypes including EP1, EP2, EP3 and EP4 are known (Non-Patent Documents 7 and 8). Among these, EP1 receptor is mainly present in fiber C of the sensory nerves of a bladder. It was found that, by antagonizing this receptor, voiding reflex can be inhibited (Non-Patent Document 9). It was also known that in an overactive bladder which is caused by lower urinary tract obstruction due to spinal injury, prostatic hypertrophy, etc., a hyperactivity of afferent fiber C is confirmed and this detrusor overactivity can be inhibited by inhibiting this afferent route (Non-Patent Document 10).

For example, as a compound which has an antagonistic activity for EP1 receptor, the compounds described in the following literatures have been known (Patent Documents 1 to 5).

[Non-Patent Document 1] Abrams, P. et al., Neurourol. Urodyn. 21, p. 167-178 (2002)

[Non-Patent Document 2] Yamaguchi Osamu, Clinics and Drug Therapy, 21, p.2-7 (2002)

[Non-Patent Document 3] Andersson, K E, Pharmacol. Rev. 45, 253-308 (1993)

[Non-Patent Document 4] Khan, M A. et al., Prostaglandins Leukot. Essent. Fatty Acids, 59, 415-422 (1998)

[Non-Patent Document 5] Palea, S. et al., Br. J. Pharmacol., 124p. 865-872 (1998)

[Non-Patent Document 6] Maggi, C A., Pharmacol. Res. 25, p.13-20 (1992)

[Non-Patent Document 7] Negishi, M. et al., J. Lipid Mediators Cell Signaling 12, 379-391 (1995)

[Non-Patent Document 8] Narumiya, S. et al., Physiological Rev. 79, p.1193-1226 (1999)

[Non-Patent Document 9] Ikeda, M. et al., Biomed. Res. 27, p.49-54 (2006) [Non-Patent Document 10] Yamaguchi Osamu, Folia Pharmacologica Japonica, 121, p.331-338 (2003)

[Patent Document 1] WO00/69465
[Patent Document 2] WO02/15902
[Patent Document 3] WO2004/039753
[Patent Document 4] WO2004/083185
[Patent Document 5] WO2005/010534

DISCLOSURE OF THE INVENTION

Problems to be Solved by the Invention

Object of the present invention is to provide compounds which have an antagonistic activity for EP1 receptor and are useful as an effective component of a pharmaceutical agent for prophylaxis and/or treatment of an overactive bladder, and the compounds which are useful as an effective component of a pharmaceutical agent for prophylaxis and/or treatment of symptoms including frequent urination, urinary urgency and urinary incontinence, etc.

Means for Solving the Problems

As a result of intensive study to solve the problems described above, inventors of the present invention found that the compounds represented by the following formula (1) have a significant antagonistic effect for EP1 receptor and are useful as an effective component of a pharmaceutical agent for prophylaxis and/or treatment of an overactive bladder. In addition, it was also found that they are useful as an effective component of a pharmaceutical agent for prophylaxis and/or treatment of symptoms including frequent urination, urinary urgency and urinary incontinence, etc. The present invention is completed based on these findings.

Specifically, the present invention includes the followings.

[1] Compounds represented by the formula (1) or salt thereof:

[Chemical Formula 1]

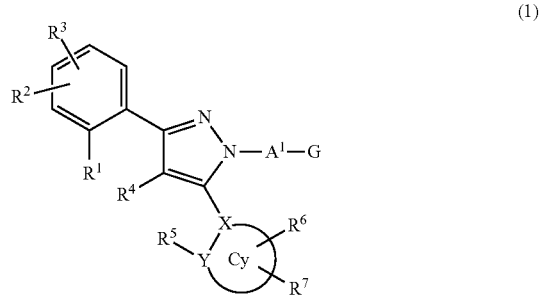

(1)

[in the formula (1), Cy represents an aryl group, a saturated cyclic hydrocarbon group or a saturated heterocyclic group, X represents a carbon atom or a nitrogen atom, Y represents a carbon atom, a nitrogen atom, an oxygen atom, or a sulfur atom, $R^1$, $R^2$ and $R^3$ can be the same or different to each other, and each independently represent a hydrogen atom, a halogen atom, an alkyl group which may be substituted, an alkenyl group which may be substituted, an alkynyl group which may be substituted, an aryl group which may be substituted, an aralkyl group which may be substituted, a hydroxy group, an alkoxy group which may be substituted, an aryloxy group which may be substituted, an alkylthio group, an acyl group, an acyloxy group, an alkylsulfinyl group, an alkylsulfonyl group, an alkyl carbamyl group, —N($R^{P1}$) ($R^{P2}$) ($R^{P1}$ and $R^{P2}$ can be the same or different to each other, and each independently represent a hydrogen atom, an alkyl group which may be substituted or an aryl group which may be substituted, or $R^{P1}$ and $R^{P2}$ together form a 3- to 7-membered ring to represent a cyclic amine of N($R^{P1}$) ($R^{P2}$).) an acylamino group, an acyl(alkyl)amino group, an alkylsulfonylamino group, an alkylsulfonyl(alkyl)amino group, a carboxy group, —CON($R^{23}$) ($R^{P4}$) ($R^{P3}$ and $R^{P4}$ can be the same or different to each other, and each independently represent a hydrogen atom, an alkyl group which may be substituted or an aryl group which may be substituted, or $R^{P3}$ and $R^{P4}$ together form a 3- to 7-membered ring to represent a cyclic amine of N($R^{P3}$) ($R^{P4}$).) or —COOR$^{P5}$ ($R^{P5}$ represents an alkyl group which may be substituted.), $R^4$ represents a hydrogen atom, a halogen atom, an alkyl group which may be substituted, an alkenyl group which may be substituted, an alkynyl group which may be substituted, a hydroxy group, an alkoxy group which may be substituted, or —N($R^{41}$) ($R^{42}$) ($R^{41}$ and $R^{42}$ can be the same or different to each other, and each independently represent a hydrogen atom, an alkyl group which may be substituted or an aryl group which may be substituted, or $R^{41}$ and $R^{42}$ together form a 3- to 7-membered ring to represent a cyclic amine of N($R^{41}$) ($R^{42}$).), $R^5$, $R^6$ and $R^7$ can be the same or different to each other, and all or part of them may be present, or none of them may be present (with the proviso that, when Y represents an oxygen atom or a sulfur atom, $R^5$ is not present.), and when $R^5$, $R^6$ and $R^7$ are present, each independently represent a hydrogen atom, a halogen atom, an alkyl group which may be substituted, an alkenyl group which may be substituted, an alkynyl group which may be substituted, an aryl group which may be substituted, an aralkyl group which may be substituted, a hydroxy group, an alkoxy group which may be substituted, an aryloxy group which may be substituted, an alkylthio group, an acyl group, an acyloxy group, an alkylsulfinyl group, an alkylsulfonyl group, an alkyl carbamyl group, —N($R^{Y1}$) ($R^{Y2}$) ($R^{Y1}$ and $R^{Y2}$ can be the same or different to each other, and each independently represent a hydrogen atom, an alkyl group which may be substituted, or an aryl group which may be substituted, or $R^{Y1}$ and $R^{Y2}$ together form a 3- to 7-membered ring to represent a cyclic amine of N($R^{Y1}$) ($R^{Y2}$).), an acylamino group, an acyl(alkyl)amino group, an alkylsulfonylamino group, an alkylsulfonyl(alkyl)amino group, a carboxy group, —CON($R^{Y3}$) ($R^{Y4}$) ($R^{Y3}$ and $R^{Y4}$ can be the same or different to each other, and each independently represent a hydrogen atom, an alkyl group which may be substituted, or an aryl group which may be substituted, or $R^{Y3}$ and $R^{Y4}$ together form a 3- to 7-membered ring to represent a cyclic amine of N($R^{Y3}$) ($R^{Y4}$).) or —COOR$^{Y5}$ ($R^{Y5}$ represents an alkyl group which may be substituted.), or, $R^1$ and $R^4$ may together represent a ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom or a nitrogen atom, or, $R^4$ and $R^5$ may together represent a ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom or a nitrogen atom, $A^1$ represents a single bond, an alkylene group which may be substituted or an alkenylene group which may be substituted, G represents any one of the following formulas ($G^1$) to ($G^4$):

[Chemical Formula 2]

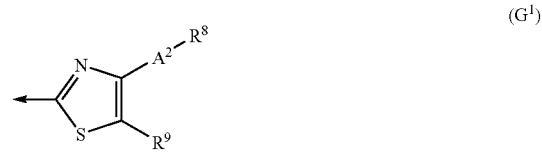
($G^1$)

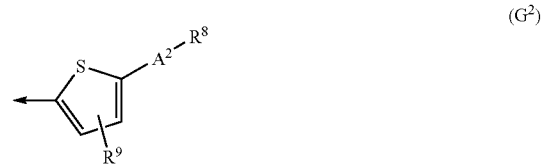
($G^2$)

($G^3$)

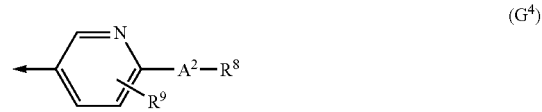
($G^4$)

{in the formulas ($G^1$) to ($G^4$), $A^2$ represents a single bond, an alkylene group, or an alkenylene group which may be substituted, $R^8$ represents a carboxy group, —CON($R^{81}$) ($R^{82}$) ($R^{81}$ and $R^{82}$ can be the same or different to each other, and each independently represent a hydrogen atom, an alkyl group which may be substituted, or an aryl group which may be substituted, or $R^{81}$ and $R^{82}$ together form a 3- to 7-membered ring to represent a cyclic amine of N($R^{81}$) ($R^{82}$ ).), —COOR$^{83}$ ($R^{83}$ represents an alkyl group which may be substituted.) or a tetrazol-5-yl group, and $R^9$ represents a hydrogen atom or an alkyl group which may be substituted}].

[2] The compounds described in the above [1] or salt thereof in which G is the formula ($G^1$).

[2-2] The compounds described in the above [1] or salt thereof in which G is the formula (G 2).

[2-3] The compounds described in the above [1] or salt thereof in which G is the formula ($G^3$)

[2-4] The compounds described in the above [1] or salt thereof in which G is the formula ($G^4$).

[3] The compounds described in any one of the above [1] to [2-4] or salt thereof in which $R^8$ is a carboxy group.

In addition, when the item numbers, that are referred to like [1] to [2-4] in the above, are described with a range and there is an additional item having branch number like [2-2], etc., an item having branch number like [2-2], etc. is also referred to, and it has the same meaning for the following descriptions.

[4] The compounds described in any one of the above [1] to [3] or salt thereof in which $A^2$ is a single bond, an alkylene group having two or less carbon atoms which may be substituted with a lower alkyl group or an ethenylene group which may be substituted with a lower alkyl group.

[4-2] The compounds described in any one of the above [1] to [3] or salt thereof in which $A^2$ is a single bond.

[4-3] The compounds described in any one of the above [1] to [3] or salt thereof in which $A^2$ is an ethenylene group which may be substituted with a lower alkyl group.

[5] The compounds described in any one of the above [1] to [4-3] or salt thereof in which $A^1$ is a single bond, an alkylene group, or an alkenylene group.

[5-2] The compounds described in any one of the above [1] to [4-3] or salt thereof in which $A^1$ is a single bond, a methylene group which may be substituted with a lower alkyl group, or an ethenylenyl group which may be substituted with a lower alkyl group.

[6] The compounds described in any one of the above [1] to [4-3] or salt thereof in which $A^1$ is a single bond.

[7] The compounds described in any one of the above [1] to [4-3] or salt thereof in which $A^1$ is a methylene group which may be substituted with a lower alkyl group.

[7-2] The compounds described in any one of the above [1] to [4-3] or salt thereof in which $A^1$ is a ethenylene group which may be substituted with a lower alkyl group.

[8] The compounds described in any one of the above [1] to [7-2] or salt thereof in which Cy is an aryl group.

[9] The compounds described in any one of the above [1] to [7-2] or salt thereof in which Cy is a phenyl group.

[10] The compounds described in any one of the above [1] to [7-2] or salt thereof in which Cy is a saturated heterocyclic group.

[10-2] The compounds described in any one of the above [1] to [7-2] or salt thereof in which Cy is a saturated cyclic hydrocarbon group.

[10-3] The compounds described in any one of the above [1] to [7-2] or salt thereof in which Cy is a partially unsaturated cyclic carbon group or heterocyclic group.

[10-4] The compounds described in any one of the above [1] to [7-2] or salt thereof in which Cy is a partially unsaturated cyclic carbon group.

[10-5] The compounds described in any one of the above [1] to [7-2] or salt thereof in which Cy is a partially unsaturated heterocyclic group.

[10-6] The compounds described in any one of the above [1] to [7-2] or salt thereof in which Cy is a thienyl group or a furyl group.

[11] The compounds described in any one of the above [1] to [10-6] or salt thereof in which $R^4$ is a halogen atom, an alkyl group which may be substituted, a hydroxy group or an amino group.

[11-2] The compounds described in any one of the above [1] to [10-6] or salt thereof in which $R^4$ is an alkyl group which may be substituted.

[11-3] The compounds described in any one of the above [1] to [10-6] or salt thereof in which $R^4$ is an amino group.

[12] The compounds described in any one of the above [1] to [11-3] or salt thereof in which $R^1$, $R^2$ and $R^3$ are a group which is independently selected from a group consisting of a hydrogen atom, a halogen atom, an alkyl group which may be substituted, a hydroxy group and an alkoxy group which may be substituted.

[12-2] The compounds described in any one of the above [1] to [11-3] or salt thereof in which $R^1$, $R^2$ and $R^3$ are a group which is independently selected from a group consisting of a hydrogen atom and a hydroxy group.

[12-3] The compounds described in any one of the above [1] to [11-3] or salt thereof in which $R^1$, $R^2$ and $R^3$ are a hydrogen atom.

[13] The compounds described in any one of the above [1] to [12-3] or salt thereof in which $R^5$, $R^6$ and $R^7$ are a group which is independently selected from a group consisting of a hydrogen atom, a halogen atom, an alkyl group which may be substituted, a hydroxy group and an alkoxy group which may be substituted.

[14] The compounds described in any one of the above [1] to [12-3] or salt thereof in which $R^5$, $R^6$ and $R^7$ are a group which is independently selected from a group consisting of a hydrogen atom, a halogen atom, an alkyl group which may be substituted and an alkoxy group which may be substituted.

[15] The compounds described in any one of the above [1] to [10-6], [13] or [14] or salt thereof in which $R^1$ and $R^4$ together represent a ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom or a nitrogen atom.

[15-2] The compounds described in any one of the above [1] to [10-6], [13] or [14] or salt thereof in which $R^1$ and $R^4$ together represent a 5- or 6-membered ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom or a nitrogen atom.

[15-3] The compounds described in any one of the above [1] to [10-6], [13] or [14] or salt thereof in which $R^1$ and $R^4$ together represent a 6-membered ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom or a nitrogen atom.

[15-4] The compounds described in any one of the above [1] to [10-6], [13] or [14] or salt thereof in which $R^1$ and $R^4$ together represent a 6-membered ring which is selected from a group consisting of a partially unsaturated hydrocarbon ring which may be substituted and an unsaturated hydrocarbon ring which may be substituted.

[16] The compounds described in any one of the above [1] to [10-6] or [12] to [12-3] or salt thereof in which $R^4$ and $R^5$ together represent a ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom or a nitrogen atom.

[16-2] The compounds described in any one of the above [1] to [10-6] or [12] to [12-3] or salt thereof in which $R^4$ and $R^5$ together represent a 5- or 6-membered ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom or a nitrogen atom.

[16-3] The compounds described in any one of the above [1] to [10-6] or [12] to [12-3] or salt thereof in which $R^4$ and $R^5$ together represent a 5-membered ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom or a nitrogen atom.

[16-4] The compounds described in any one of the above [1] to [10-6] or [12] to [12-3] or salt thereof in which $R^4$ and $R^5$ together represent a 5-membered ring which is selected from a group consisting of a partially unsaturated hydrocarbon ring which may be substituted and an unsaturated hydrocarbon ring which may be substituted.

[16-5] The compounds described in the above [1] or salt thereof in which

G is the Formula ($G^1$),
$A^1$ and $A^2$ are a single bond,
$R^1$ represents a hydrogen atom or a partially unsaturated ring together with $R^4$,
$R^4$ is a methyl group, an amino group, a hydroxy group, a fluorine atom, a chlorine atom, or a bromine atom when $R^1$ is a hydrogen atom,
$R^2$, $R^3$ and $R^5$ are a hydrogen atom,
Cy is benzene, thiophene, furan, cyclohexene, or 3,4-dihydro-2H-pyran,
X and Y are a carbon atom,
$R^6$ and $R^7$ each independently represent a hydrogen atom or a fluorine atom,
$R^8$ is a carboxy group, and
$R^9$ is a hydrogen atom.

[16-6] The compounds described in the above [1] or salt thereof in which

G is the Formula ($G^1$),
$A^1$ and $A^2$ are a single bond,
$R^1$, $R^2$, $R^3$ and $R^5$ are a hydrogen atom,
$R^4$ is a methyl group, an amino group, a hydroxy group, a fluorine atom, a chlorine atom, or a bromine atom,
Cy is benzene, thiophene, furan, cyclohexene, or 3,4-dihydro-2H-pyran,
X and Y are a carbon atom, $R^6$ and $R^7$ each independently represent a hydrogen atom or a fluorine atom, $R^8$ is a carboxy group, and
$R^9$ is a hydrogen atom.

[16-7] The compounds described in the above [1] or salt thereof in which

G is the Formula ($G^1$),
$A^1$ and $A^2$ are a single bond,
$R^1$ represents a partially unsaturated ring together with $R^4$,
$R^2$, $R^3$ and $R^5$ are a hydrogen atom,
Cy is benzene, thiophene, furan, cyclohexene, or 3,4-dihydro-2H-pyran,
X and Y are a carbon atom,
$R^6$ and $R^7$ each independently represent a hydrogen atom or a fluorine atom,
$R^8$ is a carboxy group, and
$R^9$ is a hydrogen atom.

[17] A pharmaceutical agent which includes as an effective component the compounds described in any one of the above [1] to [16-7] or pharmaceutically acceptable salt thereof.

[17-2] A prodrug of the compounds described in any one of the above [1] to [16-7] or pharmaceutically acceptable salt thereof.

[18] The pharmaceutical agent that is described above [17], which is used for prophylaxis and/or treatment of an overactive bladder.

[18-2] The pharmaceutical agent that is described above [17], which is used for prophylaxis and/or treatment of symptoms including frequent urination, urinary urgency and urinary incontinence.

[19] An EP1 antagonist which includes as an effective component the compounds described in any one of the above [1] to [16-7] or pharmaceutically acceptable salt thereof.

[20] Use of the compounds described in any one of the above [1] to [16-7] or pharmaceutically acceptable salt thereof for the preparation of a pharmaceutical agent which is used for prophylaxis and/or treatment of an overactive bladder, or a prodrug thereof.

[20-2] Use of the compounds described in any one of the above [1] to [16-7] or pharmaceutically acceptable salt thereof for the preparation of a pharmaceutical agent which is used for prophylaxis and/or treatment of symptoms including frequent urination, urinary urgency and urinary incontinence.

[21] A method for the prophylaxis and/or treatment of an overactive bladder in mammal, including administering to the mammal the compounds described in any one of the above [1] to [16-7] or pharmaceutically acceptable salt thereof in an amount which is effective for the prophylaxis and/or treatment of an overactive bladder.

[21-2] A method for the prophylaxis and/or treatment of frequent urination, urinary urgency or urinary incontinence in mammal, including administering to the mammal the compounds described in any one of the above [1] to [16-7] or pharmaceutically acceptable salt thereof in an amount which is effective for the prophylaxis and/or treatment of the symptoms.

EFFECT OF THE INVENTION

The "compounds represented by the formula (1) or salt thereof" (herein below, they can be sometimes abbreviated as the "compounds of the present invention") have a potent antagonistic activity for EP1 receptor when they are administered to a human or an animal, and they are useful as an effective component of a pharmaceutical agent for the prophylaxis and/or treatment of an overactive bladder, for example. Furthermore, they are useful as an effective component of a pharmaceutical agent for the prophylaxis and/or treatment of symptoms including frequent urination, urinary urgency and urinary incontinence.

BEST MODE TO CARRY OUT THE INVENTION

Herein below, the present invention will be explained in greater detail.

In the present specification, a fluorine atom, a chlorine atom, a bromine atom or an iodine atom is exemplified as a halogen atom.

As for the "lower" substituent described in the present specification, a substituent having at most ten carbon atoms which constitute the substituent can be mentioned. Specifically, substituents having 1 to 6 carbon atoms can be mentioned. Substituents having 1 to 3 carbon atoms can be mentioned as a preferred example.

Examples of an alkyl group described in the present specification include a linear, branched, or cyclic saturated hydrocarbon group, or a combination thereof. A lower alkyl group is preferred. Preferred examples thereof include an alkyl group having 1 to 6 carbon atoms, and more preferred examples thereof include an alkyl group having 1 to 3 carbon atoms. Preferred examples of an alkyl group having 1 to 3 carbon atoms include a methyl group, an ethyl group, an n-propyl group, an isopropyl group, a cyclopropyl group and the like. In addition, preferred examples of an alkyl group having 4 to 6 carbon atoms include an n-butyl group, an isobutyl group, a s-butyl group, a t-butyl group, a cyclobutyl group, a cyclopropylmethyl group, an n-pentyl group, a cyclopentyl group, a cyclopropylethyl group, a cyclobutylmethyl group, an n-hexyl group, a cyclohexyl group, a cyclopropylpropyl group, a cyclobutylethyl group, a cyclopentylmethyl group and the like. As an alkyl group, a methyl group, an ethyl group, an n-propyl group, or an isopropyl group is more preferred.

Examples of an alkenyl group described in the present specification include a lower alkenyl group which has one or at least two double bonds. A lower alkenyl group including one double bond is preferred. An alkenyl group having 2 to 5 carbon atoms is preferred as a lower alkenyl group. An alkenyl group having 2 to 4 carbon atoms is more preferred. Preferred examples of an alkenyl group having 2 to 4 carbon atoms include a vinyl group, an allyl group, a propenyl group, a butylidene group, a but-1-enyl group, a but-2-enyl group, a but-3-enyl group and the like. In addition, preferred examples of an alkenyl group having 5 carbon atoms include a pentylidene group, a pent-1-enyl group, a pent-2-enyl group, a pent-3-enyl group, a pent-4-enyl group and the like. More preferred examples of an alkenyl group include a vinyl group, an allyl group, or a propenyl group.

Examples of an alkynyl group of the present specification include a lower alkynyl group which has one or at least two triple bonds. A lower alkynyl group including one triple bond is preferred. The alkynyl group including 2 to 5 carbon atoms is preferred as a lower alkynyl group. Specifically, preferred examples include an ethynyl group, a prop-1-ynyl group, a prop-2-ynyl group, a but-1-ynyl group, a but-2-ynyl group, a but-3-ynyl group, a pent-1-ynyl group, a pent-2-ynyl group, a pent-3-ynyl group, a pent-4-ynyl group and the like. An ethynyl group, a prop-2-ynyl group, or a but-3-ynyl group is more preferred.

As for the alkylene group of the present specification, a divalent residue which is formed by removal of any single hydrogen atom from the alkyl group described above can be exemplified and it includes a linear, branched, or cyclic saturated divalent hydrocarbon group, or a combination thereof. A lower alkylene group is preferred. As for the lower alkylene group, an alkylene group having 1 to 6 carbon atoms is preferred. An alkylene group having 1 to 3 carbon atoms is more preferred. Preferred examples of an alkylene group having 1 to 3 carbon atoms include a methylene group, an ethylene group, an n-propylene group, an isopropylene group or a cyclopropylene group. In addition, preferred examples of an alkylene group having 4 to 6 carbon atoms include a divalent residue which is formed by removal of any single hydrogen atom from the group which is described above as a preferred example of the alkyl group having 4 to 6 carbon atoms. As an alkylene group, a methylene group, an ethylene group, an n-propylene group or an isopropylene group is more preferred. A methylene group can be mentioned as a still more preferred example of an alkylene group. There is other embodiment in which an ethylene group is still more preferred example of an alkylene group.

As for an alkenylene group of the present specification, a divalent residue which is formed by removal of any single hydrogen atom from the alkenyl group described above can be exemplified and it includes a lower alkenylene group including one or at least two double bonds. A lower alkenylene group including one double bond is preferred. An alkenylene group having 2 to 5 carbon atoms is preferred as a lower alkenylene group. An alkenylene group having 2 to 4 carbon atoms is more preferred. Preferred examples of an alkenylene group having 2 to 4 carbon atoms include a vinylene group, a propenylene group, a but-1-enylene group, a but-2-enylene group, a but-3-enylene group and the like. As for an alkenylene group having 5 carbon atoms, a divalent residue which is formed by removal of any single hydrogen atom from the group which is described above as a preferred example of the alkenyl group having 5 carbon atoms can be mentioned. As an alkenylene group, a vinylene group or a propenylene group is more preferred. A vinylene group is still more preferred.

With respect to stereochemistry relating to a double bond, any of cis and trans is acceptable. Preferred stereochemistry includes trans.

As for an alkoxy group of the present specification, a linear, branched, cyclic saturated alkyl ether group, or a saturated alkyl ether group having combination thereof can be mentioned. A lower alkoxy group is preferred. As a lower alkoxy group, an alkoxy group including 1 to 6 carbon atoms is preferred. An alkoxy group including 1 to 4 carbon atoms is more preferred. Preferred examples of an alkoxy group including 1 to 4 carbon atoms include a methoxy group, an ethoxy group, an n-propoxy group, an isopropoxy group, a cyclopropoxy group, an n-butoxy group, an isobutoxy group, a s-butoxy group, a t-butoxy group, a cyclobutoxy group, a cyclopropylmethoxy group and the like. In addition, preferred examples of an alkoxy group including 5 or 6 carbon atoms include an n-pentyloxy group, a cyclopentyloxy group, a cyclopropylethyloxy group, a cyclobutylmethyloxy group, an n-hexyloxy group, a cyclohexyloxy group, a cyclopropylpropyloxy group, a cyclobutylethyloxy group, a cyclopentylmethyloxy group and the like.

As for the aryl ring of the present specification, a monocyclic aromatic ring, a fused polycyclic aromatic ring and the like can be mentioned. The monocyclic aromatic ring or the fused polycyclic aromatic ring defined herein includes a partially unsaturated monocyclic ring or a fused bicyclic carbon ring or a heterocyclic ring. The aryl ring can be a hydrocarbon ring or, as a ring-constituting atom other than a carbon atom, it may include at least one, for example 1 to 3, of one or at least two kinds of heteroatoms selected from a group consisting of a nitrogen atom, a sulfur atom and an oxygen atom.

Examples of a monocyclic aromatic ring include a monocyclic aromatic hydrocarbon or a monocyclic aromatic heterocycle which includes one or at least two heteroatoms. As a monocyclic aromatic hydrocarbon, a benzene ring, a cyclopentene ring or a cyclohexene ring can be mentioned as a preferred example. As a monocyclic aromatic heterocycle, a 5- or 6-membered aromatic heterocycle which includes one or at least two heteroatoms can be mentioned. Specific examples of the preferred 5- or 6-membered aromatic heterocycle include thiophene, pyridine, furan, thiazole, oxazole, pyrazole, pyrazine, pyrimidine, pyrrole, imidazole, pyridazine, isothiazole, isoxazole, 1,2,4-oxadiazole, 1,3,4-oxadiazole, 1,2,4-thiadiazole, 1,3,4-thiadiazole, furazane, 2,3-dihydrofuran, 3,4-dihydro-2H-pyran and the like.

Further, as a partially unsaturated monocycle which is included in the monocyclic aromatic ring, a partially unsaturated monocyclic carbon ring, or a monocyclic hetero ring can be mentioned. Specific example of a partially unsaturated monocyclic carbon ring include a cyclopentene ring, a cyclopenta-1,3-diene ring, a cyclohexene ring and a cyclohexa-1,3-diene ring.

Further, as a partially unsaturated monocyclic hetero ring, specific examples include a 2,3-dihydrofuran ring, a 2,5-dihydrofuran ring, a 2,3-dihydrothiophene ring, a 3,4-dihydro-2H-pyrane ring, a 3,6-dihydro-2H-pyrane ring and a 3,4-dihydro-2H-thiopyrane ring.

Examples of a fused polycyclic aromatic ring include a fused polycyclic aromatic hydrocarbon or a fused polycyclic aromatic heterocycle which includes one or at least two heteroatoms. As a fused polycyclic aromatic hydrocarbon, a fused polycyclic aromatic hydrocarbon including 9 to 14 carbon atoms, i.e., bi-or tri-cyclic aromatic hydrocarbon can be mentioned. Specifically, preferred examples include naphthalene, indene, fluorene, anthracene and the like. As a fused polycyclic aromatic heterocycle, a 9-to 14-membered, preferably 9-or 10-membered, fused polycyclic aromatic heterocycle including at least one heteroatom, for example one to four heteroatoms, can be mentioned. Specifically, preferred examples include benzofuran, benzothiophene, benzimidazole, benzoxazole, benzothiazole, benzisothiazole, naphtho[2,3-b]thiophene, quinoline, isoquinoline, indole, quinoxaline, phenanthridine, phenothiazine, phenoxazine, phthalazine, naphthyridine, quinazoline, cinnoline, carbazole, β-carboline, acridine, phenazine, phthalimide, thioxanthen and the like.

As for an aryl group of the present specification, a monocyclic aromatic group, a fused polycyclic aromatic group and the like can be mentioned, for example. In addition, a monovalent residue that is produced by removing any single hydrogen atom from the above described aryl ring can be exemplified. Further, the monocyclic aromatic group includes a partially unsaturated monocyclic group, a fused bicyclic hydrocarbon group or heterocyclic group.

As for a monocyclic aromatic group, a monovalent residue that is produced by removing any single hydrogen atom from a monocyclic aromatic ring can be exemplified. More specific and preferred examples of a monocyclic aromatic group include a phenyl group, a cyclopentenyl group (1-, 3- or 4-cyclopentenyl group), a cyclohexenyl group (1-, 3- or 4-cyclohexenyl group), a thienyl group (2- or 3-thienyl group), a pyridyl group (2-, 3- or 4-pyridyl group), a furyl group (2- or 3-furyl group), a thiazolyl group (2-, 4- or 5-thiazolyl group), an oxazolyl group (2-, 4- or 5-oxazolyl group), a pyrazolyl group (1-, 3- or 4-pyrazolyl group), a 2-pyrazinyl group, a pyrimidinyl group (2-, 4- or 5-pyrimidinyl group), a pyrrolyl group (1-, 2- or 3- pyrrolyl group), an imidazolyl group (1-, 2- or 4-imidazolyl group), a pyridazinyl group (3- or 4-pyridazinyl group), a 3-isothiazolyl group, a 3-isoxazolyl group, a 1,2,4-oxadiazol-5-yl group, a 1,2,4-oxadiazol -3-yl group, a 2,3-dihydrofuran-2-yl group, a 2,3-dihydrofuran-3-yl group, a 2,3-dihydrofuran-4-yl group, a 2,3-dihydrofuran-5-yl group, a 2,5-dihydrofuran-2-yl group, a 2,5-dihydrofuran-3-yl group, a 2,3-dihydrothiophen-5-yl group, a 3,4-dihydro-2H-pyran-2-yl group, a 3,4-dihydro-2H-pyran-3-yl group, a 3,4-dihydro-2H-pyran-4-yl group, a 3,4-dihydro-2H-pyran-5-yl group, a 3,4-dihydro-2H-pyran-6-yl group, a 3,6-dihydro-2H-pyran-2-yl group, a 3,6-dihydro-2H-pyran-3-yl group, a 3,6-dihydro-2H-pyran-4-yl group, a 3,6-dihydro-2H-pyran-5-yl group, a 3,6-dihydro-2H-pyran-6-yl group, a 3,4-dihydro-2H-thiopyran-6-yl group and the like.

As for a fused polycyclic aromatic group, a monovalent residue that is produced by removing any single hydrogen atom from a fused polycyclic aromatic group including 2 to 4, preferably 2 or 3, rings can be exemplified.

Specifically, preferred examples of a fused polycyclic aromatic group include a 1-naphthyl group, a 2-naphthyl group, a 2-indenyl group, a 2-anthryl group, a quinolyl group (2-, 3-, 4-, 5-, 6-, 7- or 8-quinolyl group), an isoquinolyl group (1-, 3-, 4-, 5-, 6-, 7- or 8-isoquinolyl group), an indolyl group (1-, 2-, 3-, 4-, 5-, 6- or 7-indolyl group), an isoindolyl group (1-, 2-, 4- or 5-isoindolyl group), a phthalazinyl group (1-, 5- or 6-phthalazinyl group), a quinoxalinyl group (2-, 3- or 5-quinoxalinyl group), a benzofuranyl group (2-, 3-, 4-, 5- or 6-benzofuranyl group), a benzothiazolyl group (2-, 4-, 5- or 6-benzothiazolyl group), a benzimidazolyl group (1-, 2-, 4-, 5- or 6-benzimidazolyl group), a 2,1,3-benzoxadiazol-4-yl group, a 2,1,3-benzoxadiazol-5-yl group, a 2,1,3-benzoxadiazol-6-yl group, a fluorenyl group (1-, 2-, 3- or 4-fluorenyl group), a thioxanthenyl group and the like.

As for a partially unsaturated monocyclic group, a monovalent residue that is produced by removing any single hydrogen atom from the partially unsaturated monocycle can be exemplified, and it includes a partially unsaturated monocyclic carbon ring group or a monocyclic heterocyclic group. Specific examples a partially unsaturated monocyclic carbon ring group include a cyclopentenyl group (1-, 3- or 4-cyclopentenyl group), a cyclopenta-1,3-dienyl group (1-cyclopenta-1,3-dienyl group, a 2-cyclopenta-1,3-dienyl group or 5-cyclopenta-1,3-dienyl group), a cyclohexenyl group (1-, 3- or 4-cyclohexenyl group) or a cyclohexa-1,3-dienyl group (1-cyclohexa-1,3-dienyl group, a 2-cyclohexa-1,3-dienyl group and a 5-cyclohexa-1,3-dienyl group). A 1-cyclopentenyl group or 1-cyclohexenyl group is preferred. A 1-cyclohexenyl group is more preferred.

Further, specific examples of a partially unsaturated monocyclic hetero ring group include a 2,3-dihydrofuran-2-yl group, a 2,3-dihydrofuran-3-yl group, a 2,3-dihydrofuran-4-yl group, a 2,3-dihydrofuran-5-yl group, a 2,5-dihydrofuran-2-yl group, a 2,5-dihydrofuran-3-yl group, a 2,3-dihydrothiophen-5-yl group, a 3,4-dihydro-2H-pyran-2-yl group, a 3,4-dihydro-2H-pyran-3-yl group, a 3,4-dihydro-2H-pyran-4-yl group, a 3,4-dihydro-2H-pyran-5-yl group, a 3,4-dihydro-2H-pyran-6-yl group, a 3,6-dihydro-2H-pyran-2-yl group, a 3,6-dihydro-2H-pyran-3-yl group, a 3,6-dihydro-2H-pyran-4-yl group, a 3,6-dihydro-2H-pyran-5-yl group, a 3,6-dihydro-2H-pyran-6-yl group and a 3,4-dihydro-2H-thiopyran-6-yl group. A 2,3-dihydrofuran-5-yl group or 3,4-dihydro-2H-pyran-6-yl group is preferred. A 3,4-dihydro-2H-pyran-6-yl group is more preferred.

As for the saturated cyclic hydrocarbon of the present specification, a fully saturated monocyclic ring structure can be mentioned, for example. The ring consists only of a carbon atom and a 5- or 6-membered ring is more preferred. Specific examples include cyclopentane and cyclohexane.

As for the saturated cyclic hydrocarbon group of the present specification, a monovalent residue that is produced by removing any single hydrogen atom from the saturated cyclic hydrocarbon group described above can be mentioned, for example.

Examples of a saturated heterocycle of the present specification include a fully saturated monocyclic ring structure, for example. The ring can be a 3- to 7-membered ring which includes at least one, for example 1 to 3, preferably 1 of one or at least two kinds of heteroatoms selected from a group consisting of a nitrogen atom, a sulfur atom and an oxygen atom as a ring-constituting atom other than a carbon atom, for example. A 5- or 6-membered ring is more preferred. Specifically preferred examples include tetrahydropyran, tetrahydrofuran, piperidine, pyrrolidine, tetrahydrothiopyran, tetrahydrothiophene, morpholine, piperazine and the like. Piperidine, pyrrolidine or tetrahydropyran is a more preferred example.

As for the saturated heterocyclic group of the present specification, a monovalent residue produced by removing any single hydrogen atom from the saturated heterocyclic group described above can be mentioned, for example. Specific preferred examples of a monocyclic aromatic group include a tetrahydropyranyl group (2,3- or 4-tetrahydropyranyl group), a tetrahydrofuryl group (2- or 3-tetrahydrofuryl group), a piperidinyl group (1-, 2-, 3- or 4-piperidinyl group), a pyrrolidinyl group (1-, 2- or 3-pyrrolidinyl group), a tetrahydrothiopyranyl group (2-, 3- or 4-tetrahydrothiopyranyl group), a tetrahydrothiophenyl group (2- or 4-tetrahydrothiophenyl group), a morpholinyl group (2-, 3- or 4-morpholinyl group), a piperidinyl group (1-, 2- or 3-piperidinyl group) and the like. A piperidinyl group, a pyrrolidinyl group or tetrahydropyranyl group can be mentioned as a more preferred example.

As for the partially unsaturated hydrocarbon group of the present specification, ring similar to the partially unsaturated monocyclic carbon ring described above can be exemplified. Preferred examples include a cyclopenta-1,3-diene ring, a cyclohexa-1,3-diene ring and cyclopenta-1,3-diene ring. A cyclopenta-1,3-diene ring or a cyclohexa-1,3-diene ring is more preferred. A cyclohexa-1,3-diene ring is still more preferred, but not limited thereto.

As for the unsaturated hydrocarbon ring of the present specification, those described above for the unsaturated ring of the monocyclic aromatic hydrocarbon can be exemplified. A benzene ring is preferred.

As for the aryloxy group of the present specification, it indicates an aryl group which is bonded to an oxygen atom. The aryl moiety of an aryloxy group is the same as the aryl group described above. The aryl moiety of an aryloxy is preferably a monocyclic aromatic group, and the examples of an aryloxy group include a phenoxy group, a 2-thienyloxy group, a 3-thienyloxy group, a 2-pyridyloxy group, a 3-pyridyloxy group, a 4-pyridyloxy group, a 2-furyloxy group, a 3-furyloxy group, a 2-thiazolyloxy group, a 4-thiazolyloxy group, a 5-thiazolyloxy group, a 2-oxazolyloxy group, a 4-oxazolyloxy group, a 5-oxazolyloxy group, a 3-pyrazolyloxy group, a 4-pyrazolyloxy group, a 2-pyrazinyloxy group, a 2-pyrimidinyloxy group, a 4-pyrimidinyloxy group, a 5-pyrimidinyloxy group, a 2-pyrrolyloxy group, a 3-pyrrolyloxy group, a 2-imidazolyloxy group, a 4-imidazolyloxy group, a 3-pyridazinyloxy group, a 4-pyridazinyloxy group, a 3-isothiazolyloxy group, a 3-isoxazolyloxy group, a 1,2,4-oxadiazol-5-yloxy group, a 1,2,4-oxadiazol-3-yloxy group or a 3,4-dihydro-2H-pyran-6-yloxy group and the like. A phenoxy group, a 2-thienyloxy group, a 3-thienyloxy group, a 2-furyloxy group, a 3-furyloxy group, a 2-pyrrolyloxy group, a 3-pyrrolyloxy group and the like are preferred. A phenoxy group is more preferred.

As for the aralkyl group of the present specification, an alkyl group described above of which one hydrogen atom is substituted with the aryl group defined in the present specification can be mentioned. Specific examples include a benzyl group, a phenethyl group, a 1-(phenyl)ethyl group, a phenylpropyl group, a 1-naphthylmethyl group, a 2-naphthylmethyl group, a 2-pyridylmethyl group, a 3-pyridylmethyl group, a 4-pyridylmethyl group, a 2-furylmethyl group, a 3-furylmethyl group, a 2-thienylmethyl group, a 3-thienylmethyl group and the like, and a benzyl group and a phenethyl group are preferred.

As for the alkylthio group of the present specification, a saturated alkylthio ether group having 1 to 6 carbon atoms can be mentioned, and the alkyl group described above to which a sulfur atom is added can be mentioned, for example. Specific examples include a methylthio group, an ethylthio group, an n-propylthio group, an isopropylthio group, a cyclopropylthio group, an n-butylthio group, an isobutylthio group, a s-butylthio group, a t-butylthio group, a cyclobutylthio group, a cyclopropylmethylthio group and the like.

As for the acyl group of the present specification, an alkanoyl group or an arylcarbonyl group can be mentioned. As for an alkanoyl group, a saturated alkylcarbonyl group having 2 to 6 carbon atoms can be mentioned. Specific examples include an acetyl group, a propanoyl group, a butanoyl group, a 2-methylpropanoyl group, a cyclopropylcarbonyl group, a pentanoyl group, a 3-methylbutanoyl group, a 2,2-dimethylpropanoyl group, a cyclobutylcarbonyl group and the like.

As for the acyloxy group of the present specification, an alkanoyloxy group (alkylcarbonyloxy group) or an arylcarbonyloxy group can be mentioned, for example. As for an alkanoyloxy group, a saturated alkylcarbonyloxy group having 2 to 6 carbon atoms can be mentioned. Specific examples include an acetoxy group, a propanoyloxy group, a butanoyloxy group, a 2-methylpropanoyloxy group, a cyclopropylcarbonyloxy group, a pentanoyloxy group, a 3-methylbutanoyloxy group, a 2,2-dimethylpropanoyloxy group, a cyclobutylcarbonyloxy group and the like.

As for the alkylsulfinyl group of the present specification, a saturated alkylsulfinyl group having 1 to 6 carbon atoms can be mentioned. Specific examples include a methylsulfinyl group, an ethylsulfinyl group, an n-propylsulfinyl group, an isopropylsulfinyl group, a cyclopropylsulfinyl group, an n-butylsulfinyl group, an isobutylsulfinyl group, a s-butylsulfinyl group, a t-butylsulfinyl group, a cyclobutylsulfinyl group, a cyclopropylmethylsulfinyl group and the like.

As for the alkylsulfonyl group of the present specification, a saturated alkylsulfonyl group having 1 to 6 carbon atoms can be mentioned. Specific examples include a methylsulfonyl group, an ethylsulfonyl group, an n-propylsulfonyl group, an isopropylsulfonyl group, a cyclopropylsulfonyl group, an n-butylsulfonyl group, an isobutylsulfonyl group, a s-butylsulfonyl group, a t-butylsulfonyl group, a cyclobutylsulfonyl group, a cyclopropylmethylsulfonyl group and the like.

As for the alkylcarbamyl group of the present specification, a saturated alkylcarbamyl group having 2 to 6 carbon atoms can be mentioned. Specific examples include a methylcarbamyl group, an ethylcarbamyl group, an n-propylcarbamyl group, an isopropylcarbamyl group, a cyclopropylcarbamyl group, an n-butylcarbamyl group, an isobutylcarbamyl group, a s-butylcarbamyl group, a t-butylcarbamyl group, a cyclobutylcarbamyl group, a cyclopropylmethylcarbamyl group and the like.

As for the alkylamino group of the present specification, a saturated alkylamino group having 1 to 6 carbon atoms can be mentioned. Specific examples include a methylamino group, an ethylamino group, an n-propylamino group, an isopropylamino group, a cyclopropylamino group, an n-butylamino group, an isobutylamino group, a s-butylamino group, a t-butylamino group, a cyclobutylamino group, a cyclopropylmethylamino group and the like.

As for the dialkylamino group of the present specification, an amino group substituted with one to six same or different alkyl groups can be mentioned. Specific examples include a dimethylamino group, an ethyl(methyl)amino group, a diethylamino group, a methyl(n-propyl)amino group, an isopropyl(methyl)amino group, a cyclopropyl(methyl)amino group, an n-butyl(methyl)amino group, an isobutyl(methyl)amino group, a s-butyl(methyl)amino group, a t-butyl(methyl)amino group, a cyclobutyl(methyl)amino group, a cyclopropylmethyl(methyl)amino and the like. Further, two substituents on the nitrogen may together form a 3- to 7-membered ring to yield a cyclic amine, and in such case, as a dialkylamino group, a 3- to 7-membered cyclic amine can be mentioned. Specific examples include a pyrrolidino group, a piperidine group and the like.

As for the acylamino group of the present specification, an amino group which is substituted with the acyl group described above can be mentioned. Specific examples include an acetylamino group, a propanoylamino group, a butanoylamino group, a 2-methylpropanoylamino group, a cyclopropylcarbonylamino group, a pentanoylamino group, a 3-methylbutanoylamino group, a 2,2-dimethylpropanoylamino group, a cyclobutylcarbonylamino group and the like.

As for the acyl(alkyl)amino group of the present specification, an amino group which is substituted simultaneously with one acyl group described above and one alkyl group described above can be mentioned. Specific examples include an acetyl(methyl)amino group, a methyl(propanoyl)amino group, a butanoyl(methyl)amino group, a methyl(2-methylpropanoyl)amino group, a cyclopropylcarbonyl(methyl) amino group, a methyl(pentanoyl)amino group, a methyl(3-methylbutanoyl)amino group, a 2,2-dimethylpropanoyl (methyl)amino group, a cyclobutylcarbonyl(methyl)amino group and the like.

As for the alkylsulfonylamino group of the present specification, an amino group which is substituted with the alkylsulfonyl group described above can be mentioned. Specific examples include a methylsulfonylamino group, an ethylsulfonylamino group, an n-propylsulfonylamino group, an isopropylsulfonylamino group, a cyclopropylsulfonylamino group, an n-butylsulfonylamino group, an isobutylsulfonylamino group, a s-butylsulfonylamino group, a t-butylsulfonylamino group, a cyclobutylsulfonylamino group, a cyclopropylmethylsulfonylamino group and the like.

As for the alkylsulfonyl(alkyl)amino group of the present specification, an amino group which is substituted simultaneously with one alkylsulfonyl group described above and one alkyl group described above can be mentioned. Specific examples include a methyl(methylsulfonyl)amino group, an ethylsulfonyl(methyl)amino group, a methyl(n-propylsulfonyl)amino group, an isopropylsulfonyl(methyl)amino group, a cyclopropylsulfonyl(methyl)amino group, an n-butylsulfonyl(methyl)amino group, an isobutylsulfonyl(methyl)amino group, a s-butylsulfonyl(methyl)amino group, a t-butylsulfonyl(methyl)amino group, a cyclobutylsulfonyl(methyl) amino group, a cyclopropylmethylsulfonyl(methyl)amino group and the like.

As for a group which may be substituted in the present specification (i.e., an alkyl group, an alkenyl group, an alkynyl group, an aryl group, an aralkyl group, an alkoxy group, an aryloxy group, an alkylene group, a methylene group, an alkenylene group and the like), an unsubstituted group or a group which is substituted generally with one to several substituents within the upper limit, that is the maximum number of allowed substitution, can be mentioned.

As for a substituent for the alkyl group which may be substituted in the present specification, a hydroxy group, a cyano group, a halogen atom, an aryl group, an aryloxy group, an alkoxy group, an alkylthio group, an acyl group, an acyloxy group, an alkylsulfinyl group, an alkylsulfonyl group, an alkylcarbamyl group, an amino group, an alkylamino group, a dialkylamino group, an acylamino group, an acyl(alkyl) amino group, an alkylsulfonylamino group, an alkylsulfonyl (alkyl)amino group and the like can be mentioned.

As for a substituent for the alkylene group which may be substituted in the present specification, the substituent described for the alkyl group which may be substituted as described above can be also mentioned.

As for a substituent for the methylene group which may be substituted with a lower alkyl group as described in the present specification, an alkyl group having 1 to 6 carbon atoms is preferred. An alkyl group having 1 to 3 carbon atoms is more preferred. Examples of an alkyl group having 1 to 3 carbon atoms include a methyl group, an ethyl group, an n-propyl group, an isopropyl group, a cyclopropyl group and the like. Examples of an alkyl group having 4 to carbon atoms include an n-butyl group, an isobutyl group, a s-butyl group, a t-butyl group, a cyclobutyl group, a cyclopropylmethyl group, an n-pentyl group, a cyclopentyl group, a cyclopropylethyl group, a cyclobutylmethyl group, an n-hexyl group, a cyclohexyl group, a cyclopropylpropyl group, a cyclobutylethyl group, a cyclopentylmethyl group and the like.

As for a substituent for the alkenyl group which may be substituted in the present specification, the substituent described for the alkyl group which may be substituted as described above can be also mentioned.

As for a substituent for the alkenylene group which may be substituted in the present specification, the substituent described for the alkyl group which may be substituted as described above can be also mentioned.

As for a substituent for the alkynyl group which may be substituted as described in the present specification, the substituent described for the alkyl group which may be substituted as described above can be also mentioned.

As for a substituent for the aryl ring which may be substituted and a substituent for the aryl group which may be substituted in the present specification, a hydroxy group, a halogen atom, an alkyl group which may be substituted, an alkenyl group which may be substituted, an alkynyl group which may be substituted, an aryl group, an alkoxy group which may be substituted, an alkylthio group, an acyl group, an acyloxy group, an alkylsulfinyl group, an alkylsulfonyl group, an alkylcarbamyl group, —N($R^{411}$) ($R^{412}$) ($R^{411}$ and $R^{412}$ can be the same or different to each other, and each independently represent a hydrogen atom, an alkyl group which may be substituted or an aryl group which may be substituted, or $R^{411}$ and $R^{412}$ together form a 3- to 7-membered ring to represent a cyclic amine of N($R^{411}$) ($R^{412}$).), an acylamino group, an acyl(alkyl)amino group, an alkylsulfonylamino group, an alkylsulfonyl(alkyl)amino group, a carboxy group, —CON($R^{413}$) ($R^{414}$) ($R^{413}$ and $R^{414}$ can be the same or different to each other, and each independently represent a hydrogen atom, an alkyl group which may be substituted or an aryl group which may be substituted, or $R^{413}$ and $R^{414}$ together form a 3- to 7-membered ring to represent a cyclic amine of N($R^{413}$) ($R^{414}$).) or —COO$R^{415}$ ($R^{415}$ represents an alkyl group which may be substituted.), and the number of substituent is not specifically limited, if it is an allowed number of substitution. Preferably, it is between 1 and 3. When two or more substituents are present, they can be the same or different to each other.

As for an aralkyl group which may be substituted in the present specification, the alkyl group which may be substituted as described above of which one hydrogen atom is substituted with an aryl group which may be substituted as described in the present specification can be mentioned.

As for a substituent for the alkoxy group which may be substituted in the present specification, the substituent described for the alkyl group which may be substituted as described above can be also mentioned.

As for a substituent for the aryloxy group which may be substituted in the present specification, the substituent described for the alkyl group which may be substituted as described above can be also mentioned.

Next, each substituent for the compounds of the present invention will be described more specifically.

Cy represents an aryl group, a saturated cyclic hydrocarbon group, or a saturated heterocyclic group. Aryl group is preferred as Cy. In addition, there is other embodiment in which a saturated heterocyclic group is preferred.

When Cy represents an aryl group, a preferred examples of the aryl group include a phenyl group, a cyclopentenyl group (1-, 3- or 4-cyclopentenyl group), a cyclohexenyl group (1-, 3- or 4-cyclohexenyl group), a thienyl group (2- or 3-thienyl group), a pyridyl group (2-, 3- or 4-pyridyl group), a furyl group (2- or 3-furyl group), a thiazolyl group (2-, 4- or 5-thiazolyl group), an oxazolyl group (2-, 4- or 5-oxazolyl group), a pyrazolyl group (1-, 3- or 4-pyrazolyl group), a 2-pyrazinyl group, a pyrimidinyl group (2-, 4- or 5-pyrimidinyl group), a pyrrolyl group (1-, 2- or 3-pyrrolyl group), an imidazolyl group (1-, 2- or 4-imidazolyl group), a pyridazinyl group (3- or 4-pyridazinyl group), a 3-isothiazolyl group, a 3-isoxazolyl group, a 1,2,4-oxadiazol-5-yl group, a 1,2,4-oxadiazol-3-yl group, a 2,3-dihydrofuran-2-yl group, a 2,3-dihydrofuran-3-yl group, a 2,3-dihydrofuran-4-yl group, a 2,3-dihydrofuran-5-yl group, a 2,5-dihydrofuran-2-yl group, a 2,5-dihydrofuran-3-yl group, a 2,3-dihydrothiophen-5-yl group, a 3,4-dihydro-2H-pyran-2-yl group, a 3,4-dihydro-2H-pyran-3-yl group, a 3,4-dihydro-2H-pyran-4-yl group, a 3,4-dihydro-2H-pyran-5-yl group, a 3,4-dihydro-2H-pyran-6-yl group, a 3,6-dihydro-2H-pyran-2-yl group, a 3,6-dihydro-2H-pyran-3-yl group, a 3,6-dihydro-2H-pyran-4-yl group, a 3,6-dihydro-2H-pyran-5-yl group, a 3,6-dihydro-2H-pyran-6-yl group, a 3,4-dihydro-2H-thiopyran-6-yl group, a 1-naphthyl group, a 2-naphthyl group, a 2-indenyl group, a 2-anthryl group, a quinolyl group (2-, 3-, 4-, 5-, 6-, 7- or 8-quinolyl group), an isoquinolyl group (1-, 3-, 4-, 5-, 6-, 7- or 8-isoquinolyl group), an indolyl group (1-, 2-, 3-, 4-, 5-, 6- or 7-indolyl group), an isoindolyl group (1-, 2-, 4- or 5-isoindolyl group), a phthalazinyl group (1-, 5- or 6-phthalazinyl group), a quinoxalinyl group (2-, 3- or 5-quinoxalinyl group), a benzofuranyl group (2-, 3-, 4-, 5- or 6-benzofuranyl group), a benzothiazolyl group (2-, 4-, 5- or 6-benzothiazolyl group), a benzimidazolyl group (1-, 2-, 4-, 5- or 6-benzimidazolyl group), a 2,1,3-benzoxadiazol-4-yl group, a 2,1,3-benzoxadiazol-5-yl group, a 2,1,3-benzoxadiazol-6-yl group, a fluorenyl group (1-, 2-, 3- or 4-fluorenyl group) and a thioxanthenyl group. A phenyl group, a 1-cyclopentenyl group, a 1-cyclohexenyl group, a 2-thienyl group, a 3-thienyl group, a 3-pyridyl group, a 2-furyl group, a 3-furyl group, a 3-pyrazolyl group, a 4-pyrazolyl group, a 5-pyrimidinyl group, a 2-pyrrolyl group, a 3-pyrrolyl group, a 3,4-dihydro-2H-pyran-6-yl group, a 2-naphthyl group, a 3-quinolyl group, 8-quinolyl group, 6-indolyl group or a 2,1,3-benzoxadiazol-5-yl group is more preferred. A phenyl group, a 1-cyclopentenyl group, a 1-cyclohexenyl group, a 2-thienyl group, a 3-thienyl group, a 3-pyridyl group, a 2-furyl group, a 3-furyl group, a 3,4-dihydro-2H-pyran-6-yl group or a 8-quinolyl group is still more preferred. A phenyl group, a 2-thienyl group or a 3-thienyl group is even still more preferred. A phenyl group is most preferred.

Further, when Cy represents an aryl group, there is other embodiment in which it is preferably a partially unsaturated monocyclic carbon ring group or a monocyclic heterocycle group. Specifically, as a partially unsaturated monocyclic carbon ring group, a cyclopentenyl group (1-, 3- or 4-cyclopentenyl group) or a cyclohexenyl group (1-, 3- or 4-cyclohexenyl group) is exemplified and a 1-cyclopentenyl group or a 1-cyclohexenyl group is preferred. A 1-cyclohexenyl group is more preferred.

Further, as a partially unsaturated monocyclic heterocycle group, specific examples include a 2,3-dihydrofuran-2-yl group, a 2,3-dihydrofuran-3-yl group, a 2,3-dihydrofuran-4-yl group, a 2,3-dihydrofuran-5-yl group, a 2,5-dihydrofuran-2-yl group, a 2,5-dihydrofuran-3-yl group, a 2,3-dihydrothiophen-5-yl group, a 3,4-dihydro-2H-pyran-2-yl group, a 3,4-dihydro-2H-pyran-3-yl group, a 3,4-dihydro-2H-pyran-4-yl group, a 3,4-dihydro-2H-pyran-5-yl group, a 3,4-dihydro-2H-pyran-6-yl group, a 3,6-dihydro-2H-pyran-2-yl group, a 3,6-dihydro-2H-pyran-3-yl group, a 3,6-dihydro-2H-pyran-4-yl group, a 3,6-dihydro-2H-pyran-5-yl group, a 3,6-dihydro-2H-pyran-6-yl group and a 3,4-dihydro-2H-thiopyran-6-yl group. A 2,3-dihydrofuran-5-yl group and a 3,4-dihydro-2H-pyran-6-yl group are preferred. A 3,4-dihydro-2H-pyran-6-yl group is more preferred.

When Cy represents a saturated cyclic hydrocarbon group, a cyclopenyl group or a cyclohexyl group is preferred.

When Cy represents a saturated heterocycle group, a tetrahydropyranyl group (2,3- or 4-tetrahydropyranyl group), a tetrahydrofuryl group (2- or 3-tetrahydrofuryl group), a piperidinyl group (1-, 2-, 3- or 4-piperidinyl group), a pyrrolidinyl group (1-, 2- or 3-pyrrolidinyl group), a tetrahydrothiopyranyl group (2-, 3- or 4-tetrahydrothiopyranyl group), a tetrahydrothiophenyl group (2- or 4-tetrahydrothiophenyl group), a morpholinyl group (2-, 3- or 4-morpholinyl group) or a piperidinyl group (1-, 2- or 3-piperidinyl group) is preferred. A 1-pyrrolidinyl group is more preferred.

X represents a carbon atom or a nitrogen atom. A carbon atom is preferred as X.

Y represents a carbon atom, a nitrogen atom, an oxygen atom or a sulfur atom. A carbon atom is preferred as Y.

$R^1$, $R^2$ and $R^3$ can be the same or different to each other, and each independently represent a hydrogen atom, a halogen atom, an alkyl group which may be substituted, an alkenyl group which may be substituted, an alkynyl group which may be substituted, an aryl group which may be substituted, an aralkyl group which may be substituted, a hydroxy group, an alkoxy group which may be substituted, an aryloxy group which may be substituted, an alkylthio group, an acyl group, an acyloxy group, an alkylsulfinyl group, an alkylsulfonyl group, an alkylcarbamyl group, —N($R^{P1}$)($R^{P2}$) ($R^{P1}$ and $R^{P2}$ can be the same or different to each other, and each independently represent a hydrogen atom, an alkyl group which may be substituted or an aryl group which may be substituted, or $R^{P1}$ and $R^{P2}$ together form a 3- to 7-membered ring to represent a cyclic amine of N($R^{P1}$) ($R^{P2}$).) an acylamino group, an acyl(alkyl)amino group, an alkylsulfonylamino group, an alkylsulfonyl(alkyl)amino group, a carboxy group, —CON($R^{P3}$) ($R^{P4}$) ($R^{P3}$ and $R^{P4}$ can be the same or different to each other, and each independently represent a hydrogen atom, an alkyl group which may be substituted or an aryl group which may be substituted, or $R^{P3}$ and $R^{P4}$ together form a 3- to 7-membered ring to represent a cyclic amine of N($R^{P3}$) ($R^{P4}$).) or —COO$R^{P5}$ ($R^{P5}$ represents an alkyl group which may be substituted.). As $R^1$, $R^2$ and $R^3$, a hydrogen atom, a halogen atom, an alkyl group which may be substituted, a hydroxy group, or an alkoxy group which may be substituted is preferred. A hydrogen atom, a halogen atom or a hydroxy group is more preferred. A hydrogen atom or a hydroxy group is still more preferred. A hydrogen atom is even still more preferred.

As for the halogen atom that is represented by $R^1$, $R^2$ and $R^3$, preferred examples include a fluorine atom or a chlorine atom. A fluorine atom is more preferred. As for the alkyl group which may be substituted and represented by $R^1$, $R^2$ and $R^3$, preferred examples include a methyl group, an ethyl group, an n-propyl group, an isopropyl group or a trifluoromethyl group. A methyl group is more preferred. In addition, there is other embodiment in which a trifluoromethyl group is preferred. As for the alkoxy group which may be substituted and represented by $R^1$, $R^2$ and $R^3$, preferred examples include a methoxy group, an ethoxy group, an n-propoxy group, an isopropoxy group or a trifluoromethyloxy group. A methoxy group is more preferred. In addition, there is other embodiment in which a trifluoromethyloxy group is more preferred.

It is preferable that any one of $R^1$, $R^2$ and $R^3$ is a hydrogen atom. It is more preferable that any two of them are a hydrogen atom. It is also possible that $R^1$, $R^2$ and $R^3$ are all simultaneously a hydrogen atom. $R^1$ is present on a carbon atom which is adjacent to the carbon atom on a benzene ring binding to the pyrazole ring. When at least one of $R^2$ and $R^3$ is a substituent other than a hydrogen atom, its (or their) substitution position is not specifically limited and it can be present on any position on the benzene ring.

$R^4$ is a hydrogen atom, a halogen atom, an alkyl group which may be substituted, an alkenyl group which may be substituted, an alkynyl group which may be substituted, a hydroxy group, an alkoxy group which may be substituted, —N($R^{41}$)($R^{42}$) ($R^{41}$ and $R^{42}$ can be the same or different to each other, and each independently represent a hydrogen atom, an alkyl group which may be substituted or an aryl group which may be substituted, or $R^{41}$ and $R^{42}$ together form a 3- to 7-membered ring to represent a cyclic amine of N($R^{41}$)($R^{42}$).). Preferably, $R^4$ is a hydrogen atom, a halogen atom, an alkyl group which may be substituted, a hydroxy group or an amino group. More preferably, it is a halogen atom, an alkyl group which may be substituted or an amino group. Still more preferably, it is an alkyl group which may be substituted. There is other embodiment in which an amino group is more preferred as $R^4$.

As for the halogen atom represented by $R^4$, a fluorine atom, a chlorine atom, or a bromine atom is preferred, for example. A fluorine atom or a chlorine atom is more preferred. There is other embodiment in which a bromine atom is more preferred for the halogen atom of $R^4$. As for the alkyl group which may be substituted as represented by $R^1$, $R^2$ or $R^3$, for example, a methyl group, an ethyl group, an n-propyl group, an isopropyl group or a trifluoromethyl group is preferred. A methyl group is more preferred.

Further, $R^1$ and $R^4$ may together represent a ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom or a nitrogen atom, and it is preferable that $R^1$ and $R^4$ together represent a partially unsaturated hydrocarbon ring or a ring in which one of the ring-constituting carbon atoms in the ring is substituted with an oxygen atom or a sulfur atom.

As for the partially unsaturated hydrocarbon ring, a cyclopenta-1,3-diene ring, a cyclohexa-1,3-diene ring or a cyclohepta-1,3-diene ring can be mentioned. A cyclopenta-1,3-diene ring or a cyclohexa-1,3-diene ring are preferred. A cyclohexa-1,3-diene ring is more preferred.

As for the unsaturated hydrocarbon ring, a benzene ring can be mentioned.

As for the ring in which one of the ring-constituting carbon atoms in the partially unsaturated hydrocarbon ring or the unsaturated hydrocarbon ring is substituted with an oxygen atom, a sulfur atom or a nitrogen atom, a thiophene ring, a furan ring, a pyrrole ring, a 2H-pyran ring, a 2H-thiopyran ring, a 1,2-dihydropyridine ring or a pyridine ring can be mentioned. A thiophene ring, a furan ring, a 2H-pyran ring or a 2H-thiopyran ring is preferred. A thiophene ring or a furan ring is more preferred.

When $R^1$ and $R^4$ together represent a ring, as a compound of the formula (1), a compound having any of the following formulas (1-1) to (1-5) is preferred:

[Chemical Formula 3]

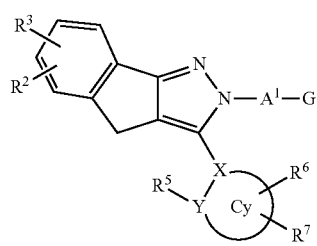
(1-1)

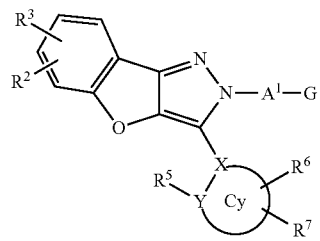
(1-2)

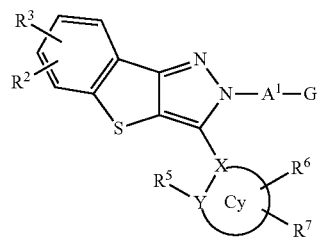
(1-3)

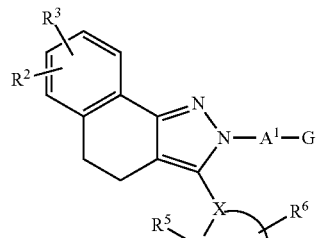
(1-4)

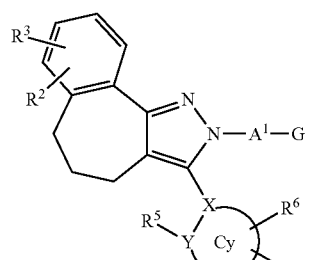
(1-5)

[in the formulas (1-1) to (1-5), Cy, X, Y, $R^2$, $R^3$, $R^5$, $R^6$, $R^7$, $A^1$ and G are as defined in the above, with the proviso that $R^5$ is not formed with $R^4$.] and the compound of the formula (1-4) is more preferred.

Further, when $R^1$ and $R^4$ together represent a cyclopenta-1,3-diene ring for example, it indicates that the compound of the formula (1) corresponds to the formula (1-1). Further, when $R^1$ and $R^4$ together represent a furan ring, for example, it indicates that the compound of the formula (1) corresponds to the formula (1-2).

As for the $R^5$, $R^6$ and $R^7$, all or part of them may be present, or none of them may be present. When $R^5$ is present, Y on Cy is a carbon atom or a nitrogen atom, and it indicates that it is present on this carbon atom or on a nitrogen atom. When at least one of $R^6$ and $R^7$ is present, its (or their) substitution position is not specifically limited and it can be present on any substitutable position of Cy.

$R^5$, $R^6$ and $R^7$ can be the same or different to each other, and when they present, each independently represent a hydrogen atom, a halogen atom, an alkyl group which may be substituted, an alkenyl group which may be substituted, an alkynyl group which may be substituted, an aryl group which may be substituted, an aralkyl group which may be substituted, a hydroxy group, an alkoxy group which may be substituted, an aryloxy group which may be substituted, an alkylthio group, an acyl group, an acyloxy group, an alkylsulfinyl group, an alkylsulfonyl group, an alkylcarbamyl group, —N($R^{Y1}$)($R^{Y2}$) ($R^{Y1}$ and $R^{Y2}$ can be the same or different to each other, and each independently represent a hydrogen atom, an alkyl group which may be substituted or an aryl group which may be substituted, or $R^{Y1}$ and $R^{Y2}$ together form a 3- to 7-membered ring to represent a cyclic amine of N($R^{Y1}$) ($R^{Y2}$).), an acylamino group, an acyl(alkyl)amino group, an alkylsulfonylamino group, an alkylsulfonyl(alkyl)amino group, a carboxy group, —CON($R^{Y3}$) ($R^{Y4}$) ($R^{Y3}$ and $R^{Y4}$ can be the same or different to each other, and each independently represent a hydrogen atom, an alkyl group which may be substituted or an aryl group which may be substituted, or $R^{Y3}$ and $R^{Y4}$ together form a 3- to 7-membered ring to represent a cyclic amine of N($R^{Y3}$) ($R^{Y4}$).) or —COO$R^{Y5}$ ($R^{Y5}$ represents an alkyl group which may be substituted.). As for the $R^5$, $R^6$ and $R^7$, a hydrogen atom, a halogen atom, an alkyl group which may be substituted, a hydroxy group, or an alkoxy group which may be substituted is preferred. A hydrogen atom or a halogen atom is more preferred. There is other embodiment in which a hydroxy group is more preferred.

As for the halogen atom as represented by $R^5$, $R^6$ or $R^7$, a fluorine atom or a chlorine atom is preferred. A fluorine atom is more preferred. As for the alkyl group which may be substituted as represented by $R^5$, $R^6$ or $R^7$, a methyl group, for example, an ethyl group, an n-propyl group, an isopropyl group or a trifluoromethyl group is preferred. A methyl group is more preferred. There is other embodiment in which a trifluoromethyl group is more preferred. As for the alkoxy group which may be substituted as represented by $R^5$, $R^6$ or $R^7$, for example, a methoxy group, an ethoxy group, an n-propoxy group, an isopropoxy group or a trifluoromethyloxy group is preferred. A methoxy group is more preferred. There is other embodiment in which a trifluoromethyloxy group is more preferred.

Further, when $R^4$ and $R^5$ together represent a ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom or a nitrogen atom, and it is preferable that Cy is a benzene ring and $R^4$ and $R^5$ together represent a partially unsaturated hydrocarbon ring or a ring in which one of the ring-constituting carbon atoms in the ring is substituted with an oxygen atom or a sulfur atom.

As for the partially unsaturated hydrocarbon ring, a cyclopenta-1,3-diene ring, a cyclohexa-1,3-diene ring or a cyclohepta-1,3-diene ring can be mentioned. A cyclopenta-1,3-diene ring or a cyclohexa-1,3-diene ring is preferred. A cyclohexa-1,3-diene ring is more preferred.

As for the unsaturated hydrocarbon ring, a benzene ring can be mentioned.

As for the ring in which one of the ring-constituting carbon atoms in the partially unsaturated hydrocarbon ring or the unsaturated hydrocarbon ring is substituted with an oxygen atom, a sulfur atom or a nitrogen atom, a thiophene ring, a furan ring, a pyrrole ring, a 2H-pyran ring, a 2H-thiopyran ring, a 1,2-dihydropyridine ring or a pyridine ring can be mentioned. A thiophene ring, a furan ring, a 2H-pyran ring or a 2H-thiopyran ring is preferred. A thiophene ring or a furan ring is more preferred.

When $R^4$ and $R^5$ together represent a ring, as a compound of the formula (1), a compound having any of the following formulas (1-6) to (1-10) is preferred:

[Chemical Formula 4]

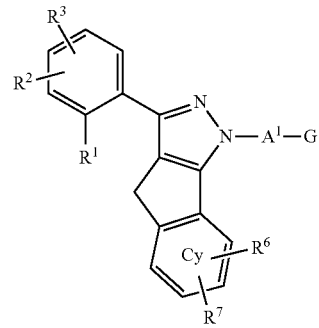

(1-6)

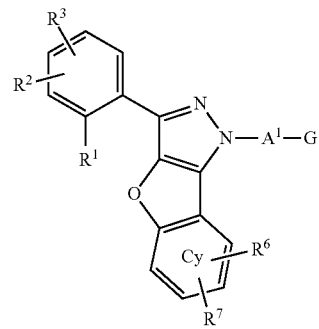

(1-7)

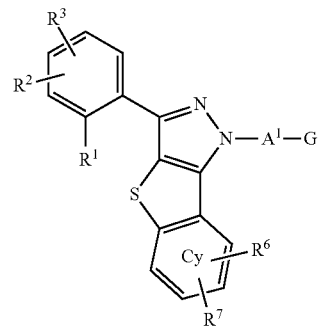

(1-8)

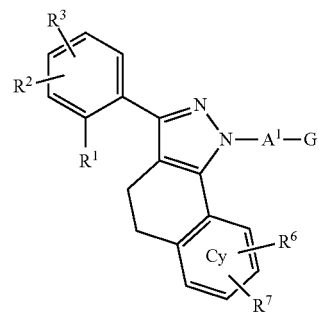

(1-9)

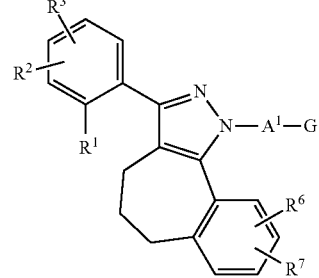

(1-10)

[in the formulas (1-6) to (1-10), Cy, $R^1$, $R^2$, $R^3$, $R^6$, $R^7$, $A^1$ and G are as defined in the above, with the proviso that $R^1$ is not formed with $R^4$.] and the compound of the formula (1-6) or formula (1-7) is more preferred. The compound of the formula (1-6) is still more preferred. Further, there is other embodiment in which the compound of the formula (1-7) is still more preferred.

Further, when $R^4$ and $R^5$ together represent a cyclopenta-1,3-diene ring for example, it indicates that the compound of the formula (1) corresponds to the formula (1-6). Further, when $R^4$ and $R^5$ together represent a furan ring, for example, it indicates that the compound of the formula (1) corresponds to the formula (1-7).

However, in no case, $R^1$ and $R^4$ together represent a ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom or a nitrogen atom and at the same time $R^4$ and $R^5$ together represent a ring which is selected from a group consisting of a partially unsaturated hydrocarbon ring which may be substituted and an unsaturated hydrocarbon ring which may be substituted or a ring in which one of the ring-constituting carbon atoms in the ring is substituted with an oxygen atom, a sulfur atom or a nitrogen atom.

$A^1$ represents a single bond, an alkylene group which may be substituted or an alkenylene group which may be substituted. Preferably, $A^1$ represents a single bond, an alkylene group or an alkenylene group. More preferably, it is a single bond, a methylene group which may be substituted with a lower alkyl group or an ethenylene group which may be substituted with a lower alkyl group. Still more preferably, it is a single bond. There is other embodiment in which a methylene group is more preferred. Further, there is other embodiment in which an ethenylene group is more preferred. With respect to stereochemistry relating to a double bond included in the ethenylene group represented by $A^1$, any of cis and trans is acceptable. Preferred stereochemistry is cis.

G represents any one of the following formulas ($G^1$) to ($G^4$)

[Chemical Formula 5]

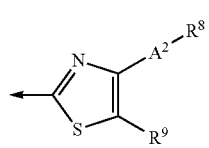
($G^1$)

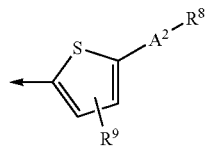
($G^2$)

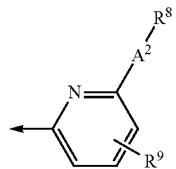
($G^3$)

-continued

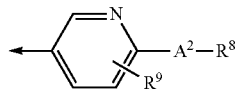
($G^4$)

[in the formulas ($G^1$) to ($G^4$), $A^2$ represents a single bond, an alkylene group, or an alkenylene group which may be substituted, $R^8$ represents a carboxy group, —CON($R^{81}$)($R^{82}$) ($R^{81}$ and $R^{82}$ can be the same or different to each other, and each independently represent a hydrogen atom, an alkyl group which may be substituted, or an aryl group which may be substituted, or $R^{81}$ and $R^{82}$ together form a 3- to 7-membered ring to represent a cyclic amine of N($R^{81}$) ($R^{82}$).), —COOR$^{83}$ ($R^{83}$ represents an alkyl group which may be substituted.) or a tetrazol-5-yl group, and $R^9$ represents a hydrogen atom or an alkyl group which may be substituted]. Further, the arrow included in the formulas ($G^1$) to ($G^4$) indicates a position for bonding with $A^1$.

G is preferably those represented by the formula ($G^1$). There is other embodiment in which G is preferably those represented by the formula ($G^2$). Further, there is other embodiment in which G is preferably those represented by the formula ($G^3$). Still further, there is other embodiment in which G is preferably those represented by the formula ($G^4$).

$A^2$ represents a single bond, an alkylene group or an alkenylene group which may be substituted. Preferably, $A^2$ represents a single bond, an alkylene group having two or less carbon atoms which may be substituted with a lower alkyl group, or an ethenylene group which may be substituted with a lower alkyl group. More preferably, it is a single bond. There is other embodiment in which $A^2$ is more preferably an ethenylene group. With respect to stereochemistry relating to a double bond included in the ethenylene group represented by $A^2$, any of cis and trans is acceptable. Preferred stereochemistry includes trans.

$R^8$ represents a carboxy group, —CON($R^{81}$) ($R^{82}$) ($R^{81}$ and $R^{82}$ can be the same or different to each other, and each independently represent a hydrogen atom, an alkyl group which may be substituted or an aryl group which may be substituted, or $R^{81}$ and $R^{82}$ together form a 3- to 7-membered ring to represent a cyclic amine of N($R^{81}$) ($R^{82}$).), —COOR$^{83}$ ($R^{83}$ represents an alkyl group which may be substituted.) or a tetrazol-5-yl group. As $R^8$, a carboxy group or —COOR$^{83}$ ($R^{83}$ is as defined above) is preferred. A carboxy group is more preferred. $R^{83}$ is not specifically limited if it is the alkyl group which may be substituted as described above. A lower alkyl group is more preferred. A methyl group or an ethyl group is still more preferred.

$R^9$ represents a hydrogen atom or an alkyl group which may be substituted. $R^9$ is preferably a hydrogen atom. $R^9$ is present at position 5 of the thiazole ring of the formula ($G^1$). $R^9$ may present on any carbon atom on the formulas ($G^2$) to ($G^4$) except the bonding position to $A^1$ and $A^2$. As for the alkyl group which may be substituted as represented by $R^9$, a lower alkyl group is preferred. A methyl group or an ethyl group is more preferred. A methyl group is still more preferred.

Combination of the substituents for the compounds of the present invention is not specifically limited, and preferred examples thereof include the followings:

<A1> A compound in which G represents the formula ($G^1$);

<A2> A compound in which G represents the formula ($G^2$);

<A3> A compound in which G represents the formula ($G^3$);

<A4> A compound in which G represents the formula ($G^4$);

<B1> A compound in which $R^8$ is a carboxy group;
<B2> A compound in which $R^8$ is —$COOR^{83}$;
<B3> A compound in which $R^8$ is tetrazol-5-yl group;
<C1> A compound corresponding to <B1> among any of the above <A1> to <A4>;
<C2> A compound corresponding to <B2> among any of the above <A1> to <A4>;
<C3> A compound corresponding to <B3> among any of the above <A1> to <A4>;
<D1> A compound in which $A^2$ is a single bond;
<D2> A compound in which $A^2$ is an alkylene group;
<D3>> A compound in which $A^2$ is an alkylene group having two or less carbon atoms which may be substituted with a lower alkyl group;
<D4> A compound in which $A^2$ is an ethylene group;
<D5> A compound in which $A^2$ is a methylene group;
<D6> A compound in which $A^2$ is an alkenylene group;
<D7> A compound in which $A^2$ is an ethenylene group which may be substituted with a lower alkyl group;
<D8> A compound in which $A^2$ is an ethenylene group;
<E1> A compound corresponding to <D1> among any of the above <A1> to <C3>;
<E2> A compound corresponding to <D2> among any of the above <A1> to <C3>;
<E3> A compound corresponding to <D3> among any of the above <A1> to <C3>;
<E4> A compound corresponding to <D4> among any of the above <A1> to <C3>;
<E5> A compound corresponding to <D5> among any of the above <A1> to <C3>;
<E6> A compound corresponding to <D6> among any of the above <A1> to <C3>;
<E7> A compound corresponding to <D7> among any of the above <A1> to <C3>;
<E8> A compound corresponding to <D8> among any of the above <A1> to <C3>;
<F1> A compound in which $A^1$ is a single bond;
<F2> A compound in which $A^1$ is an alkylene group;
<F3> A compound in which $A^1$ is an alkylene group having two or less carbon atoms which may be substituted with a lower alkyl group;
<F4> A compound in which $A^1$ is an ethylene group;
<F5> A compound in which $A^1$ is a methylene group;
<F6> A compound in which $A^1$ is an alkenylene group;
<F7> A compound in which $A^1$ is an ethenylene group which may be substituted with a lower alkyl group;
<F8> A compound in which $A^1$ is an ethenylene group;
<G1> A compound corresponding to <F1> among any of the above <A1> to <E8>;
<G2> A compound corresponding to <F2> among any of the above <A1> to <E8>;
<G3> A compound corresponding to <F3> among any of the above <A1> to <E8>;
<G4> A compound corresponding to <F4> among any of the above <A1> to <E8>;
<G5> A compound corresponding to <F5> among any of the above <A1> to <E8>;
<G6> A compound corresponding to <F6> among any of the above <A1> to <E8>;
<G7> A compound corresponding to <F7> among any of the above <A1> to <E8>;
<G8> A compound corresponding to <F8> among any of the above <A1> to <E8>;
<H1> A compound in which Cy is a phenyl group;
<H2> A compound in which Cy is a 1-cyclopentenyl group;
<H3> A compound in which Cy is a 1-cyclohexenyl group;
<H4> A compound in which Cy is a 2-thienyl group;
<H5> A compound in which Cy is a 3-thienyl group;
<H6> A compound in which Cy is a 3-pyridyl group;
<H7> A compound in which Cy is a 2-furyl group;
<H8> A compound in which Cy is a 3-furyl group;
<H9> A compound in which Cy is a 3,4-dihydro-2H-pyran-6-yl group;
<H10> A compound in which Cy is a 8-quinolyl group;
<H11> A compound in which Cy is a cyclopentyl group;
<H12> A compound in which Cy is a cyclohexyl group;
<H13> A compound in which Cy is a 1-pyrrolidinyl group;
<I1> A compound corresponding to <H1> among any of the above <A1> to <G8>;
<I2> A compound corresponding to <H2> among any of the above <A1> to <G8>;
<I3> A compound corresponding to <H3> among any of the above <A1> to <G8>;
<I4> A compound corresponding to <H4> among any of the above <A1> to <G8>;
<I5> A compound corresponding to <H5> among any of the above <A1> to <G8>;
<I6> A compound corresponding to <H6> among any of the above <A1> to <G8>;
<I7> A compound corresponding to <H7> among any of the above <A1> to <G8>;
<I8> A compound corresponding to <H8> among any of the above <A1> to <G8>;
<I9> A compound corresponding to <H9> among any of the above <A1> to <G8>;
<I10> A compound corresponding to <H10> among any of the above <A1> to <G8>;
<I11> A compound corresponding to <H11> among any of the above <A1> to <G8>;
<I12> A compound corresponding to <H12> among any of the above <A1> to <G8>;
<I13> A compound corresponding to <H13> among any of the above <A1> to <G8>;
<J1> A compound in which $R^2$ is a hydrogen atom;
<J2> A compound in which $R^2$ is a hydroxy group;
<J3> A compound in which $R^2$ is a fluorine atom;
<J4> A compound in which $R^2$ is a chlorine atom;
<J5> A compound in which $R^2$ is a bromine atom;
<J6> A compound in which $R^2$ is a methyl group;
<J7> A compound in which $R^2$ is an ethyl group;
<J8> A compound in which $R^2$ is an n-propyl group;
<J9> A compound in which $R^2$ is an isopropyl group;
<J10> A compound in which $R^2$ is a trifluoromethyl group;
<J11> A compound in which $R^2$ is a methoxy group;
<J12> A compound in which $R^2$ is an ethoxy group;
<J13> A compound in which $R^2$ is an n-propoxy group;
<J14> A compound in which $R^2$ is an isopropoxy group;
<J15> A compound in which $R^2$ is a trifluoromethyloxy group;
<K1> A compound corresponding to <J1> among any of the above <A1> to <I13>;
<K2> A compound corresponding to <J2> among any of the above <A1> to <I13>;
<K3> A compound corresponding to <J3> among any of the above <A1> to <I13>;
<K4> A compound corresponding to <J4> among any of the above <A1> to <I13>;
<K5> A compound corresponding to <J5> among any of the above <A1> to <I13>;
<K6> A compound corresponding to <J6> among any of the above <A1> to <I13>;
<K7> A compound corresponding to <J7> among any of the above <A1> to <I13>;

<K8> A compound corresponding to <J8> among any of the above <A1> to <I13>;
<K9> A compound corresponding to <J9> among any of the above <A1> to <I13>;
<K10> A compound corresponding to <J10> among any of the above <A1> to <I13>;
<K11> A compound corresponding to <J11> among any of the above <A1> to <I13>;
<K12> A compound corresponding to <J12> among any of the above <A1> to <I13>;
<K13> A compound corresponding to <J13> among any of the above <A1> to <I13>;
<K14> A compound corresponding to <J14> among any of the above <A1> to <I13>;
<K15> A compound corresponding to <J15> among any of the above <A1> to <I13>;
<L1> A compound in which $R^3$ is a hydrogen atom;
<L2> A compound in which $R^3$ is a hydroxy group;
<L3> A compound in which $R^3$ is a fluorine atom;
<L4> A compound in which $R^3$ is a chlorine atom;
<L5> A compound in which $R^3$ is a bromine atom;
<L6> A compound in which $R^3$ is a methyl group;
<L7> A compound in which $R^3$ is an ethyl group;
<L8> A compound in which $R^3$ is an n-propyl group;
<L9> A compound in which $R^3$ is an isopropyl group;
<L10> A compound in which $R^3$ is a trifluoromethyl group;
<L11> A compound in which $R^3$ is a methoxy group;
<L12> A compound in which $R^3$ is an ethoxy group;
<L13> A compound in which $R^3$ is an n-propoxy group;
<L14> A compound in which $R^3$ is an isopropoxy group;
<L15> A compound in $R^3$ is a trifluoromethyloxy group;
<M1> A compound corresponding to <L1> among any of the above <A1> to <K15>;
<M2> A compound corresponding to <L2> among any of the above <A1> to <K15>;
<M3> A compound corresponding to <L3> among any of the above <A1> to <K15>;
<M4> A compound corresponding to <L4> among any of the above <A1> to <K15>;
<M5> A compound corresponding to <L5> among any of the above <A1> to <K15>;
<M6> A compound corresponding to <L6> among any of the above <A1> to <K15>;
<M7> A compound corresponding to <L7> among any of the above <A1> to <K15>;
<M8> A compound corresponding to <L8> among any of the above <A1> to <K15>;
<M9> A compound corresponding to <L9> among any of the above <A1> to <K15>;
<M10> A compound corresponding to <L10> among any of the above <A1> to <K15>;
<M11> A compound corresponding to <L11> among any of the above <A1> to <K15>;
<M12> A compound corresponding to <L12> among any of the above <A1> to <K15>;
<M13> A compound corresponding to <L13> among any of the above <A1> to <K15>;
<M14> A compound corresponding to <L14> among any of the above <A1> to <K15>;
<M15> A compound corresponding to <L15> among any of the above <A1> to <K15>;
<N1> A compound in which $R^1$ is a hydrogen atom;
<N2> A compound in which $R^1$ is a hydroxy group;
<N3> A compound in which $R^1$ is a fluorine atom;
<N4> A compound in which $R^1$ is a chlorine atom;
<N5> A compound in which $R^1$ is a bromine atom;
<N6> A compound in which $R^1$ is a methyl group;
<N7> A compound in which $R^1$ is an ethyl group;
<N8> A compound in which $R^1$ is an n-propyl group;
<N9> A compound in which $R^1$ is an isopropyl group;
<N10> A compound in which $R^1$ is a trifluoromethyl group;
<N11> A compound in which $R^1$ is a methoxy group;
<N12> A compound in which $R^1$ is an ethoxy group;
<N13> A compound in which $R^1$ is an n-propoxy group;
<N14> A compound in which $R^1$ is an isopropoxy group;
<N15> A compound in $R^1$ is a trifluoromethyloxy group;
<N16> A compound in which $R^4$ is a hydroxy group;
<N17> A compound in which $R^4$ is an amino group;
<N18> A compound in which $R^4$ is a fluorine atom;
<N19> A compound in which $R^4$ is a chlorine group;
<N20> A compound in which $R^4$ is a bromine atom;
<N21> A compound in which $R^4$ is a methyl group;
<N22> A compound in which $R^4$ is an ethyl group;
<N23> A compound in which $R^4$ is an n-propyl group;
<N24> A compound in which $R^4$ is an isopropyl group;
<N25> A compound in which $R^4$ is a trifluoromethyl group;
<N26> A compound in which $R^5$ is a hydrogen atom;
<N27> A compound in which $R^5$ is a hydroxy group;
<N28> A compound in which $R^5$ is a fluorine atom;
<N29> A compound in which $R^5$ is a chlorine group;
<N30> A compound in which $R^5$ is a bromine atom;
<N31> A compound in which $R^5$ is a methyl group;
<N32> A compound in which $R^5$ is an ethyl group;
<N33> A compound in which $R^5$ is an n-propyl group;
<N34> A compound in which $R^5$ is an isopropyl group;
<N35> A compound in which $R^5$ is a trifluoromethyl group;
<N36> A compound in which $R^5$ is a methoxy group;
<N37> A compound in which $R^5$ is an ethoxy group;
<N38> A compound in which $R^5$ is an n-propoxy group;
<N39> A compound in which $R^5$ is an isopropoxy group;
<N40> A compound in which $R^5$ is a trifluoromethyloxy group;
<N41> A compound in which $R^1$ and $R^4$ together represent a cyclopenta-1,3-diene ring;
<N42> A compound in which $R^1$ and $R^4$ together represent a cyclohexa-1,3-diene ring;
<N43> A compound in which $R^1$ and $R^4$ together represent a thiophene ring;
<N44> A compound in which $R^1$ and $R^4$ together represent a furan ring;
<N45> A compound in which $R^4$ and $R^5$ together represent a cyclopenta-1,3-diene ring;
<N46> A compound in which $R^4$ and $R^5$ together represent a cyclohexa-1,3-diene ring;
<N47> A compound in which $R^4$ and $R^5$ together represent a thiophene ring;
<N48> A compound in which $R^4$ and $R^5$ together represent a furan ring;
<O1> A compound corresponding to <N1> among any of the above <A1> to <M15>;
<O2> A compound corresponding to <N2> among any of the above <A1> to <M15>;
<O3> A compound corresponding to <N3> among any of the above <A1> to <M15>;
<O4> A compound corresponding to <N4> among any of the above <A1> to <M15>;
<O5> A compound corresponding to <N5> among any of the above <A1> to <M15>;
<O6> A compound corresponding to <N6> among any of the above <A1> to <M15>;

<O7> A compound corresponding to <N7> among any of the above <A1> to <M15>;
<O8> A compound corresponding to <N8> among any of the above <A1> to <M15>;
<O9> A compound corresponding to <N9> among any of the above <A1> to <M15>;
<O10> A compound corresponding to <N10> among any of the above <A1> to <M15>;
<O11> A compound corresponding to <N11> among any of the above <A1> to <M15>;
<O12> A compound corresponding to <N12> among any of the above <A1> to <M15>;
<O13> A compound corresponding to <N13> among any of the above <A1> to <M15>;
<O14> A compound corresponding to <N14> among any of the above <A1> to <M15>;
<O15> A compound corresponding to <N15> among any of the above <A1> to <M15>;
<O16> A compound corresponding to <N16> among any of the above <A1> to <M15>;
<O17> A compound corresponding to <N17> among any of the above <A1> to <M15>;
<O18> A compound corresponding to <N18> among any of the above <A1> to <M15>;
<O19> A compound corresponding to <N19> among any of the above <A1> to <M15>;
<O20> A compound corresponding to <N20> among any of the above <A1> to <M15>;
<O21> A compound corresponding to <N21> among any of the above <A1> to <M15>;
<O22> A compound corresponding to <N22> among any of the above <A1> to <M15>;
<O23> A compound corresponding to <N23> among any of the above <A1> to <M15>;
<O24> A compound corresponding to <N24> among any of the above <A1> to <M15>;
<O25> A compound corresponding to <N25> among any of the above <A1> to <M15>;
<O26> A compound corresponding to <N26> among any of the above <A1> to <M15>;
<O27> A compound corresponding to <N27> among any of the above <A1> to <M15>;
<O28> A compound corresponding to <N28> among any of the above <A1> to <M15>;
<O29> A compound corresponding to <N29> among any of the above <A1> to <M15>;
<O30> A compound corresponding to <N30> among any of the above <A1> to <M15>;
<O31> A compound corresponding to <N31> among any of the above <A1> to <M15>;
<O32> A compound corresponding to <N32> among any of the above <A1> to <M15>;
<O33> A compound corresponding to <N33> among any of the above <A1> to <M15>;
<O34> A compound corresponding to <N34> among any of the above <A1> to <M15>;
<O35> A compound corresponding to <N35> among any of the above <A1> to <M15>;
<O36> A compound corresponding to <N36> among any of the above <A1> to <M15>;
<O37> A compound corresponding to <N37> among any of the above <A1> to <M15>;
<O38> A compound corresponding to <N38> among any of the above <A1> to <M15>;
<O39> A compound corresponding to <N39> among any of the above <A1> to <M15>;
<O40> A compound corresponding to <N40> among any of the above <A1> to <M15>;
<O41> A compound corresponding to <N41> among any of the above <A1> to <M15>;
<O42> A compound corresponding to <N42> among any of the above <A1> to <M15>;
<O43> A compound corresponding to <N43> among any of the above <A1> to <M15>;
<O44> A compound corresponding to <N44> among any of the above <A1> to <M15>;
<O45> A compound corresponding to <N45> among any of the above <A1> to <M15>;
<O46> A compound corresponding to <N46> among any of the above <A1> to <M15>;
<O47> A compound corresponding to <N47> among any of the above <A1> to <M15>;
<O48> A compound corresponding to <N48> among any of the above <A1> to <M15>;
<P1> A compound in which $R^6$ is a hydrogen atom;
<P2> A compound in which $R^6$ is a hydroxy group;
<P3> A compound in which $R^6$ is a fluorine atom;
<P4> A compound in which $R^6$ is a chlorine atom;
<P5> A compound in which $R^6$ is a bromine atom;
<P6> A compound in which $R^6$ is a methyl group;
<P7> A compound in which $R^6$ is an ethyl group;
<P8> A compound in which $R^6$ is an n-propyl group;
<P9> A compound in which $R^6$ is an isopropyl group;
<P10> A compound in which $R^6$ is a trifluoromethyl group;
<P11> A compound in which $R^6$ is a methoxy group;
<P12> A compound in which $R^6$ is an ethoxy group;
<P13> A compound in which $R^6$ is an n-propoxy group;
<P14> A compound in which $R^6$ is an isopropoxy group;
<P15> A compound in $R^6$ is a trifluoromethyloxy group ;
<Q1> A compound corresponding to <P1> among any of the above <A1> to <O48>;
<Q2> A compound corresponding to <P2> among any of the above <A1> to <O48>;
<Q3> A compound corresponding to <P3> among any of the above <A1> to <O48>;
<Q4> A compound corresponding to <P4> among any of the above <A1> to <O48>;
<Q5> A compound corresponding to <P5> among any of the above <A1> to <O48>;
<Q6> A compound corresponding to <P6> among any of the above <A1> to <O48>;
<Q7> A compound corresponding to <P7> among any of the above <A1> to <O48>;
<Q8> A compound corresponding to <P8> among any of the above <A1> to <O48>;
<Q9> A compound corresponding to <P9> among any of the above <A1> to <O48>;
<Q10> A compound corresponding to <P10> among any of the above <A1> to <O48>;
<Q11> A compound corresponding to <P11> among any of the above <A1> to <O48>;
<Q12> A compound corresponding to <P12> among any of the above <A1> to <O48>;
<Q13> A compound corresponding to <P13> among any of the above <A1> to <O48>;
<Q14> A compound corresponding to <P14> among any of the above <A1> to <O48>;
<Q15> A compound corresponding to <P15> among any of the above <A1> to <O48>;
<R1> A compound in which $R^7$ is a hydrogen atom;
<R2> A compound in which $R^7$ is a hydroxy group;
<R3> A compound in which $R^7$ is a fluorine atom;
<R4> A compound in which $R^7$ is a chlorine atom;

<R5> A compound in which $R^6$ is a bromine atom;
<R6> A compound in which $R^7$ is a methyl group;
<R7> A compound in which $R^7$ is an ethyl group;
<R8> A compound in which $R^7$ is an n-propyl group;
<R9> A compound in which $R^7$ is an isopropyl group;
<R10> A compound in which $R^7$ is a trifluoromethyl group;
<R11> A compound in which $R^7$ is a methoxy group;
<R12> A compound in which $R^7$ is an ethoxy group;
<R13> A compound in which $R^7$ is an n-propoxy group;
<R14> A compound in which $R^7$ is an isopropoxy group;
<R15> A compound in $R^7$ is a trifluoromethyloxy group;
<S1> A compound corresponding to <R1> among any of the above <A1> to <Q15>;
<S2> A compound corresponding to <R2> among any of the above <A1> to <Q15>;
<S3> A compound corresponding to <R3> among any of the above <A1> to <Q15>;
<S4> A compound corresponding to <R4> among any of the above <A1> to <Q15>;
<S5> A compound corresponding to <R5> among any of the above <A1> to <Q15>;
<S6> A compound corresponding to <R6> among any of the above <A1> to <Q15>;
<S7> A compound corresponding to <R7> among any of the above <A1> to <Q15>;
<S8> A compound corresponding to <R8> among any of the above <A1> to <Q15>;
<S9> A compound corresponding to <R9> among any of the above <A1> to <Q15>;
<S10> A compound corresponding to <R10> among any of the above <A1> to <Q15>;
<S11> A compound corresponding to <R11> among any of the above <A1> to <Q15>;
<S12> A compound corresponding to <R12> among any of the above <A1> to <Q15>;
<S13> A compound corresponding to <R13> among any of the above <A1> to <Q15>;
<S14> A compound corresponding to <R14> among any of the above <A1> to <Q15>;
<S15> A compound corresponding to <R15> among any of the above <A1> to <Q15>;
<T1> A compound in which $R^9$ is a hydrogen atom;
<T2> A compound in which $R^9$ is a methyl group;
<T3> A compound in which $R^9$ is an ethyl group;
<U1> A compound corresponding to <T1> among any of the above <A1> to <S15>;
<U2> A compound corresponding to <T2> among any of the above <A1> to <S15>;
<U3> A compound corresponding to <T3> among any of the above <A1> to <S15>.

Compounds of the present invention are novel compound that have never been disclosed in any literature. Although the compounds of the present invention can be produced according to the method described below, for example, a method of preparing the compounds of the present invention is not limited thereto.

For each reaction, reaction time is not specifically limited. Since the progress of a reaction can be easily monitored using an analytical means described below, each reaction can be terminated when the amount of a target compound is highest. Further, each reaction may be carried out under inert gas atmosphere such as nitrogen stream or argon stream, etc., if required. Further, for each reaction, when protection using a protective group or subsequent deprotection is required, it can be appropriately carried out by using the methods described below.

Examples of a protective group which can be used for the present invention include a protective group for a carboxyl group (—OOH), a protective group for a hydroxy group (—OH), a protective group for a formyl group (—CHO—), a protective group for an amino group (—NH$_2$), and the like.

As for a protective group for a carboxyl group, for example, an alkyl group having 1 to 4 carbon atoms, an alkenyl group having 2 to 4 carbon atoms, an alkyl group having 1 to 4 carbon atoms substituted with an alkoxy group having 1 to 4 carbon atoms, an alkyl group having 1 to 4 carbon atoms substituted with 1 to 3 halogen atoms, etc. can be mentioned. Specific examples include a methyl group, an ethyl group, a t-butyl group, an allyl group, a methoxyethyl group, trichloroethyl group, and the like.

As for a protective group for a hydroxy group, for example, an alkyl group having 1 to 4 carbon atoms, an alkenyl group having 2 to 4 carbon atoms, an alkyl group having 1 to 4 carbon atoms substituted with an alkoxy group having 1 to 4 carbon atoms, an alkyl group having 1 to 4 carbon atoms substituted with 1 to 3 halogen atoms, a silyl group which is substituted with three different or the same phenyl groups or alkyl groups having 1 to 4 carbon atoms, a tetrahydropyranyl group, a tetrahydrofuryl group, a propargyl group, a trimethylsilylethyl group and the like can be mentioned. Specific examples include a methyl group, an ethyl group, a t-butyl group, an allyl group, a methoxymethyl (MOM) group, a methoxyethyl (MEM) group, a trichloroethyl group, a phenyl group, a methylphenyl group, a chlorophenyl group, a benzyl group, a methylbenzyl group, a chlorobenzyl group, a dichlorobenzyl group, a fluorobenzyl group, a trifluoromethylbenzyl group, a nitrobenzyl group, a methoxyphenyl group, an N-methylaminobenzyl group, an N,N-dimethylaminobenzyl group, a phenacyl group, a trityl group, a 1-ethoxyethyl (EE) group, a tetrahydropyranyl (THP) group, a tetrahydrofuryl group, a propargyl group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pyvaloyl group, a benzoyl group, an aryloxycarbonyl (Alloc) group, a 2,2,2-trichloroethoxycarbonyl (Troc) group and the like.

As for a protective group for a formyl group, an acetal group and the like can be mentioned, for example. Specifically, dimethylacetal and the like can be mentioned.

As for a protective group for an amino group, a benzyl group, a methylbenzyl group, a chlorobenzyl group, a dichlorobenzyl group, a fluorobenzyl group, a trifluoromethylbenzyl group, a nitrobenzyl group, a methoxyphenyl group, an N-methylaminobenzyl group, an N,N-dimethylaminobenzyl group, a phenacyl group, an acetyl group, a trifluoroacetyl group, a pivaloyl group, a benzoyl group, an allyloxycarbonyl group, a 2,2,2-trichloroethoxycarbonyl group, a benzyloxycarbonyl group, a t-butoxycarbonyl (Boc) group, a 1-methyl-1-(4-biphenyl)ethoxycarbonyl (Bpoc) group, a 9-fluorenylmethoxycarbonyl group, a benzyloxymethyl (BOM) group, and a 2-(trimethylsilyl)ethoxymethyl (SEM) group, etc. can be mentioned.

A protective group can be deprotected simultaneously or sequentially during an intermediate step or a final step of a production process, and can be converted accordingly to a desired product. A process for protection and deprotection can be carried out according to a known method, for example, a method described in "Protective Groups in Organic Synthesis, Fourth Edition, 2007, John Wiley & Sons, Inc." It can be carried out according to the methods (1) to (6) described below, for example.

(1) Deprotection reaction based on alkali hydrolysis is carried out, for example, by the reaction with a base in a polar solvent. Examples of a base include, for example, an alkali metal base such as sodium hydroxide, potassium hydroxide, lithium hydroxide, barium hydroxide, calcium hydroxide, sodium carbonate, potassium carbonate, sodium methoxide, potassium t-butoxide, and an organic base such as triethyl amine. Use amount of these bases is generally 1 to 20 times, preferably 1 to 10 times the molar amount of a reaction compound for an alkali metal base, and 1 mole to excess molar amount for an organic base, for example. The reaction solvent is generally an inert medium which does not interfere a reaction. Preferably, the reaction is carried out in a polar solvent. Examples of the polar solvent include water, methanol, ethanol, tetrahydrofuran, dioxane and the like. A mixture thereof can be also used, if necessary. The reaction temperature is appropriately chosen between −10° C. to reflux temperature of a solvent, for example. The reaction time is generally between 0.5 to 72 hours, preferably 1 to 48 hours, for example, when an alkali metal base is used. When an organic base is used, it is generally 5 hours to 14 days, for example. Since the progress of reaction can be monitored by thin layer chromatography (TLC), high performance liquid chromatography (HPLC), etc., the reaction can be generally terminated when the amount of a target compound is highest.

(2) Deprotection reaction under acidic condition is carried out, for example, in an organic solvent such as dichloromethane, chloroform, dioxane, ethyl acetate, or anisole. in the presence of an organic acid such as acetic acid, trifluoroacetic acid, methanesulfonic acid, p-toluenesulfonic acid, Lewis acid such as boron tribromide, boron trifluoride, aluminum bromide, or aluminum chloride, or an inorganic acid such as hydrochloric acid, or sulfuric acid or a mixture thereof such as hydrogen bromide or acetic acid at the temperature of −10 to 100° C. In addition, there is another method in which ethanethiol, 1,2-ethanedithiol, etc. are added as an additive.

(3) Deprotection reaction based on hydrogenation can be carried out, for example, in an ether solvent such as tetrahydrofuran, dioxane, dimethoxy ethane, or diethyl ether, an alcohol solvent such as methanol, or ethanol, a benzene type solvent such as benzene, or toluene, a ketone solvent such as acetone, or methyl ethyl ketone, a nitrile solvent such as acetonitrile, an amide solvent such as dimethylformamide, an ester solvent such as ethyl acetate, water, acetic acid, or a mixed solvent including two or more of them in the presence of a catalyst such as carbon palladium powder, platinum oxide (PtO$_2$), or activated nickel and a hydrogen source such as atmospheric or pressurized hydrogen gas, ammonium formic acid, or hydrazine hydrate at the temperature of −10 to 60° C.

(4) Deprotection reaction of a silyl group is carried out, for example, by using tetra-n-butyl ammonium fluoride and the like in an organic solvent which is miscible with water (e.g., tetrahydrofuran, acetonitrile and the like) at the temperature of −10 to 60° C.

(5) Deprotection reaction using a metal is carried out in an acidic solvent, for example, in acetic acid, a buffer solution having pH 4.2 to 7.2, or a mixed solvent including them and an organic solvent such as tetrahydrofuran and the like, in the presence of zinc powder with or without ultrasonication at the temperature of −10 to 60° C.

(6) Deprotection reaction using a metal complex is carried out, for example, in an organic solvent such as dichloromethane, dimethylformamide, tetrahydrofuran, ethyl acetate, acetonitrile, dioxane, or ethanol, water, or a mixed solvent thereof, in the presence of a trapping agent such as tributyl tin hydride, triethyl silane, dimedone, morpholine, diethylamine, or pyrrolidine, an organic acid such as acetic acid, formic acid, or 2-ethyl hexanoic acid and/or an organic acid salt such as sodium 2-ethyl hexanoate, or potassium 2-ethyl hexanoate, with or without a phosphine reagent such as triphenyl phosphine by using a metal complex such as tetrakis triphenyl phosphine palladium (0), dichlorobis (triphenylphosphine)palladium (II), palladium (II) acetate, or chlorotris(triphenylphosphine)rhodium (I), at the temperature of −10 to 60° C.

The compounds represented by the formula (1) of the present invention can be prepared according to a retrosynthetic pathway according to the following reaction, for example.

[Chemical Formula 6]

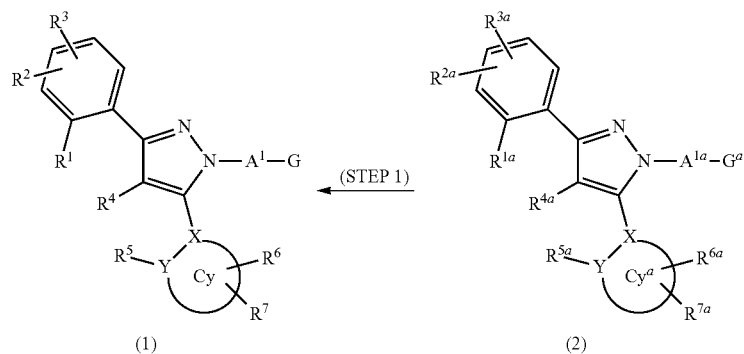

For example, the compounds represented by the formula (1) can be prepared by simultaneously or sequentially deprotecting all the protective groups of the compounds represented by the formula (2) [in the formula (2), $R^{1a}$, $R^{2a}$, $R^{3a}$, $R^{4a}$, $R^{5a}$, $R^{6a}$, $R^{7a}$, $Cy^a$, $A^{1a}$ and $G^a$ have the same meanings as $R^1$, $R^2$, $R^3$, $R^4$, $R^5$, $R^6$, $R^7$, Cy, $A^1$ and G described above, respectively (with the proviso that, the formula which corresponds to the general formulas ($G^1$) to ($G^4$) of G, i.e., the general formula of $G^a$ is represented as ($G^{1a}$) to ($G^{4a}$), and the symbols which correspond to $A^2$, $R^8$ and $R^9$ of the formulas ($G^1$) to ($G^4$) are $A^{2a}$, $R^{8a}$ and $R^{9a}$, respectively, in the formulas ($G^{1a}$) to ($G^{4a}$)) or at least one of these groups may be protected. X and Y are as defined in the above.]. A deprotection reaction can be carried out according to a known method, for example, a method described in "Protective Groups in Organic Synthesis, 2007, John Wiley & Sons, Inc." Further, when $R^{1a}$, $R^{2a}$, $R^{3a}$, $R^{4a}$, $R^{5a}$, $R^{6a}$, $R^{7a}$, $Cy^a$, $A^{1a}$ and $G^a$ in the formula (2) have the same meaning as $R^1$, $R^2$, $R^3$, $R^4$, $R^5$, $R^6$, $R^7$, Cy, $A^1$ and G described above, the compounds represented by the formula (2) correspond to the compounds represented by the formula (1) without requiring any deprotection.

The compounds represented by the formula (2A) [in the formula (2A), $R^{1a}$, $R^{2a}$, $R^{3a}$, $R^{4a}$, $R^{5a}$, $R^{6a}$, $R^{7a}$, $A^{1a}$, $G^a$, X and Y are as defined in the above.], i.e., the compounds of the formula (2) in which $Cy^a$ is an aryl group, can be prepared according to a retrosynthetic pathway according to the following reaction, for example.

N-dimethylcyclohexane-1,2-diamine, (1S, 2S)-(+)-1,2-cyclohexanediamine, (1R, 2R)-(−)-1,2-cyclohexanediamine, 1,10-phenanthroline, 2,9-dimethyl-1,10-phenanthroline, 4,7-dimethyl-1,10-phenanthroline, 3,4,7,8-tetramethyl-1,10-phenanthroline, 2,2,6,6-tetramethyl-3,5-heptanedione, 2-acetylcyclohexanone, 2-propionylcyclohexanone, N,N-diethylsalicylamide, N-methylethylenediamine, N,N-dimethylethylenediamine, N,N'-dimethylethylenediamine, N,N,N',

[Chemical Formula 7]

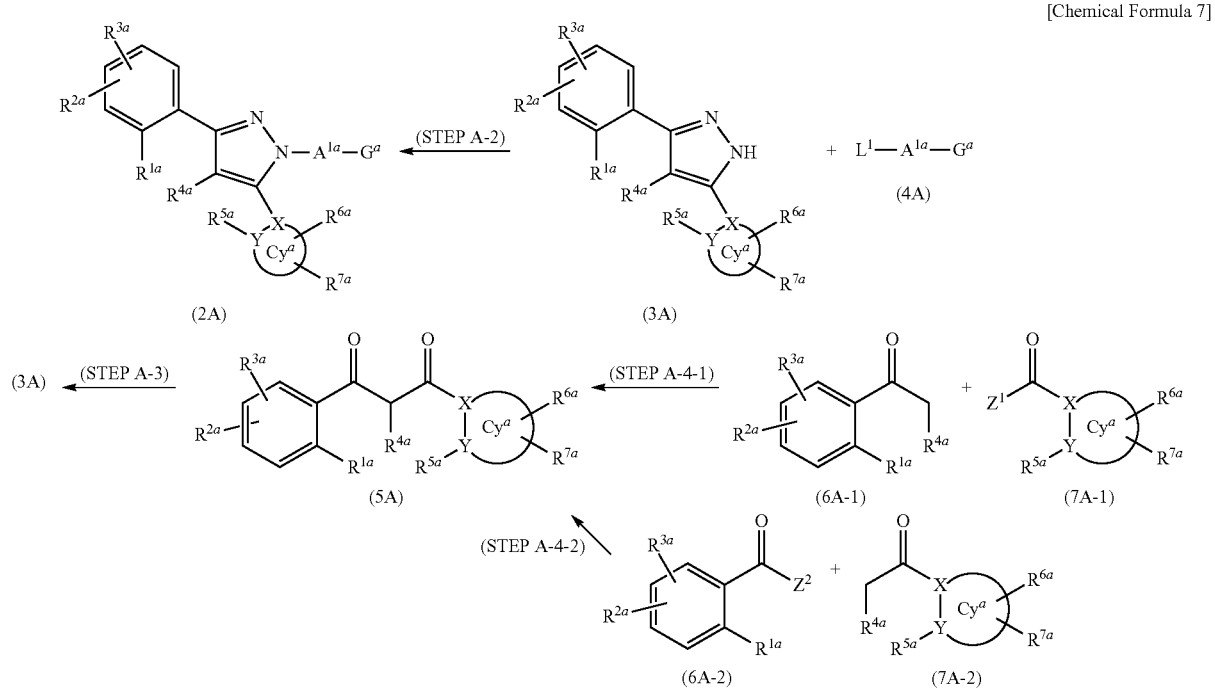

Among the compounds represented by the formula (2A), the compounds in which $A^{1a}$ is a single bond or an alkenylene group which may be substituted can be prepared by reacting the compounds represented by the formula (3A) [in the formula (3A), $R^{1a}$, $R^{2a}$, $R^{3a}$, $R^{4a}$, $R^{5a}$, $R^{6a}$, $R^{7a}$, $Cy^a$, X and Y are as defined in the above.] with the compounds represented by the formula (4A) [in the formula (4A), $A^{1a}$ and $G^a$ are as defined in the above, and $L^1$ is a chlorine atom, a bromine atom or an iodine atom.] by using a commercially available copper catalyst or a catalyst obtained from copper powder or copper salt and a ligand compound in the presence of a base. For the reaction of the compounds represented by the formula (3A) and the compounds represented by the formula (4A), the compounds represented by the formula (4A) can be used in an amount of ⅕ to 20 equivalents compared to the compounds represented by the formula (3A). It can be also ½ to 10 equivalents, and preferably is 1 to 5 equivalents. However, depending on purity, yield, and purification efficiency. of the compounds represented by the formula (2A), it can be appropriately selected. As a copper catalyst, a commercially available catalyst such as bis(acetylacetonate) copper (II) can be directly added to a reaction system or a catalyst obtained by mixing copper powder, copper (I) chloride, copper (I) bromide, copper (I) iodide, copper (I) cyanide, copper (I) oxide, copper (II) chloride, copper (II) bromide, copper (II) acetate, copper (II) sulfate, or copper (II) oxide and a ligand compound can be used. Examples of a ligand include (1S, 2S)-(+)-N,N-dimethylcyclohexane-1,2-diamine, (1R, 2R)-(−)-N, N'-tetramethylethylenediamine, 8-quinolinol, 1,1'-binaphthyl-2,2'-diol, 2,2'-dihydroxybiphenyl, catechol, ethylene glycol, 9,10-phenanthrene quinone, L-(−)-proline, D-(+)-proline, glycine and the like. Preferably, copper (I) iodide is used with (1S, 2S)-(+)-N,N-dimethylcyclohexane-1,2-diamine as a ligand. The copper catalyst is used in an amount of 1/1000 to 1 equivalent compared to the compounds of the formula (2A). It can be 1/500 to ½ equivalents, and preferably is 1/100 to ⅕ equivalents. Examples of a base include lithium hydroxide, sodium hydroxide, potassium hydroxide, sodium carbonate, potassium carbonate, cesium carbonate, cesium fluoride, potassium fluoride, potassium phosphate, potassium acetate and the like. Preferably, it is potassium phosphate or cesium carbonate. The base can be used in an amount of 1/20 to 20 equivalents compared to the compounds of the formula (2A). It can be 1/10 to 10 equivalents, and preferably is ½ to 5 equivalents. Examples of a solvent which can be used for the reaction include N,N-dimethylformamide, N,N-dimethylacetamide, N-methyl-2-pyrrolidone, toluene, xylene, mesitylene, 1,4-dioxane, tetrahydrofuran or dimethyl sulfoxide. Preferably, it is N,N-dimethylacetamide or mesitylene. Further, these solvents can be used as a mixture including two or more of them. Still further, these solvents can be mixed with water and then used. In general, the reaction can be carried out in the temperature range of 20° C. to 250° C. Preferably, it is in the temperature range of 80° C. to 200° C. Reaction time is not specifically limited. In general, it is in the range of 4 hours to 72 hours, preferably in the range of 8 to 48 hours Among the compounds represented by the formula (2A), the compounds in which $A^{1a}$ is an alkylene group which may be substituted can be prepared by reacting the compounds represented by the formula (3A) [in the formula (3A), $R^{1a}$, $R^{2a}$, $R^{3a}$, $R^{4a}$, $R^{5a}$, $R^{6a}$, $R^{7a}$, $Cy^a$, $G^a$, X and Y are as defined in the above.] with the compounds represented by the formula (4A) [in the formula (4A), $A^{1a}$, $G^a$ and $L^1$ are as defined in the above.] in the presence of a base. For the reaction of the compounds represented by the formula (3A) and the compounds represented by the formula (4A), the compounds represented by the formula (4A) can be used in an amount of ⅕ to 20 equivalents compared to the compounds represented by the formula (3A). It can be also ½ to 10 equivalents, and preferably is 1 to 5 equivalents. However, depending on purity, yield, and purification efficiency, etc. of the compounds represented by the formula (2A), it can be appropriately selected. Examples of a base include sodium hydride, potassium hydride, sodium ethoxide, potassium-t-butoxide, sodium carbonate, potassium carbonate and the like. Preferably, it is sodium hydride. The base can be used in an amount of one equivalent to an excess amount compared to the compounds of the formula (3A) as a reacting material. It can be 1 to 10 equivalents, and preferably is 1 to 5 equivalents. Examples of a solvent which can be used for the reaction include N,N-dimethylformamide, N,N-dimethylacetamide, xylene, toluene, 1,4-dioxane, tetrahydrofuran and the like. N,N-dimethylformamide or N,N-dimethylacetamide is preferable. Further, these solvents can be used as a mixture including two or more of them. In general, the reaction can be carried out in the temperature range of −40° C. to 100° C. Preferably, it is in the temperature range of −20° C. to 60° C. Reaction time is not specifically limited. In general, it is in the range of 0.5 hours to 48 hours, preferably in the range of 1 to 24 hours.

Among the compounds represented by the formula (2A), the compounds in which $R^{4a}$ is an alkoxy group which may be substituted or an alkoxy group which is substituted with a substituent having at least one protective group can be prepared by reacting, if necessary in the presence of a base, the compounds represented by the formula (2A) in which $R^{4a}$ is a hydroxy group with an alkylating agent having an alkyl group which may be substituted or an alkyl group which is substituted with a substituent having at least one protective group. Examples of an alkylating agent include a halide of an alkyl group which may be substituted or a halide of an alkyl group which is substituted with a substituent having at least one protective group, etc. Specific examples include alkyl iodide, alkyl bromide, alkyl chloride and the like. In addition, an alkylating agent which has leaving groups other than halide, such as mesylate, or tosylate, triflate is also useful. The alkylating agent can be used in an amount of one equivalent to an excess amount compared to the compounds of the formula (2A). It can be 1 to 10 equivalents, and preferably is 1 to 5 equivalents. If necessary, a base can be used for the reaction. Any of an organic or an inorganic base can be used. Examples include sodium hydride, potassium hydride, sodium hydroxide, potassium hydroxide, potassium carbonate, sodium carbonate, triethylamine, diisopropylethylamine, N-methylmorpholine, pyridine and the like. The base can be used in an equivalent amount or an excess amount compared to the compounds of the formula (2A). It can be 1 to 100 equivalents, and preferably is 1 to 30 equivalents. As for the solvent which is used for the reaction, an inert solvent can be used. Examples of an inert solvent include dichloromethane, chloroform, 1,2-dichloroethane, tetrahydrofuran, 1,4-dioxane, dimethoxyethane, N,N-dimethylformamide, N,N-dimethylacetamide and the like. Preferably, it is tetrahydrofuran or N,N-dimethylformamide. Further, these solvents can be used as a mixture including two or more of them. In general, the reaction can be carried out in the temperature range of −20° C. to 100° C. Preferably, it is in the temperature range of −10° C. to 50° C. Reaction time is not specifically limited. In general, it is in the range of 0.2 hours to 24 hours, preferably in the range of 1 to 5 hours. Further, according to other embodiment, among the compounds represented by the formula (2A), the compounds in which $R^{4a}$ is hydroxy group can be reacted with an alkyl alcohol in the presence of a phosphorous reagent and an azo compound in an inert solvent (see, Chem. Lett., 539-542 (1994) or Synthesis, 1 (1981), etc.). Examples of an inert solvent include tetrahydrofuran, dioxane, toluene, dichloromethane and the like. Tetrahydrofuran or dichloromethane is preferable. Further, these solvents can be used as a mixture including two or more of them. Examples of a phosphorus reagent include triphenyl phosphine, tributyl phosphine and the like. Examples of an azo compound include diethyl azodicarboxylate, diisopropyl azodicarboxylate, N,N,N',N'-tetramethyl azodicarbonamide and the like.

Among the compounds represented by the formula (2A), the compounds in which $R^{4a}$ of the formula (2A) is a chlorine atom, a bromine atom or an iodine atom can be prepared by reacting the compounds represented by the formula (2A) in which $R^{4a}$ is an amino group with salts and ester of nitrous acid followed by reaction with a metal halide compound or a halogen molecule. This reaction is carried out according to a known method. A preferable example includes that, the compounds in which $R^{4a}$ of the formula (2A) is an amino group are reacted with ester of nitrous acid in an organic solvent followed by reaction with a metal halide compound for halogenation. Examples of an ester of nitrous acid include t-butyl nitrous acid or isoamyl nitrous acid and the like. The ester of nitrous acid can be used in an amount of ⅕ to 20 equivalents compared to the compounds of the formula (2A) in which $R^{4a}$ is an amino group. Preferably, it is ½ to 10 equivalents, and more preferably is 1 to 5 equivalents. When a metal halide compound is used, it is preferably selected depending on the halogen atom represented by $R^{4a}$ in the compounds of the formula (2A). Specifically, when R is a chlorine atom, copper chloride or potassium chloride is preferably used. When $R^{4a}$ is a bromine atom, copper bromide or potassium bromide is preferably used. When $R^{4a}$ is an iodine atom, copper iodide or potassium iodide is preferably used. The metal halide can be used in an amount of ⅕ to 50 equivalents compared to the compounds of the formula (2A) in which $R^{4a}$ is an amino group. Preferably, it is ½ to 20 equivalents, and more preferably is 1 to 10 equivalents. As for the solvent which is used for the reaction, 1,4-dioxane, tetrahydrofuran or acetonitrile can be used. Preferably, it is acetonitrile. Further, these solvents can be used as a mixture including two or more of them. In general, the reaction can be carried out in the temperature range of 0° C. to reflux temperature of a solvent. Preferably, it is in the temperature range of 20° C. to 80° C. Reaction time is not specifically limited. In general, it is in the range of 0.5 hours to 24 hours, preferably in the range of 1 to 12 hours. Further, according to other embodiment, there is other preferable method in which salt of nitrous acid is reacted in an aqueous acid solution followed by reaction with metal halide for halogenation. Examples of an aqueous acid solution include sulfuric acid, hydrochloric acid, hydrogen bromide acid and the like. Examples of salts of nitrous acid include sodium nitrite and the like. When a metal halide is used, a metal halide which includes the halogen atom included in $R^{4a}$ of the desired formula (2A) can be used.

Furthermore, among the compounds of the Formula (2A), the compounds in which $R^{4a}$ of the Formula (2A) is —CF$_3$ can be prepared according to a method described in general chemical literatures, e.g., a method described at pages 292-300 of Organo Fluorine Chemistry (Kenji Uneyama, published by Blackwell), or a method described in the references cited in the literature. As an appropriate example, by reacting a compound of the Formula (2A) in which $R^{4a}$ is a chlorine atom, a bromine atom or an iodine atom with a reagent for trifluoromethylation in the presence of a catalyst in an inert solvent, the compounds in which $R^{4a}$ of the Formula (2A) is —$CF_3$ can be prepared. As an inert solvent, an aprotic solvent such as N,N-dimethylformamide, N,N-dimethylacetamide, dimethyl sulfoxide or N-methylpyrrolidone can be mentioned. N-Methylpyrrolidone is preferred. As a reagent for trifluoromethylation, trifluoromethyl iodide, sodium trifluoroacetate, methyl 2,2-difluoro-2-(fluorosulfonyl)acetate, trifluoromethyl-trimethyl silane, trifluoromethyl-triethylsilane or methyl chlorodifluoroacetate-potassium fluoride and the like can be mentioned. Methyl 2,2-difluoro-2-(fluorosulfonyl)acetate is preferred. As a catalyst, a copper complex, a copper salt such as copper iodide or copper bromide, etc. or copper powder can be mentioned. Copper iodide is preferred.

The reagent for trifluoromethylation can be used in an amount of 1- to 10-fold moles, preferably 1- to 5-fold moles relative to the compound of the Formula (2A) in which $R^{4a}$ is a chlorine atom, a bromine atom or an iodine atom. The catalyst is used in an amount of 0.001- to 10-fold moles, preferably 0.1- to 5-fold moles relative to the compound of the Formula (2A) in which $R^{4a}$ is a chlorine atom, a bromine atom or an iodine atom. The reaction temperature is 0° C. to reflux under heating. It is preferably 60° C. to reflux under heating. The reaction time is 0.1 to 48 hours and preferably 1 to 24 hours.

Furthermore, among the compounds represented by the Formula (2A), the compounds in which $R^{4a}$ in the Formula (2A) is —$N(R^{P1})(R^{P2})$ ($R^{P1}$ and $R^{P2}$ can be the same or different to each other, and each independently represent a hydrogen atom, an alkyl group which may be substituted or an aryl group which may be substituted, or $R^{P1}$ and $R^{P2}$ together form a 3- to 7-membered ring to represent a cyclic amine of $N(R^{P1})(R^{P2})$.) can be prepared by subjecting the compounds represented by the Formula (2A) in which $R^{4a}$ is an amino group to a reductive amination reaction for coupling to an aldehyde or a ketone. With respect to a reductive amination, a method described in the literature, i.e., "Reductive Amination Reaction" in Lectures on Experimental Science, edited by The Chemical Society of Japan, Vol. 20, page 300, 1992, published by Maruzen, or a method described in the references cited in the literature can be mentioned. The corresponding aldehyde or ketone is used in an amount of ⅕ equivalents to 20 equivalents, preferably ½ to 10 equivalents, relative to the compounds of the Formula (2) in which $R^{3a}$ and/or $R^{4a}$ is —$N(R^{Q1})(R^{Q2})$ ($R^{Q1}$ and $R^{Q2}$ are as defined above, or may be protected with a substituent having at least one protective group, with the proviso that at least one group of $R^{Q1}$ and $R^{Q2}$ is a hydrogen atom.). More preferably, it is used in an amount of 1 to 5 equivalents. As a reducing agent, a metal hydride reducing agent such as sodium borohydride, sodium cyanoborohydride, sodium borohydride triacetate, a borane-dimethyl sulfide complex, a borane-pyridine complex, a borane-triethylamine complex, a borane-tetrahydrofuran complex, lithium triethylboron and the like can be mentioned. Preferably, sodium cyanoborohydride or sodium borohydride triacetate can be mentioned. The reducing agent is used in an amount of at least 1/10 equivalents, preferably 1 to 20 equivalents, relative to the compounds of the Formula (2A) in which $R^{4a}$ is an amino group. As an acid to be added, acetic acid and trifluoroacetic acid can be mentioned. Acetic acid is preferred. The acid is used in an amount of 1/10 equivalents to 20 equivalents, preferably ⅕ to 10 equivalents, relative to the compounds of the Formula (2A) in which $R^{4a}$ is an amino group. Examples of a solvent include methanol, ethanol, isopropanol, tetrahydrofuran, 1,2-dimethoxyethane, 1,4-dioxane, dichloromethane, chloroform, 1,2-dichloroethane, N,N-dimethylformamide and the like. Preferably, it is methanol, tetrahydrofuran or dichloromethane. The reaction temperature is at least 0° C. It is preferably 10° C. to reflux temperature of a solvent. The reaction time is at least 0.1 hours and preferably 0.5 to 30 hours.

The compounds represented by the formula (3A) can be prepared by reacting the compounds represented by the formula (5A) [in the formula (5A), $R^{1a}$, $R^{2a}$, $R^{3a}$, $R^{4a}$, $R^{5a}$, $R^{6a}$, $R^{7a}$, $Cy^a$, X and Y are as defined in the above.] with hydrazine. The reaction can be carried out according to the method described in the literature (for example, J. Heterocycl. Chem., 18, 803-805 (1981)). Hydrazine can be either hydrazine hydrate or anhydrous hydrazine. Preferably, it is hydrazine hydrate. Hydrazine can be used in an amount of ⅕ to 20 equivalents compared to the compounds represented by the formula (5A). It can be also ½ to 10 equivalents, and preferably is 1 to 5 equivalents. However, depending on purity, yield, and purification efficiency, etc. of the compounds represented by the formula (3A), it can be appropriately selected. As for the solvent which is used for the reaction, methanol, ethanol, isopropyl alcohol, 2-methyl-2-propanol, N,N-dimethylformamide, toluene, 1,4-dioxane, tetrahydrofuran, or acetic acid can be used. Preferably, it is ethanol, isopropyl alcohol or acetic acid. Further, these solvents can be used as a mixture including two or more of them. In general, the reaction can be carried out at appropriate temperature in the temperature range of 0° C. to reflux temperature of a solvent. Reaction time is not specifically limited. In general, it is in the range of 0.2 hours to 24 hours, preferably in the range of 0.5 to 12 hours.

As for the compound of the formula (4A) in which $A^{1a}$ is a single bond, commercially available ethyl 2-bromothiazole-4-carboxylic acid (manufactured by Combi-Block), methyl 2-bromothiazole-4-carboxylic acid (manufactured by Combi-Block), ethyl 2-bromothiophene carboxylic acid (manufactured by Alfa Aesar Co.), methyl 6-bromo-2-pyridine carboxylic acid (manufactured by Aldrich Company), methyl 5-bromo-2-pyridine carboxylic acid (manufactured by Combi-Block) and the like can be used. Alternatively, a compound in which $L^1$ is an amino group is reacted with an ester of nitrous acid in an organic solvent according to a known method (see, J. Org. Chem., 61, 4623-4633 (1996) or Tetrahedron: Asymmetry, 9, 1395-1408 (1998)) followed by reaction with metal halide, and then the resulting compound can be used.

Among the compounds represented by the formula (4A), the compounds in which $A^{1a}$ is a single bond, $L^1$ is an amino group and $R^{9a}$ is an alkyl group which may be substituted can be prepared by reacting the compounds represented by the formula (4A) in which $A^{1a}$ is a single bond, $L^1$ is an amino group and $R^{9a}$ is a bromine atom or an iodine atom with a commercially available tin reagent that is represented by the formula (8A): $(R^{9a})_4Sn$ [in the formula (8A), $R^{9a}$ is an alkyl group which may be substituted.] by using a commercially available palladium catalyst or a catalyst which is obtained from a palladium complex and a ligand. Among the compounds represented by the formula (4A), when the compounds in which $A^{1a}$ is a single bond, $L^1$ is an amino group and $R^{9a}$ is a bromine atom or an iodine atom are reacted with the compounds represented by the formula (8A), the compounds of the formula (8A) can be used in an amount of ⅕ to 20 equivalents compared to the compounds represented by the formula (4A) in which $A^{1a}$ is a single bond, $L^1$ is an amino group and $R^{9a}$ is a bromine atom or an iodine atom. Preferably, it is ½ to 10 equivalents, and more preferably is 1 to 5 equivalents. However, depending on purity, yield, and purification efficiency, etc. of the compounds represented by the formula (4A) in which $A^{1a}$ is a single bond, $L^1$ is an amino group and $R^{9a}$ is an alkyl group which may be substituted, it can be appropriately selected. As for the palladium catalyst, a commercially available catalyst such as tris(dibenzylideneacetone) dipalladium, dibenzylideneacetone palladium, tetrakis triphenyl phosphine palladium, or palladium acetate can be directly added to a reaction system, or a catalyst which is obtained by mixing palladium acetate or dibenzylideneacetone palladium with any ligand can be used. Examples of a ligand include triphenyl phosphine, tri-t-butyl phosphine, tricyclohexyl phosphine or 2-(di-t-butylphosphino)biphenyl and the like. Preferably, tetrakis triphenyl phosphine palladium is used without being mixed with any ligand. The catalyst is preferably used in an amount of 1/1000 to 1 equivalent compared to the compounds represented by the formula (4A) in which $A^{1a}$ is a single bond, $L^1$ is an amino group and $R^{9a}$ is a bromine atom or an iodine atom. It can be used in an amount of 1/100 to 1/2 equivalents, and more preferably is 1/100 to 1/5 equivalents. Examples of the solvent which can be used for the reaction include N,N-dimethylformamide, N,N-dimethylacetamide, xylene, toluene, 1,4-dioxane, tetrahydrofuran, ethanol or methanol, and N,N-dimethylformamide or 1,4-dioxane is preferred. Further, these solvents can be used as a mixture including two or more of them. In general, the reaction can be carried out at appropriate temperature in the temperature range of 0° C. to 150° C. Preferably, it is in the range of 40° C. to 120° C. Reaction time is not specifically limited. In general, it is in the range of 1 hour to 72 hours, preferably in the range of 2 to 24 hours.

As for the compound of the formula (4A) in which $A^{1a}$ is a single bond, $L^1$ is an amino group and $R^{9a}$ is a bromine atom or an iodine atom, commercially available methyl 2-amino-5-bromothiazole-4-carboxylic acid (manufactured by Combi-Block), or methyl 6-amino-3-bromo-2-picolinic acid (manufactured by Combi-Block) and the like can be used.

As for the compounds of the formula (4A) in which $A^{1a}$ is a methylene group which may be substituted, a compound prepared according to a known method, e.g., Liebigs. Ann. Chem., 4, 623-632 (1981), etc., can be used.

Among the compounds represented by the formula (4A), the compounds of the formula (4AA) in which $A^{1a}$ is an ethenylene group [in the formula (4AA), $G^a$ is as defined in the above, $L^1$ is a chlorine atom, a bromine atom or an iodine atom, and stereochemistry relating to a double bond of the ethenylene group represented by $A^1$ can be any of cis and trans.] can be prepared according to a retrosynthetic pathway according to the following reaction, for example.

represented by the formula (9AA). It can be an amount of 1/2 to 10 equivalents, for example, and preferably is 1 to 5 equivalents. As for the halogen atom source used for the reaction, a halogen molecule or N-halogenated succinimide which includes the halogen atom represented by $L^1$ in the desired formula (4AA) can be used. Specifically, when $L^1$ is a chlorine atom, N-chlorosuccinimide is preferably used. When $L^1$ is a bromine atom, bromine molecule or N-bromosuccinimide is preferably used. When $L^1$ is an iodine atom, iodine molecule or N-iodosuccinimide is preferably used. The halogen atom source can be used in an amount of 1/5 to 20 equivalents compared to the compounds represented by the formula (9AA). It can be an amount of 1/2 to 10 equivalents, for example, and preferably is 1 to 5 equivalents. Examples of a solvent which can be used for the reaction include N,N-dimethylformamide, toluene, 1,4-dioxane, tetrahydrofuran and the like, and tetrahydrofuran is preferred. Further, these solvents can be used as a mixture including two or more of them. In general, the reaction can be carried out at appropriate temperature in the temperature range of −60° C. to 60° C. Preferably, it is in the range of −20° C. to 40° C. Reaction time is not specifically limited. In general, it is in the range of 0.2 hour to 24 hours, preferably in the range of 0.5 to 12 hours.

The compounds represented by the formula (9AA) can be prepared from the compounds represented by the formula (10AA) [in the formula (10AA), $G^a$ is as defined in the above.] under a known condition for deprotection of a silyl group. For example, a reaction in which tetrabutyl ammonium fluoride is used in a water-soluble ether solvent such as tetrahydrofuran can be mentioned. Tetrabutyl ammonium fluoride can be used in an amount of 1/2 to 20 equivalents compared to the compounds represented by the formula (10AA) and preferably is 1 to 10 equivalents. Examples of the solvent which can be used for the reaction include N,N-dimethylformamide, toluene, 1,4-dioxane, tetrahydrofuran, dichloromethane, chloroform and the like, and tetrahydrofuran or dichloromethane is preferred. Further, these solvents can be used as a mixture including two or more of them. In general, the reaction can be carried out at appropriate temperature in the temperature range of −20° C. to 100° C. Preferably, it is in the range of 0° C. to 60° C. Reaction time is not specifically limited. In general, it is in the range of 0.2 hour to 24 hours, preferably in the range of 0.5 to 12 hours.

The compounds represented by the formula (10AA) can be prepared by reacting the compounds represented by the formula (4AB) [in the formula (4AB), $G^a$ and $L^1$ are as defined

[Chemical Formula 8]

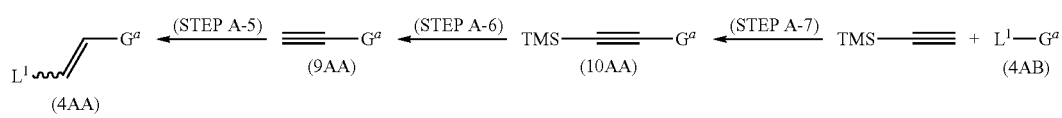

The compounds represented by the formula (4AA) can be prepared by reacting the compounds represented by the formula (9AA) [in the formula (9AA), $G^a$ is as defined in the above.] with metal hydride species followed by reaction with a corresponding halogen atom source. Types of a metal halide species include, for example, borane-tetrahydrofuran complex, 9-borabicyclo[3.3.1]nonane, dibromoborane-dimethylsulfide complex, catechol borane, diisobutyl aluminum, tributyl tin, bis(cyclopentadienyl)zirconium (IV) chloride hydride and the like. The metal halide species can be used in an amount of 1/5 to 20 equivalents compared to the compounds in the above.], i.e., the compounds represented by the formula (4A) in which $A^{1a}$ is a single bond, with trimethyl silylacetylene by using a commercially available palladium catalyst or a catalyst which is obtained from a palladium complex and a ligand in the presence of a base. For the reaction between the compounds represented by the formula (10AA) and trimethyl silylacetylene, trimethyl silylacetylene can be used in an amount of 1/2 to 10 equivalents compared to the compounds represented by the formula (4AB), and preferably it is 1 to 5 equivalents. As for the palladium catalyst, a commercially available catalyst such as tris(dibenzylideneacetone)dipalladium, dibenzylideneacetone palladium, tetrakis triphenylphosphine palladium, dichlorobis (triphenylphosphine) palladium, palladium acetate, palladium chloride and the like can be directly added to a reaction system, or a catalyst which is obtained by mixing palladium acetate, dibenzylideneacetone palladium, or dichlorobis(triphenylphosphine)palladium with any ligand can be used. Examples of a ligand include triphenyl phosphine, tri-t-butyl phosphine, tricyclohexyl phosphine or 2-(di-t-butylphosphino)biphenyl and the like. Preferably, dichlorobis(triphenylphosphine) palladium is used with triphenyl phosphine as a ligand. The palladium catalyst is preferably used in an amount of 1/1000 to 1 equivalent compared to the compounds represented by the formula (4AB). It can be used in an amount of 1/100 to ½ equivalents, and more preferably is 1/100 to 1/5 equivalents. Examples of a base include triethylamine, diethylamine, diisopropylamine, sodium acetate, sodium hydroxide, lithium hydroxide, potassium fluoride, potassium carbonate, cesium carbonate, cesium fluoride, sodium t-butoxide and the like. Preferably, it is triethylamine or diethylamine. The base can be used in an amount of 1/10 to 10 equivalents compared to the compounds of the formula (4AB). Preferably, it is 1/5 to 5 equivalents. Solvents that are used for the reaction include N,N-dimethylformamide, N,N-dimethylacetamide, xylene, toluene, 1,4-dioxane, tetrahydrofuran, ethanol, methanol and the like. Preferably, it is N,N-dimethylformamide or 1,4-dioxane. Further, these solvents can be used as a mixture including two or more of them. In general, the reaction can be carried out at appropriate temperature in the temperature range of 0° C. to 150° C. Preferably, it is in the range of 40° C. to 120° C. Reaction time is not specifically limited. In general, it is in the range of 1 hour to 72 hours, preferably in the range of 2 to 24 hours.

As for the compounds represented by the formula (5A), commercially available 1,3-diphenyl-1,3-propanedione (manufactured by Aldrich Company) or 1-(2-hydroxyphenyl)-3-phenyl-1,3-propanedione (manufactured by Aldrich Company), etc. can be used, or a product obtained by reaction between the compounds of the formula (6A-1) [in the formula (6A-1), $R^{1a}$, $R^{2a}$, $R^{3a}$ and $R^{4a}$ are as defined in the above.] and the compounds of the formula (7A-1) [in the formula (7A-1), $R^{5a}$, $R^{6a}$, $R^{7a}$, $Cy^a$, X and Y are as defined in the above, and $Z^1$ is a fluorine atom, a chlorine atom, a bromine atom or an alkoxy group.] in the presence of a base according to a known method (Tetrahedron Lett., 43, 2945-2948(2002)), or a product obtained by reaction between the compounds of the formula (6A-2) [in the formula (6A-2), $R^{1a}$, $R^{2a}$ and $R^{3a}$ are as defined in the above, and $Z^2$ is a fluorine atom, a chlorine atom, a bromine atom or an alkoxy group.] and the compounds of the formula (7A-2) [in the formula (7A-2), $R^{4a}$, $R^{5a}$, $R^{6a}$, $R^{7a}$, $Cy^a$, X and Y are as defined in the above.] in the presence of a base can be used. With respect to the reaction between the compounds of the formula (6A-1) and the compounds of the formula (7A-1), the compounds of the formula (7A-1) can be used in an amount of 1/5 to 20 equivalents compared to the compounds represented by the formula (6A-1). It can be also ½ to 10 equivalents, and preferably is 1 to 5 equivalents. However, depending on purity, yield, and purification efficiency, etc. of the compounds represented by the formula (5A), it can be appropriately selected. As for the base which is used for the reaction, sodium hydride, potassium hydride, sodium ethoxide, potassium-t-butoxide or lithium hexamethyldisilazane and the like can be used. Preferably, it is lithium hexamethyldisilazane. The base can be used in an amount of one equivalent to an excess amount compared to the compounds of the formula (6A-1). It can be 1 to 10 equivalents, and preferably is 1 to 5 equivalents. As for the solvent which is used for the reaction, examples include N,N-dimethylformamide, N,N-dimethylacetamide, xylene, toluene, 1,4-dioxane, tetrahydrofuran and the like. Further, these solvents can be used as a mixture including two or more of them. In general, the reaction can be carried out at appropriate temperature in the temperature range of −40° C. to 80° C. Preferably, it is in the range of −20° C. to 40° C. Reaction time is not specifically limited. In general, it is in the range of 0.5 hour to 48 hours, preferably in the range of 1 to 24 hours. The reaction between the compounds of the formula (6A-2) and the compounds of the formula (7A-2) can be carried out with reference to the reaction between the compounds of the formula (6A-1) and the compounds of the formula (7A-1).

As for the compounds represented by the formula (6A-1), n-butyrophenone (manufactured by Wako Pure Chemical Industries, Ltd.), valerophenone (manufactured by Wako Pure Chemical Industries, Ltd.) and the like can be used.

Among the compounds represented by the formula (6A-1), the compounds of the formula (6A-1A) in which $R^{4a}$ is an alkyl group which may be substituted [in the formula (6A-1A), $R^{1a}$, $R^{2a}$ and $R^{3a}$ are as defined in the above.] can be prepared according to a retrosynthetic pathway according to the following reaction, for example.

[Chemical Formula 9]

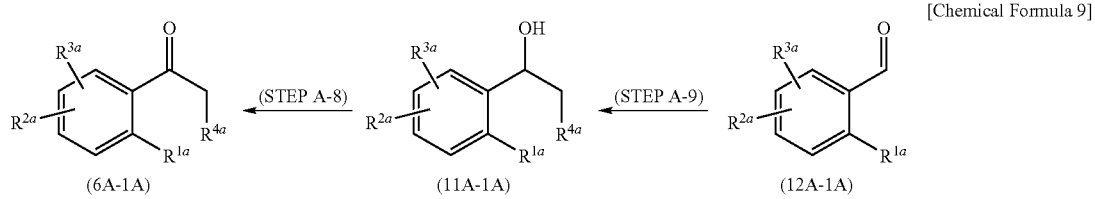

The compounds represented by the formula (6A-1A) can be prepared by subjecting the compounds represented by the formula (11A-1A) [in the formula (11A-1A), $R^{1a}$, $R^{2a}$ and $R^{3a}$ are as defined in the above.] to an oxidation reaction. With respect to an oxidation reaction, a method using Dess-Martin reagent, Swern oxidation or an oxidation method using chromic acid, and the like can be mentioned. The present reaction is carried out according to a known method, and preferably it is carried out according to a method in which pyridinium chlorochromate as chromic acid salt in an organic solvent is applied to the compounds represented by the formula (11A-1A) to obtain the compounds represented by the formula (6A-1A). Pyridinium chlorochromate can be used in an amount of 1/5 to 10 equivalents, and preferably is ½ to 3 equivalents compared to the compounds represented by the formula (11A-1A). As for the solvent which is used for the reaction, examples include N,N-dimethylformamide, toluene, dichloromethane, chloroform and the like. Dichloromethane is preferred. Further, these solvents can be used as a mixture including two or more of them. In general, the reaction can be carried out at appropriate temperature in the temperature range of −20° C. to 60° C. Preferably, it is in the range of 0° C. to 40° C. Reaction time is not specifically limited. In general, it is in the range of 1 hour to 48 hours, preferably in the range of 2 to 24 hours.

The compounds represented by the formula (11A-1A) can be prepared by reacting the compounds represented by the formula (12A-1A) [in the formula (12A-1A), $R^{1a}$, $R^{2a}$ and $R^{3a}$ are as defined in the above.] with a commercially available Grignard reagent that is represented by the formula (13A-1A): $R^{4a}$—$CH_2MgL^2$ [in the formula (13A-1A), $R^{4a}$ is as defined in the above and $L^2$ is a chlorine atom, a bromine atom or an iodine atom.] followed by addition of proton source for termination of the reaction. Examples of the Grignard reagent of the formula (13A-1A) include ethyl magnesium bromide (manufactured by Aldrich Company) or isobutyl magnesium bromide (manufactured by Aldrich Company) and the like. The compounds represented by the formula (13A-1A) can be used in an amount of ½ to 10 equivalents, and preferably is 1 to 5 equivalents compared to the compounds represented by the formula (12A-1A). As for the solvent which is used for the reaction, examples include N,N-dimethylformamide, toluene, 1,4-dioxane, tetrahydrofuran, diethyl ether and the like. Tetrahydrofuran is preferred. Further, these solvents can be used as a mixture including two or more of them. In general, the reaction can be carried out at appropriate temperature in the temperature range of −80° C. to 60° C. Preferably, it is in the range of −20° C. to 40° C. Reaction time is not specifically limited. In general, it is in the range of 0.2 hour to 24 hours, preferably in the range of 0.5 to 12 hours. As a proton source which is used for termination of the reaction, water, inorganic acid or organic acid, etc. can be used. Water is preferred. The proton source for termination of the reaction can be used in an amount of 1 equivalent to an excess amount compared to the compounds represented by the formula (13A-1A). The temperature for termination of the reaction can be generally between −80° C. and 60° C.

As for the compounds represented by the formula (12A-1A), commercially available benzaldehyde (manufactured by Tokyo Chemical Industry Co., Ltd.), p-methoxybenzaldehyde (manufactured by Wako Pure Chemical Industries, Ltd.) and the like can be used.

As for the compounds represented by the formula (7A-1), commercially available benzoyl chloride (manufactured by Tokyo Chemical Industry Co., Ltd.), p-methoxybenzoyl chloride (manufactured by Wako Pure Chemical Industries, Ltd.) and the like can be used.

As for the compounds represented by the formula (6A-2), commercially available benzoyl chloride (manufactured by Tokyo Chemical Industry Co., Ltd.), p-methoxybenzoyl chloride (manufactured by Wako Pure Chemical Industries, Ltd.) and the like can be used.

As for the compounds represented by the formula (7A-2), n-butyrophenone (manufactured by Wako Pure Chemical Industries, Ltd.), valerophenone (manufactured by Wako Pure Chemical Industries, Ltd.) and the like can be used.

In addition, as for the compounds of the formula (7A-2) in which $R^{4a}$ is an alkyl group which may be substituted, a compound which is prepared with reference to the method of synthesizing the compounds of the formula (6A-1A) as described above can be used.

Among the compounds represented by the formula (2), the compounds of the formula (2B) in which $A^{1a}$ is a single bond and $G^a$ is the formula ($G^{1a}$) [in the formula (2B), $R^{1a}$, $R^{2a}$, $R^{3a}$, $R^{4a}$, $R^{5a}$, $R^{6a}$, $R^{7a}$, $R^{8a}$, $R^{9a}$, $A^{2a}$, $Cy^a$, X and Y are as defined in the above, with the proviso that $R^{4a}$ and $R^{5a}$ together do not represent a ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom or a nitrogen atom.] can be prepared according to a retrosynthetic pathway according to the following reaction, for example.

[Chemical Formula 10]

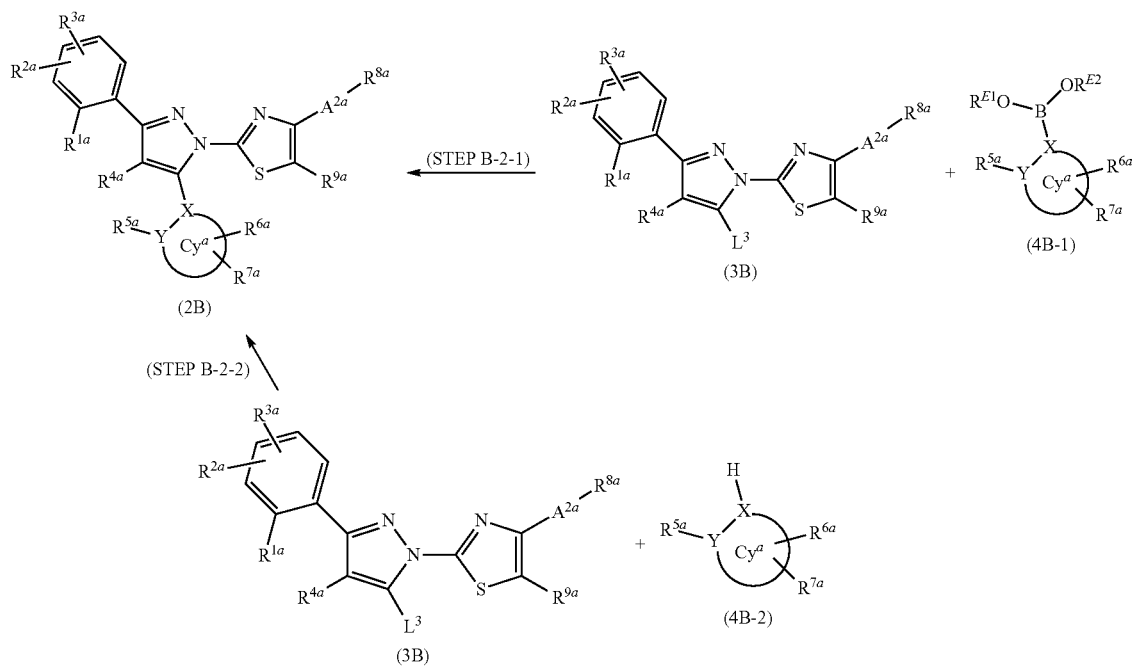

(3B) ←—(STEP B-3)—

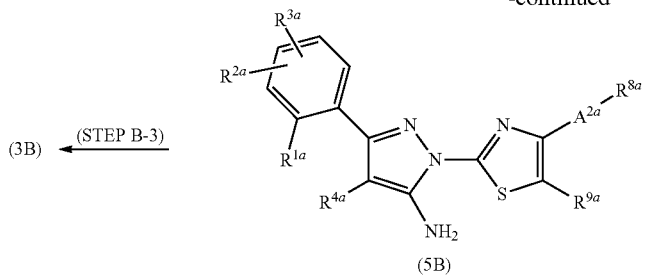

(5B)

Among the compounds represented by the formula (2B), the compounds in which X is a carbon atom can be prepared by reacting the compounds represented by the formula (3B) [in the formula (3B), $R^{1a}$, $R^{2a}$, $R^{3a}$, $R^{4a}$, $R^{8a}$, $R^{9a}$ and $A^{2a}$ are as defined in the above and $L^3$ is a chlorine atom, a bromine atom or an iodine atom.] with the compounds represented by the formula (4B-1) [in the formula (4B-1), $R^{5a}$, $R^{6a}$, $R^{7a}$, $Cy^a$ and Y are as defined in the above, and $R^{E1}$ and $R^{E2}$ can be the same or different to each other and each independently represent a hydrogen atom or a lower alkyl group, or $R^{E1}$ and $R^{E2}$ together form a 5- to 6-membered cyclic boronic acid ester ring of $B(OR^{E1})(OR^{E2})$.] by using a commercially available palladium catalyst or a catalyst which is obtained from a palladium complex and a ligand in the presence of a base. For the reaction between the compounds represented by the formula (3B) and the compounds represented by the formula (4B-1), the compounds represented by the formula (4B-1) can be used in an amount of ⅕ to 20 equivalents compared to the compounds represented by the formula (3B), and preferably it is ½ to 10 equivalents, and more preferably it is 1 to 5 equivalents. However, depending on purity, yield, and purification efficiency, etc. of the compounds represented by the formula (2B), it can be appropriately selected. As for the palladium catalyst, a commercially available catalyst such as tris(dibenzylideneacetone)dipalladium, dibenzylideneacetone palladium, tetrakis triphenylphosphine palladium, dichlorobis (triphenylphosphine)palladium, palladium acetate, palladium chloride and the like can be directly added to a reaction system, or a catalyst which is obtained by mixing palladium acetate or dibenzylideneacetone palladium with any ligand can be used. Examples of a ligand include triphenyl phosphine, tri-o-tolyl phosphine, tri-t-butyl phosphine, tricyclohexyl phosphine or 2-(di-t-butylphosphino)biphenyl and the like. Preferably, dibenzylideneacetone palladium is used with tri-o-tolyl phosphine as a ligand, or tetrakis triphenyl phosphine palladium is used without any ligand. The palladium catalyst is preferably used in an amount of 1/1000 to 1 equivalent compared to the compounds represented by the formula (3B). It can be used in an amount of 1/100 to ½ equivalents, and more preferably is 1/100 to ⅕ equivalents. Examples of a base include sodium carbonate, potassium carbonate, cesium carbonate, cesium fluoride, potassium fluoride, potassium phosphate, potassium acetate and the like. Preferably, it is sodium carbonate or potassium carbonate. The base can be used in an amount of 1/10 to 10 equivalents compared to the compounds of the formula (3B). Preferably, it is ⅕ to 5 equivalents. Examples of a solvent which can be used for the reaction include N,N-dimethylformamide, N,N-dimethylacetamide, xylene, toluene, 1,4-dioxane, tetrahydrofuran, ethanol, methanol and the like. Preferably, it is N,N-dimethylformamide or 1,4-dioxane. Further, these solvents can be used as a mixture including two or more of them. Still further, these solvents can be mixed with water and then used.

In general, the reaction can be carried out in the temperature range of 0° C. to 150° C. Preferably, it is in the temperature range of 40° C. to 120° C. Reaction time is not specifically limited. In general, it is in the range of 1 hour to 72 hours, preferably in the range of 2 to 24 hours.

Among the compounds represented by the formula (2B), the compounds in which X is a nitrogen atom can be prepared by reacting the compounds represented by the formula (3B) [in the formula (3B), $R^{1a}$, $R^{2a}$, $R^{3a}$, $R^{4a}$, $R^{8a}$, $R^{9a}$ and $A^{2a}$ as defined in the above and $L^3$ is a chlorine atom, a bromine atom or an iodine atom.] with the compounds represented by the formula (4B-2) [in the formula (4B-2), $R^{5a}$, $R^{6a}$, $R^{7a}$, $Cy^a$ and Y are as defined in the above.] by using a commercially available copper catalyst or a catalyst that is obtained from copper powder or copper salt with a ligand compound in the presence of a base. For the reaction of the compounds represented by the formula (3B) and the compounds represented by the formula (4B-2), the compounds represented by the formula (4B-2) can be used in an amount of ⅕ to 20 equivalents compared to the compounds represented by the formula (3B). It can be also ½ to 10 equivalents, and preferably is 1 to 5 equivalents. However, depending on purity, yield, and purification efficiency, etc. of the compounds represented by the formula (2B), it can be appropriately selected. As a copper catalyst, a commercially available catalyst such as bis(acetylacetonate) copper (II) and the like can be directly added to a reaction system or a catalyst obtained by mixing copper powder, copper (I) chloride, copper (I) bromide, copper (I) iodide, copper (I) cyanide, copper (I) oxide, copper (II) chloride, copper (II) bromide, copper (II) acetate, copper (II) sulfate, or copper (II) oxide and a ligand can be used. Examples of a ligand include (1S, 2S)-(+)-N,N-dimethylcyclohexane-1,2-diamine, (1R, 2R)-(−)-N,N-dimethylcyclohexane-1,2-diamine, (1S, 2S)-(+)-1,2-cyclohexanediamine, (1R, 2R)-(−)-1,2-cyclohexanediamine, 1,10-phenanthroline, 2,9-dimethyl-1,10-phenanthroline, 4,7-dimethyl-1,10-phenanthroline, 3,4,7,8-tetramethyl-1,10-phenanthroline, 2,2,6,6-tetramethyl-3,5-heptanedione, 2-acetylcyclohexanone, 2-propionylcyclohexanone, N,N-diethylsalicylamide, N-methylethylenediamine, N,N-dimethylethylenediamine, N,N'-dimethylethylenediamine, N,N,N',N'-tetramethylethylenediamine, 8-quinolinol, 1,1'-binaphthyl-2,2'-diol, 2,2'-dihydroxybiphenyl, catechol, ethylene glycol, 9,10-phenanthrene quinone, L-(−)-proline, D-(+)-proline, glycine and the like. Preferably, copper (I) iodide is used with 2-acetylcyclohexanone as a ligand. The copper catalyst is used in an amount of 1/1000 to 1 equivalent compared to the compounds of the formula (3B). It can be 1/100 to ½ equivalents, and preferably is 1/100 to ⅕ equivalents. Examples of a base include lithium hydroxide, sodium hydroxide, potassium hydroxide, sodium carbonate, potassium carbonate, cesium carbonate, cesium fluoride, potassium fluoride, potassium phosphate, potassium acetate and the like. Preferably, it is potassium phosphate or cesium carbonate. The base can be used in an amount of 1/20 to 20 equivalents compared to the compounds of the formula (3B). It can be 1/10 to 10 equivalents, and preferably is 1/2 to 5 equivalents. Examples of a solvent which can be used for the reaction include N,N-dimethylformamide, N,N-dimethylacetamide, N-methyl-2-pyrrolidone, toluene, xylene, mesitylene, 1,4-dioxane, tetrahydrofuran or dimethyl sulfoxide and the like. Preferably, it is N,N-dimethylacetamide or mesitylene. Further, these solvents can be used as a mixture including two or more of them. Still further, these solvents can be mixed with water and then used. In general, the reaction can be carried out in the temperature range of 20° C. to 250° C. Preferably, it is in the temperature range of 60° C. to 200° C. Reaction time is not specifically limited. In general, it is in the range of 4 hours to 72 hours, preferably in the range of 8 to 48 hours.

The compounds represented by the formula (3B) can be prepared by reacting the compounds represented by the formula (5B) [in the formula (5B), $R^{1a}$, $R^{2a}$, $R^{3a}$, $R^{4a}$, $R^{8a}$, $R^{9a}$ and $A^{2a}$ are as defined in the above.] with salts and ester of nitrous acid followed by reaction with a metal halide compound or a halogen molecule. This reaction is carried out according to a known method. A preferable example includes a method in which the compounds of the formula (5B) are reacted with ester of nitrous acid in an organic solvent followed by reaction with a metal halide compound for halogenation. Examples of an ester of nitrous acid include t-butyl nitrous acid or isoamyl nitrous acid and the like. The ester of nitrous acid can be used in an amount of 1/5 to 20 equivalents compared to the compounds of the formula (5B). Preferably, it is 1/2 to 10 equivalents, and more preferably is 1 to 5 equivalents. When a halogen molecule is used, a halide molecule is preferably selected depending on the halogen atom that is represented by $L^3$ in the compounds of the formula (3B). Specifically, when $L^3$ is a bromine atom, a bromine molecule is preferably used. When $L^3$ is an iodine atom, an iodine molecule is preferably used. The halide molecule can be used in an amount of 1/5 to 50 equivalents compared to the compounds of the formula (5B). Preferably, it is 1/2 to 20 equivalents, and more preferably is 1 to 10 equivalents. As for the solvent which is used for the reaction, 1,4-dioxane, tetrahydrofuran or acetonitrile can be used. Preferably, it is acetonitrile. Further, these solvents can be used as a mixture including two or more of them. In general, the reaction can be carried out in the temperature range of 0° C. to 200° C. Preferably, it is in the temperature range of 20° C. to 100° C. Reaction time is not specifically limited. In general, it is in the range of 0.5 hours to 24 hours, preferably in the range of 1 to 12 hours. Further, according to other embodiment, there is a preferable method in which salt of nitrous acid is reacted in an aqueous acid solution followed by reaction with a metal halide for halogenation. Examples of an aqueous acid solution include sulfuric acid, hydrochloric acid, hydrogen bromide acid and the like. Examples of salts of nitrous acid include sodium nitrite and the like. When a metal halide is used, those including the halogen atom which corresponds to the one included in $L^3$ of the desired formula (3B) can be used. Specifically, when $L^3$ is a bromine atom, copper bromide or potassium bromide is preferably used. When $L^3$ is an iodine atom, copper iodide or potassium iodide is preferably used.

As for the compounds represented by the formula (4B-1), commercially available benzene boronic acid (manufactured by Tokyo Chemical Industry Co., Ltd.), thiophen-2-boronic acid (manufactured by Aldrich Company), thiophen-3-boronic acid (manufactured by Aldrich Company) or 3-pyridine boronic acid (manufactured by Wako Pure Chemical Industries, Ltd.) and the like can be used. Further, a compound that is prepared according to a known method (see, Chem. Rev., 95, 2457-2483 (1995) or J. Organomet. Chem., 576, 147-168 (1999), etc.) can be used.

As for the compounds represented by the formula (4B-2), commercially available pyrrolidine (manufactured by Tokyo Chemical Industry Co., Ltd.), piperidine (manufactured by Tokyo Chemical Industry Co., Ltd.), morpholine (manufactured by Tokyo Chemical Industry Co., Ltd.), 1-methylpiperazine (manufactured by Tokyo Chemical Industry Co., Ltd.), pyrrole (manufactured by Tokyo Chemical Industry Co., Ltd.), imidazole (manufactured by Tokyo Chemical Industry Co., Ltd.), or pyrazole (manufactured by Tokyo Chemical Industry Co., Ltd.), etc. can be used.

Among the compounds represented by the formula (5B), the compounds of the formula (5BA) in which $A^{2a}$ is a single bond, $R^{4a}$ is an alkyl group which may be substituted, and $R^{8a}$ is —$COOR^{E3}$ [in the formula (5BA), $R^{1a}$, $R^{2a}$, $R^{3a}$ and $R^{9a}$ are as defined in the above, and $R^{E3}$ represents an alkyl group which may be substituted.] can be prepared according to a retrosynthetic pathway according to the following reaction, for example.

[Chemical Formula 11]

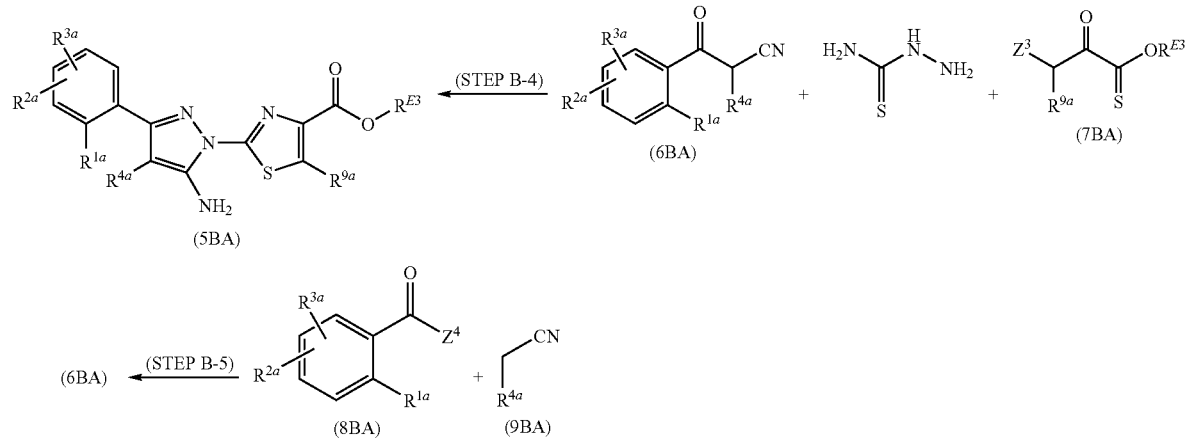

The compounds represented by the formula (5BA) can be prepared by reacting the compounds represented by the formula (6BA) [in the formula (6BA), $R^{1a}$, $R^{2a}$, $R^{3a}$ and $R^{4a}$ are as defined in the above.] with thiosemicarbazide followed by reaction with the compounds represented by the formula (7BA) [in the formula (7BA), $R^{9a}$ and $R^{E3}$ are as defined in the above, and $Z^3$ represents a chlorine atom, a bromine atom or an iodine atom.]. Thiosemicarbazide can be used in an amount of 1/10 to 10 equivalents compared to the compounds of the formula (6BA). Preferably, it is 1/5 to 5 equivalents, and more preferably is 1/2 to 2 equivalents. The compounds represented by the formula (7BA) can be used in an amount of 1/10 to 10 equivalents compared to the compounds of the formula (6BA). Preferably, it is 1/5 to 5 equivalents, and more preferably is 1 to 3 equivalents. However, depending on purity, yield, and purification efficiency, etc. of the compounds represented by the formula (5BA), it can be appropriately selected. As for the solvent which is used for the reaction, methanol, ethanol, isopropyl alcohol, 2-methyl-2-propanol, N,N-dimethylformamide, toluene, 1,4-dioxane, or tetrahydrofuran can be used. Preferably, it is ethanol or isopropyl alcohol. Further, these solvents can be used as a mixture including two or more of them. In general, the reaction can be carried out in the temperature range of 0° C. to 150° C. Preferably, it is in the temperature range of 40° C. to 120° C. Reaction time is not specifically limited. In general, it is in the range of 0.5 hours to 48 hours, preferably in the range of 2 to 12 hours.

The compounds represented by the formula (6BA) can be prepared by reacting the compounds represented by the formula (8BA) [in the formula (8BA), $R^{1a}$, $R^{2a}$ and $R^{3a}$ are as defined in the above and $Z^4$ represents a fluorine atom, a chlorine atom, a bromine atom or an alkoxy group.] with the compounds represented by the formula (9BA) [in the formula (9BA), $R^{4a}$ is as defined in the above.] in the presence of a base. For the reaction between the compounds represented by the formula (8BA) and the compounds represented by the formula (9BA), the compounds represented by the formula (9BA) can be used in an amount of 1/10 to 10 equivalents compared to the compounds of the formula (8BA). Preferably, it is 1/5 to 5 equivalents, and more preferably is 1/2 to 2 equivalents. However, depending on purity, yield, and purification efficiency, etc. of the compounds represented by the formula (6BA), it can be appropriately selected. Examples of a base include sodium hydride, sodium ethoxide, sodium carbonate, potassium carbonate and the like. Preferably, it is sodium ethoxide. The base can be used in an amount of one equivalent to an excess amount compared to the compounds of the formula (8BA). It can be 1 to 10 equivalents, and preferably is 1 to 5 equivalents. Examples of a solvent which can be used for the reaction include N,N-dimethylformamide, N,N-dimethylacetamide, xylene, toluene, 1,4-dioxane, tetrahydrofuran and the like. Tetrahydrofuran is preferable. Further, these solvents can be used as a mixture including two or more of them. In general, the reaction can be carried out in the temperature range of 0° C. to 150° C. Preferably, it is in the temperature range of 40° C. to 120° C. Reaction time is not specifically limited. In general, it is in the range of 1 hour to 48 hours, preferably in the range of 2 to 24 hours.

As for the compounds represented by the formula (7BA), commercially available ethyl bromopyruvic acid manufactured by Wako Pure Chemical Industries, Ltd.) or methyl bromopyruvic acid (manufactured by Fluka) and the like can be used. Further, a compound that is prepared according to a known method (J. Org. Chem., 67, 1102-1108 (2002), etc.) can be used.

As for the compounds represented by the formula (8BA), commercially available ethyl benzoic acid (manufactured by Wako Pure Chemical Industries, Ltd.), p-ethyl anisic acid (manufactured by Wako Pure Chemical Industries, Ltd.), p-ethyl toluic acid (manufactured by Wako Pure Chemical Industries, Ltd.), o-ethyl toluic acid (manufactured by Tokyo Chemical Industry Co., Ltd.), p-chloro ethyl benzoic acid (manufactured by Tokyo Chemical Industry Co., Ltd.), p-methoxybenzoyl chloride (manufactured by Tokyo Chemical Industry Co., Ltd.) and the like can be used.

As for the compounds represented by the formula (9BA), commercially available propionitrile (manufactured by Wako Pure Chemical Industries, Ltd.), n-butyronitrile (manufactured by Wako Pure Chemical Industries, Ltd.) and the like can be used. Further, a compound that is prepared according to a known method (see, J. Org. Chem., 25, 877-879 (1960) or J. Org. Chem., 39, 3416-3418 (1974) etc.) can be used.

Among the compounds represented by the formula (2), the compounds of the formula (2C) in which $A^{1a}$ is a single bond, $G^a$ is the formula ($G^{1a}$), $A^{2a}$ is a single bond, $R^{8a}$ is —CO-$OR^{E3}$, $Cy^a$ is an aryl group and $R^{4a}$ is an amino group [in the formula (2C), $R^{1a}$, $R^{2a}$, $R^{3a}$, $R^{5a}$, $R^{6a}$, $R^{7a}$, $R^{9a}$, $R^{E3}$, $Cy^a$, X and Y are as defined in the above.] can be prepared according to a retrosynthetic pathway according to the following reaction, for example.

[Chemical Formula 12]

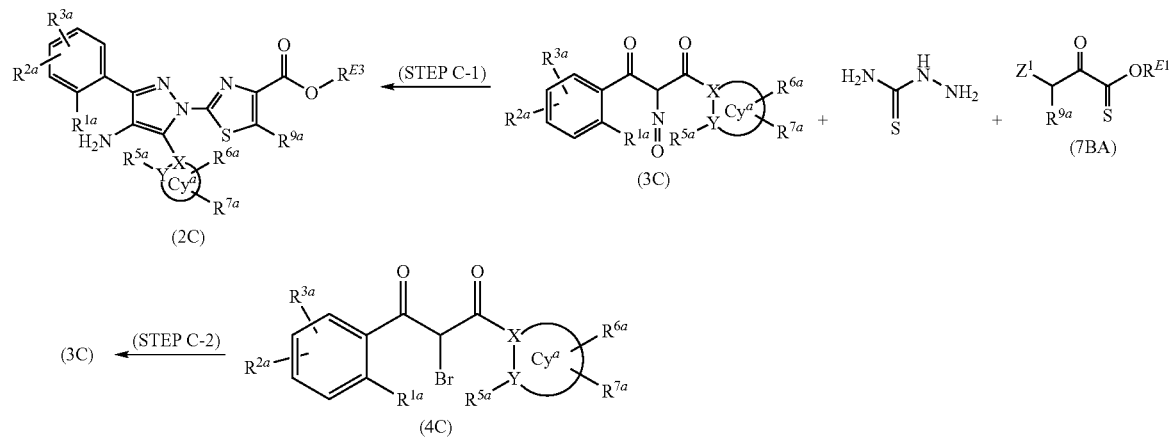

The compounds represented by the formula (2C) can be prepared by reacting the compounds represented by the formula (3C) [in the formula (3C), $R^{1a}$, $R^{2a}$, $R^{3a}$, $R^{5a}$, $R^{6a}$, $R^{7a}$, $Cy^a$, X and Y are as defined in the above.] with thiosemicarbazide followed by reaction with the compounds represented by the formula (7BA) [in the formula (7BA), $R^{9a}$ and $R^{E3}$ or $Z^3$ are as defined in the above.]. The preparation of the compounds of the formula (7BA) can be carried out with reference to the method for synthesizing the compounds of the formula (5BA) described above in detail.

The compounds represented by the formula (3C) can be prepared by reacting the compounds represented by the formula (4C) [in the formula (4C), $R^{1a}$, $R^{2a}$, $R^{3a}$, $R^{5a}$, $R^{6a}$, $R^{7a}$, $Cy^a$, X and Y are as defined in the above.] simultaneously with salt of nitrous acid and urea. Examples of salt of nitrous acid include sodium nitrite and the like. The salt of nitrous acid can be used in an amount of ⅕ to 20 equivalents compared to the compounds of the formula (4C). Preferably, it is ½ to 10 equivalents, and more preferably is 1 to 5 equivalents. The urea can be used in an amount of ⅕ to 50 equivalents compared to the compounds of the formula (4C). Preferably, it is ½ to 20 equivalents, and more preferably is 2 to 10 equivalents. As for the solvent which is used for the reaction, methanol, ethanol, isopropyl alcohol, 2-methyl-2-propanol, N,N-dimethylformamide, dimethyl sulfoxide, toluene, 1,4-dioxane, or tetrahydrofuran can be used. Preferably, it is dimethyl sulfoxide. Further, these solvents can be used as a mixture including two or more of them. In general, the reaction can be carried out in the temperature range of −20° C. to 100° C. Preferably, it is in the temperature range of 0° C. to 40° C. Reaction time is not specifically limited. In general, it is in the range of 0.5 hours to 48 hours, preferably in the range of 2 to 24 hours.

As for the compounds represented by the formula (4C), a compound that is prepared according to a known method (see, J. Org. Chem., 71, 8961-8963 (2006) etc.) can be used.

Among the compounds represented by the formula (2), the compounds of the formula (2DA) in $A^{1a}$ is an ethylene group, and $R^{8a}$ is —$COOR^{E4}$ [in the formula (2DA), $R^{1a}$, $R^{2a}$, $R^{3a}$, $R^{4a}$, $R^{5a}$, $R^{6a}$, $R^{7a}$, $R^{9a}$, $Cy^a$, X and Y are as defined in the above and $R^{E4}$ is an alkyl group.] can be prepared according to a retrosynthetic pathway according to the following reaction, for example.

[Chemical Formula 13]
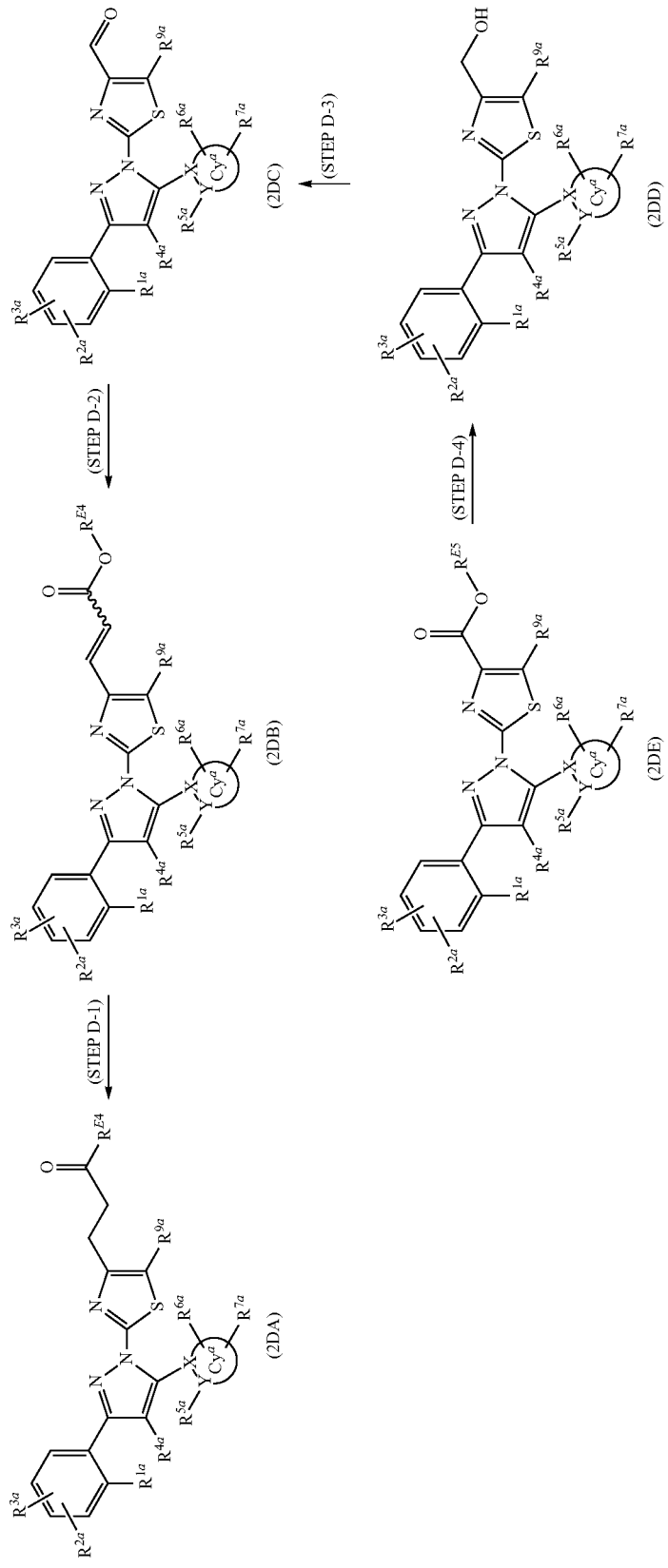

Among the compounds represented by the formula (2DA), the compounds of the formula (2) in which $A^{1a}$ is a single bond, $G^a$ is the formula ($G^{1a}$), $A^{2a}$ is an ethenylene group and $R^{8a}$ is —COOR$^{E4}$ [in the formula (2DB), $R^{1a}$, $R^{2a}$, $R^{3a}$, $R^{4a}$, $R^{5a}$, $R^{6a}$, $R^{7a}$, $R^{9a}$, $R^{E4}$, $Cy^a$, X and Y are defined in the above, and stereochemistry relating to a double bond of the ethenylene group of $A^{2a}$ can be any of cis and trans.] can be obtained by subjecting the compounds represented by the formula (2DA) to a reducing reaction. With respect to a reducing reaction, a reduction based on contact with hydrogen can be mentioned. The reduction based on contact with hydrogen can be carried out by using a catalyst in a solvent under hydrogen atmosphere. Examples of a catalyst include palladium-carbon, platinum oxide, platinum-carbon or palladium hydroxide and the like. Examples of a solvent which can be used for the reaction include ethyl acetate, diethyl ether, tetrahydrofuran, dioxane, dimethoxyethane, methanol, ethanol and the like. Preferably, it is tetrahydrofuran or methanol. Further, these solvents can be used as a mixture including two or more of them. In general, the reaction can be carried out in the temperature range of −20° C. to 100° C. Preferably, it is in the temperature range of 0° C. to 50° C. Reaction time is not specifically limited. In general, it is in the range of 1 hour to 96 hours, preferably in the range of 3 to 48 hours.

The compounds represented by the formula (2DB) can be prepared by reacting the compounds represented by the formula (2DC) in which $A^{1a}$ is a single bond, $G^a$ is the formula ($G^{1a}$), $A^{2a}$ is a single bond and $R^{8a}$ is a formyl group [in the formula (2DC), $R^{1a}$, $R^{2a}$, $R^{3a}$, $R^{4a}$, $R^{5a}$, $R^{6a}$, $R^{7a}$, $R^{9a}$, $Cy^a$, X and Y are as defined in the above.] with commercially available dialkylphosphono acetate in the presence of a base. Examples of dialkylphosphono acetate include ethyl diethyl phosphonic acid, bis(2,2,2-trifluoroethyl)(methoxycarbonylmethyl)phosphonic acid and the like. Dialkylphosphono acetate can be used in an amount of ⅕ to 10 equivalents compared to the compounds represented by the formula (2DC). It is preferably ½ to 3 equivalents. Examples of a base include sodium hydroxide, potassium hydroxide, potassium carbonate, sodium hydride, potassium-t-butoxide, potassium hexamethyldisilazne and the like. Preferably, it is sodium hydride or potassium hexamethyldisilazne. The base can be used in an amount of ½ to 20 equivalents compared to the compounds of the formula (2DC) as a reacting material. It is preferably ½ to 5 equivalents. As for the solvent which is used for the reaction, N,N-dimethylformamide, N,N-dimethylacetamie, toluene, 1,4-dioxane, or tetrahydrofuran can be mentioned. Preferably, it is 1,4-dioxane or tetrahydrofuran. Further, these solvents can be used as a mixture including two or more of them. In general, the reaction can be carried out in the temperature range of −20° C. to 100° C. Preferably, it is in the temperature range of 0° C. to 40° C. Reaction time is not specifically limited. In general, it is in the range of 1 hour to 24 hours, preferably in the range of 2 to 12 hours.

The compounds represented by the formula (2DC) can be prepared by subjecting the compounds represented by the formula (2DD) [in the formula (2DD), $R^{1a}$, $R^{2a}$, $R^{3a}$, $R^{4a}$, $R^{5a}$, $R^{6a}$, $R^{7a}$, $R^{9a}$, $Cy^a$, X and Y are as defined in the above.], i.e., the compounds of the formula (2) in which $A^{1a}$ is a single bond, $G^a$ is the formula ($G^{1a}$), $A^{2a}$ is a single bond and $R^{8a}$ is a hydroxymethyl group, to an oxidation reaction. With respect to an oxidation reaction, a method using Dess-Martin Periodinane, Swern oxidation or an oxidation method using chromic acid, and the like can be mentioned. The present reaction is carried out according to a known method, and preferably it is carried out according to a method in which the compounds represented by the formula (2DD) are reacted with a Dess-Martin Periodinane in an organic solvent to obtain the compounds represented by the formula (2DC). The Dess-Martin Periodinane can be used in an amount of ⅕ to 10 equivalents compared to the compounds of the formula (2DD). It can be ⅕ to 10 equivalents, and preferably is ½ to 3 equivalents. As for the solvent which is used for the reaction, N,N-dimethylformamide, toluene, dichloromethane and chloroform and the like can be used. Preferably, it is dichloromethane. Further, these solvents can be used as a mixture including two or more of them. In general, the reaction can be carried out in the temperature range of −20° C. to 60° C. Preferably, it is in the temperature range of 0° C. to 40° C. Reaction time is not specifically limited. In general, it is in the range of 1 hour to 48 hours, preferably in the range of 2 to 24 hours.

The compounds represented formula (2DD) can be prepared by reacting the compounds of the formula (2DE) [in the formula (2DE), $R^{1a}$, $R^{2a}$, $R^{3a}$, $R^{4a}$, $R^{5a}$, $R^{6a}$, $R^{7a}$, $R^{9a}$, $Cy^a$, X and Y are as defined in the above and $R^{E5}$ is an alkyl group.], i.e., the compounds represented by the formula (2) in which $A^{1a}$ is a single bond, $G^a$ is the formula ($G^{1a}$), $A^{2a}$ is a single bond and $R^{8a}$ is —COOR$^{E5}$, with a commercially available metal hydride compound. Types of a metal halide compound include, for example, lithium aluminum hydride, a borane-tetrahydrofuran complex and the like. Preferably, lithium aluminum hydride is used. The metal hydride compound can be used in an amount of ¼ to 5 equivalents compared to the compounds of the formula (2DE). It can be preferably ½ to 3 equivalents. As for the solvent which is used for the reaction, diethyl ether, tetrahydrofuran, 1,4-dioxane and the like can be used. Preferably, it is tetrahydrofuran. Further, these solvents can be used as a mixture including two or more of them. In general, the reaction can be carried out in the temperature range of −20° C. to 80° C. Preferably, it is in the temperature range of 0° C. to 60° C. Reaction time is not specifically limited. In general, it is in the range of 1 hour to 48 hours, preferably in the range of 2 to 24 hours.

From the compounds represented by the formula (1) above, salts can be prepared. A method for producing salts is not specifically limited. For example, as a method for producing an acid addition salt, the compounds represented by the formula (1) are dissolved in alcohols such as methanol, and ethanol and added with one equivalent to several equivalents of an acid component to obtain acid addition salts. With respect to an acid component, any acid component which corresponds to acid addition salts described below can be used. Examples include a pharmaceutically acceptable mineral acid or organic acid such as hydrochloric acid, hydrobromic acid, sulfuric acid, hydrogen sulfuric acid, dihydrogen phosphate, hydrogen phosphate, citric acid, maleic acid, tartaric acid, fumaric acid, gluconic acid, methanesulfonic acid and the like. Further, as a method for producing a base addition salt, it can be carried out in the same manner as the method for producing an acid salt as described above, except that a base component is used instead of an acid component. With respect to a base component, any base component which corresponds to base addition salts described below can be used. Examples include a pharmaceutically acceptable base such as sodium hydroxide, potassium hydroxide, N-methyl-D-glucamine, N,N'-dibenzylethylenediamine, 2-aminoethanol, tris(hydroxymethyl)aminomethane, arginine, lysine and the like.

According to the present invention, the "compounds represented by the formula (1)" are understood as the compounds having the formula (1) in free form. Further, regarding salts thereof, the salts described below can be mentioned.

With respect to the salts of the compounds of the present invention, their type is not specifically limited. It can be any of an acid addition salt and a base addition salt. It can be also present in counter ion form in a molecule. In particular, when employed as an effective component of a pharmaceutical agent, pharmaceutically acceptable salts are particularly preferable. According to the present specification, when described in connection with the use as a pharmaceutical agent, the salts of the compounds of the present invention are generally understood as a pharmaceutically acceptable salt. Examples of an acid addition salt include hydrochloric acid salt, hydrobromic acid salt, sulfuric acid salt, hydrogen sulfuric acid salt, dihydrogen phosphoric acid salt, citric acid salt, maleic acid salt, tartaric acid salt, fumaric acid salt, gluconic acid salt, methanesulfonic acid salt, or an addition salt with optically active acid such as camphor sulfonic acid, mandelic acid or substituted mandelic acid. Examples of a base addition salt include a metal salt such as sodium salt, potassium salt and the like, and an addition salt with an organic base such as N-methyl-D-glucamine, N,N'-dibenzylethylenediamine, 2-aminoethanol, tris(hydroxymethyl)aminomethane, arginine or lysine, etc. However, salt types are not limited to these and it is obvious that a skilled person in the art can appropriately select them. Among them, a pharmaceutically acceptable salt is preferred.

The compounds of the present invention can be anhydrous form. Further, hydrates of the compounds of the present invention are also preferable.

Further, solvates of the compounds of the present invention are preferable, and non-solvates are also preferable.

Further, the compounds of the present invention can be either crystalline or non-crystalline. The crystals can be a monocrystal or a mixture including multiple types of crystalline form. Further, it also can be a mixture including both crystalline form and non-crystalline form.

More specifically, preferred examples include anhydrous and non-solvate form of the "compounds represented by the formula (1)" or a hydrate and/or a solvate thereof, or crystals thereof.

Still further, anhydrous and non-solvate form of the "salts of the compounds represented by the formula (1)" or a hydrate and/or a solvate thereof, and also anhydrous and non-solvate form of the salts or a hydrate and/or a solvate of the salts are also acceptable.

When a prodrug is to be produced from the compounds of the present invention, in accordance with a general method, a group which can form a prodrug is appropriately introduced to at least one group selected from the hydroxy group and the amino group included in the compounds of the present invention by using a reagent for preparing a prodrug, e.g., corresponding halide compound, etc., and then the prodrug can be appropriately obtained by general separation and purification method. Further, a reagent for preparing a prodrug, like an alcohol or an amine, can be used to introduce a group which can appropriately form a prodrug with the carboxy group of the compounds of the present invention. Still further, to obtain a prodrug, the protective group present on the compounds of the formula (2) can be utilized during the production process.

Prodrugs of the compounds of the present invention are not specifically limited and examples thereof include a compound in which a functional group, which can form a prodrug, is introduced to at least one group selected from the hydroxy group, the amino group and the carboxy group contained in the compounds of the present invention. As for a functional group which can form a prodrug with a hydroxy group or an amino group, an acyl group and an alkoxycarbonyl group can be exemplified. Preferred examples thereof include an acetyl group, a propionyl group, a methoxycarbonyl group, an ethoxycarbonyl group and the like. An ethoxycarbonyl group is more preferred. In addition, there is other embodiment in which an acetyl group is more preferred. In addition, there is other embodiment in which a propionyl group is more preferred. In addition, there is also other embodiment in which a methoxycarbonyl group is more preferred. As for a functional group which can form a prodrug with a carboxy group, a methyl group, an ethyl group, n-propyl group, an isopropyl group, an n-butyl group, an isobutyl group, a s-butyl group, a t-butyl group, an amino group, a methylamino group, an ethylamino group, a dimethylamino group, or a diethylamino group can be exemplified. Preferred examples thereof include an ethyl group, an n-propyl group, an isopropyl group and the like. An ethyl group is more preferred. In addition, there is other embodiment in which an n-propyl is more preferred. In addition, there is also other embodiment in which an isopropyl group is more preferred.

The compounds of the present invention may sometimes have an asymmetric carbon. Stereoconfiguration of such asymmetric carbon is not specifically limited, and it can be any of R configuration and S configuration, or a mixture including both of them. Any stereoisomers including optical isomers in pure form or a diastereomer derived from such asymmetric carbon, any mixture of stereoisomers, racemate and the like are all within the scope of the present invention.

The compounds of the present invention have a potent inhibitory effect on EP1 receptor as shown in Test example 1 described below, and therefore are useful as an effective component for a pharmaceutical agent.

The compounds of the present invention are an antagonist for EP1 receptor and can be applied for various disorders wherein EP1 receptor is involved. In addition, they are useful as an analgesic, a febricide, a pain reliever, or an agent for prophylaxis and/or treatment of symptoms of a lower urinary tract. In particular, among the symptoms of a lower urinary tract, they are effective for urine collection disorder, and especially useful as an agent for prophylaxis and/or treatment of an overactive bladder. Symptoms of an overactive bladder include frequent urination, urinary urgency and urinary incontinence. Urinary urgency is exemplified as a preferred example. In addition, there is other embodiment in which frequent urination or urinary incontinence is preferred example. As for urinary incontinence, urge incontinence can be mentioned as a preferred example. The compounds of the present invention are also effective for these symptoms.

It has been known that PGE2 is produced in bladder smooth muscle or endothelium of a urinary tract (Brown, W W. et al., Am. J. Physiol., 239,p. F452-F458 (1980), Mitchell J A & Warner T D, Br. J. Pharmacol., 128,p. 1121-1132 (1999)). It has been also known that PGE2 can induce contraction of a human isolated urinary bladder piece (Palea, S., et al., Br. J. Pharmacol. 124 (1998) 865-872) or can regulate urinary reflection by acting on a capsaicin-sensitive sensory nerve (Maggi, C A., Pharmacol. Res. 25,p 13-20 (1992)). Further, it has been demonstrated that PGE2 is involved with occurrence of an overactive bladder as it was confirmed that PGE2 infusion into a urinary bladder caused decreased urethal closure pressure, contraction of a urinary bladder, and a strong urgency sensation (Schussler, B. Urol. Res., 18,p 349-352 (1990)).

Meanwhile, it has been known that an EP1 antagonist can increase urinary bladder capacity of a normal rat (Maggi, C A., et al., Eur. J. Pharmacol. 152,p. 273-279 (1988)), can inhibit detrusor overactivity (Yoshida M. et al., J. Urol. 163, suppl. 44,abstract 191,(2000)), and can inhibit afferent nerve activity during urinary bladder inflammation (Ikeda M., et al., Biomed Res. 27, p. 49-54, (2006)). It was also reported that normal micturition is not affected while micturition interval was not shortened by intravesical PGE2 administration or lower urinary tract obstruction in an EP1 receptor knockout mouse (Schroder, A., et al., J. Urol., 172, p. 1166-1170 (2004)). It is expected that the compounds of the present invention have an effect of improving abnormal micturition in a disorder state and are useful for improving symptoms in a lower urinary tract, and other symptoms including urinary overactivity or frequent urination, urinary urgency, urinary incontinence and the like.

Usefulness of the compounds of the present invention as an effective component of a pharmaceutical agent for improving symptoms including frequent urination, urinary urgency, urinary incontinence and the like and the prophylaxis and/or treatment of symptoms in a lower urinary tract can be verified by the method described in any of the following Test example 4, Test example 5, Test example 6, Test example 7, Test example 8 or Test example 9, or combination thereof.

It is known that, EP1 knockout mouse has less sensitivity for pain (acetate-induced stretching activity is decreased; Stock, J L., et al., J Clin. Invest. 107, p. 325-331 (2000)), and an EP1 antagonist is effective for rat CCI model (Kawahara, H., et al., Anesth Analg., 93, p 1012-1017 (2001)), having an analgesic activity in Freund's complete adjuvant rat model (Giblin, G M P. et al., Bioorg. Med. Chem. Lett. 17, p. 385-389 (2007)) and an analgesic activity in a rat model of postoperative pain (Omote, K. et al., Anesth Analg. 92, p. 233-238 (2001)). In addition, it has been known that an EP1 antagonist is useful for relieving pain and/or neurogenic algesic pain. Usefulness of the compounds of the present invention as an effective component of a pharmaceutical agent for relieving pain can be verified by a method which includes administering orally, intravenously, or intraperitoneally the compounds to a mouse and examining the number of stretching after the intraperitoneal administration of acetic acid (i.e., acetic acid rising method). Alternatively, skin and fascia are cut from heel to the tip of paw of a hind limb of a rat, then they are sewn together and the animal is put into a cage for recovery, followed by oral, intravenous, or intraperitoneal administration of the compound and confirmation of threshold value for various kinds of stimulation. Alternatively, to a rat in which a solution (adjuvant) including inactivated tuberculosis bacteria (M. TUBERCULOSIS DES. H37 RA, DIFCO Laboratories) has been administered to its sole of left hind paw, the compounds are administered orally, intravenously, or intraperitoneally, and then escape behavior threshold is obtained by using Von Frey type apparatus for measurement of algesic pain. Still alternatively, to a rat with removed sciatic nerve, the compounds are administered orally, intravenously, or intraperitoneally and threshold values for various kinds of stimulation can be examined, and therefore the usefulness of the compounds for neurogenic pain can be confirmed.

It was reported that an EP1 antagonist is effective for kidney disorder of a rat having diabetes that is induced by streptozocin (STZ) (Makino, H., et al., J. Am, Soc, Nephrol. 13, 1757-1765 (2002)), kidney disorder of a SHRSP rat, which is a spontaneous hypertensive rat model (Suganami, T., et al., Hypertension 42, 1183-1190 (2003)) and also for improving a kidney disorder. Usefulness of the compounds of the present invention as an effective component of a pharmaceutical agent for the prophylaxis and/or treatment of a kidney disorder can be verified by examining the amount of protein contained in urine or a histological change in kidney, etc. after oral, intravenous or intraperitoneal administration of the compounds to a SHRSP rat or a STZ rat.

It has been reported that an EP1 antagonist is effective for a mouse skin cancer model (Tober, K L., et al., J. Invest. Dermatol., 126, p 205-211 (2006), a rat colon cancer model (Kawamori, T., et al., Anticancer Res., 21, p 3865-3869 (2001), Niho, N., et al., Cancer Sci., 96, p 260-264 (2005)), a rat lung cancer model (Kawamori, T., et al., Carcinogenesis, 22, p 2001-2004 (2001)), and it can inhibit the proliferation of gliomaous cell and growth of mouse tumor cell (Matsuo, M., et al., J. Neurooncol., 66, 285-292 (2004)). Further, it is known that the EP1 antagonist can be possibly used in the field of cancer treatment. Usefulness of the compounds of the present invention as an effective component of a pharmaceutical agent for treating skin cancer can be verified by, for example, examining skin inflammation or skin tumors that are induced by UV irradiation, following subcutaneous administration of the compounds of the present invention to a mouse. Further, usefulness of the compounds of the present invention as an effective component of a pharmaceutical agent for treating colon cancer can be verified by, for example, examining the number of aberrant crypt foci in a colon, etc. that are induced by azoxymethane, following oral administration of the compounds of the present invention to a rat. Still further, usefulness of the compounds of the present invention as an effective component of a pharmaceutical agent for treating lung cancer can be verified by, for example, carrying out histological analysis of lung tumors that are induced by 2-amino-1-methyl-6-phenylimidazo[4,5-b]pyridine (PhIP), following oral administration of the compounds of the present invention to a rat.

It has been reported that an EP1 antagonist is effective for a mouse middle cerebral artery occlusion model (Kawano, T., et al., Nat. Med., 12, p 225-22 (2006), Ahmad, A S. et al., Toxicol. Sci., 89, p 265-270 (2006)) and also for the prophylaxis and/or treatment of cerebral infarction. Usefulness of the compounds of the present invention as an effective component of a pharmaceutical agent for the prophylaxis and/or treatment of cerebral infarction can be verified by, for example, carrying out histological analysis (i.e., to determine ratio of area with necrosis) of brain of a mouse who received an operation for occlusion of middle cerebral artery, following oral, intravenous, or intraperitoneal administration of the compounds of the present invention.

It has been reported that an EP1 antagonist is effective for inhibiting formation of mouse osteoclast (Inoue H., et al., J. Endocrinol., 161, p 231-236 (1999), Tsujisawa, T. et al., J. Bone Miner. Res., 20, p 15-22 (2006)), and also useful for improving a bone disorder. Usefulness of the compounds of the present invention as an effective component of a pharmaceutical agent for the prophylaxis and/or treatment of a bone disorder can be verified by, for example, examining their inhibitory effect on formation of osteoclast after adding the compounds of the present invention to cultured bone marrow cells that are stimulated with $1,25(OH)_2$ vitamin $D_3$ or IL-1, etc. and counting the number of cells which are TRAP-positive.

Based on the finding that an EP1 antagonist is effective for a rat gastric mucosa damage model (Hase S. et al., Life Sci., 74, p 629-641 (2003)), it is known that it can be applied for digestive systems. Usefulness of the compounds of the present invention as an effective component of a pharmaceutical agent for digestive systems can be verified by administering orally, intravenously or intraperitoneally the compounds of the present invention to a rat, and then examining their protective effect against gastric mucosa damage caused by administration of histamine and PGE2, by following histological change in the mucosa or determining membrane permeability, etc.

The pharmaceutical agent of the present invention can be prepared as a pharmaceutical agent which includes the compounds of the present invention as an effective component.

For example, when a compound administered as a prodrug or salt thereof is metabolized in a living body to generate the compounds of the formula (1) or pharmaceutically acceptable salts thereof, it is all within the scope of the pharmaceutical agent of the present invention.

Such derivatives that are useful as the compounds of the present invention have excellent safety (i.e., having favorable pharmacology regarding various toxicity and also safety) and pharmacokinetics of a drug, etc., and usefulness as an effective component for a pharmaceutical agent is confirmed.

Examples of safety test include the followings, but are not limited thereto. Cell toxicity test (test using HL60 cell or liver cell, etc.), Genetic Toxicity Test (Ames test, mouse lymphoma TK test, chromosome abnormality test, small nuclear test, etc.), skin sensitization test (Buehler method, GPMT method, APT method, LLNA test, etc.), skin photosensitization test (Adjuvant and Strip method, etc.), safety pharmacology test regarding cardiovascular system (telemetry method, APD method, hERG inhibition evaluation test), safety pharmacology test regarding central nervous system (FOB method, modified Irwin method, etc.), safety pharmacology test regarding respiratory system (measurement using an instrument for measuring respiratory function, measurement using an instrument for determining blood gas analysis, etc.), general toxicity test, sexual reproduction toxicity test, etc.

In addition, regarding a test for pharmacokinetics of a drug, the followings are included, but not limited thereto. Inhibition or induction test regarding cytochrome P450 enzyme, cell permeation test (i.e., a test using CaCO-2 cells or MDCK cells, etc), drug—transporter ATPase assay, oral absorption test, blood concentration time profile test, metabolism test (stability test, metabolic molecular species test, reactivity test, etc.), solubility test (i.e., solubility test based on turbidity, etc.) and the like.

Usefulness of the derivatives that are useful as the compounds of the present invention as an effective component for a pharmaceutical agent can be determined based on a cell toxicity test, for example. Regarding a cell toxicity test, a method using various cultured cells like human pre-leukemia HL-60 cells, primarily-isolated cultured liver cells, neutrophil fraction prepared from human peripheral blood, etc. can be mentioned. Test can be carried out according to the method described below, but it is not limited thereto. Cells are prepared in suspension including $10^5$ to $10^7$ cells/ml. 0.01 mL to 1 mL suspension is aliquoted to a micro tube or a micro plate, etc. Then, a solution including the compounds dissolved therein is added thereto in an amount of $1/100$ to 1 times the cell suspension, followed by culturing in a cell culture medium having final concentration of the compounds at 0.001 µM to 1000 µM under the condition of 37° C., 5% $CO_2$ for 30 minutes to several days. Once the cell culture is completed, cell viability ratio is determined using MTT method or WST-1 method (Ishiyama, M., et al., In Vitro Toxicology, 8,p. 187, 1995), etc. By measuring cell toxicity expressed by the compounds of the present invention, their usefulness as an effective component of a pharmaceutical agent can be confirmed.

Usefulness of the derivatives that are useful as the compounds of the present invention as an effective component for a pharmaceutical agent can be determined based on a Genetic Toxicity Test, for example. Examples of Genetic Toxicity Test include Ames test, mouse lymphoma TK test, chromosome abnormality test, small nuclear test, etc. The Ames test is a method for determining reversion mutation by culturing designated cells such as Salmonella or E. Coli on a culture dish including a chemical compound (see, II-1.Genetic Toxicity Test under "Guidelines for Genetic Toxicity Test", Pharmaceuticals Examination, Vol. 1604, 1999). Further, the mouse lymphoma TK test is a test for determining a mutational property of a gene in which thymidine kinase gene of mouse lymphoma cell L5178Y is used as a target (see, II-3.Mouse Lymphoma TK Test under "Guidelines for Genetic Toxicity Test", Pharmaceuticals Examination, Vol. 1604, 1999;Clive, D. et al., Mutat. Res., 31,pp. 17-29, 1975;Cole, J., et al., Mutat. Res., 111,pp. 371-386, 1983,etc.). Further, the chromosome abnormality test is a method in which mammalian cells are cultured in the presence of a compound and the cells are fixed, and the chromosome is stained and observed to determine any activity which may cause chromosomal abnormality (see, II-2.Chromosome Abnormality Test Using Cultured Mammalian Cells under "Guidelines for Genetic Toxicity Test", Pharmaceuticals Examination, Vol. 1604, 1999). Further, the small nucleus test is a method of determining an ability to form a small nucleus which is caused by chromosomal abnormality, and it includes a method in which rodents are used (i.e., in vivo test, II-4.Small Nucleus Test Using Rodents, under "Guidelines for Genetic Toxicity Test", Pharmaceuticals Examination, Vol. 1604, 1999;Hayashi, M. et al., Mutat. Res., 312,pp. 293-304, 1994;Hayashi, M. et al., Environ. Mol. Mutagen., 35,pp. 234-252, 2000) or cultured cells are used (i.e., in vitro test, Fenech, M. et al., Mutat. Res., 147,pp. 29-36, 1985; Miller, B., et al., Mutat. Res., 392,pp. 45-59, 1997), etc. By running one, two or more tests based on these methods, gene toxicity of the compounds of the present invention can be clearly identified so that their usefulness as an effective component of a pharmaceutical agent can be confirmed.

Usefulness of the derivatives that are useful as the compounds of the present invention as an effective component for a pharmaceutical agent can be determined based on a skin sensitization test, for example. Examples of skin sensitization test include Buehler method (Buehler, E. V. Arch. Dermatol., 91,pp. 171-177, 1965), GPMT method (i.e., Maximization method, Magnusson, B. et al., J. Invest. Dermatol., 52,pp. 268-276, 1969), APT method (i.e., Adjuvant and Patch method, Sato, Y. et al., Contact Dermatitis, 7,pp. 225-237, 1981), wherein a mormot is used for a skin sensitization test. Further, as a skin sensitization method wherein a mouse is used, there is LLNA method (Local Lymph Node Assay method, OECD Guideline for the testing of chemicals 429, skin sensitization 2002; Takeyoshi, M. et al., Toxicol. Lett., 119(3), pp. 203-8, 2001;Takeyoshi, M. et al., J. Appl. Toxicol., 25(2), pp. 129-34, 2005) and the like. By running one, two or more tests based on these methods, skin sensitization property of the compounds of the present invention can be clearly identified so that their usefulness as an effective component of a pharmaceutical agent can be confirmed.

Usefulness of the derivatives that are useful as the compounds of the present invention as an effective component for a pharmaceutical agent can be determined based on a skin photosensitization test, for example. Examples of skin photosensitization test include a test using a mormot (see, Guidelines for Non-clinical test of pharmaceuticals—Explanation, 2002,YAKUJI NIPPO LIMITED 2002, 1-9:Skin Photosensitization Test, etc.). Further, specific methods include adjuvant and strip method (Ichikawa, H. et al., J. Invest. Dermatol., 76,pp. 498-501, 1981), Harber method (Harber, L. C., Arch. Dermatol., 96,pp. 646-653, 1967), Horio method (Horio, T., J. Invest. Dermatol., 67,pp. 591-593, 1976), Jordan method (Jordan, W.P., Contact Dermatitis, 8,pp. 109-116, 1982), Kochever method (Kochever, I. E. et al., J. Invest. Dermatol., 73,pp. 144-146, 1979), Maurer method (Maurer, T. et al., Br. J. Dermatol., 63,pp. 593-605, 1980), Morikawa method (Morikawa, F. et al., "Sunlight and man", Tokyo Univ. Press, Tokyo, pp. 529-557, 1974), Vinson method (Vinson, L. J., J. Soc. Cosm. Chem., 17,pp. 123-130, 1966) and the like. By running one, two or more tests based on these methods, skin photosensitization property of the compounds of the present invention can be clearly identified so that their usefulness as an effective component of a pharmaceutical agent can be confirmed.

Usefulness of the derivatives that are useful as the compounds of the present invention as an effective component for a pharmaceutical agent can be determined by carrying out a safety pharmacology test regarding cardiovascular system. Examples of safety pharmacology test regarding cardiovascular system include a telemetry method (i.e., a method by which compound's effect on an electrocardiogram, heart rate, blood pressure, blood flow amount, and the like is determined under non-anesthetized condition (Shigeru Kanno, Hirokazu Tsubone, Yoshitaka Nakata eds., Electrocardiography, Echocardiography, Blood Pressure, and Pathology test of an Animal for Basic and Clinical Medicine, 2003,published by Maruzen)), APD method (i.e., a method for measuring action potential duration of a myocardial cell, (Muraki, K. et al., AM. J. Physiol., 269,H524-532, 1995;Ducic, I. et al., J. Cardiovasc. Pharmacol., 30(1), pp. 42-54, 1997)), measurement of hERG inhibition (patch clamp method (Chachin, M. et al., Nippon Yakurigaku Zasshi, 119,pp. 345-351, 2002), Binding assay method (Gilbert, J. D. et al., J. Pharm. Tox. Methods, 50, pp. 187-199, 2004), $Rb^+$ efflux assay method (Cheng, C. S. et al., Drug Develop. Indust. Pharm., 28,pp. 177-191, 2002), Membrane potential assay method (Dorn, A. et al., J. Biomol. Screen., 10,pp. 339-347, 2005) etc.) etc. By running one, two or more tests based on these methods, effect of the compounds of the present invention on a cardiovascular system can be clearly identified so that their usefulness as an effective component of a pharmaceutical agent can be confirmed.

Usefulness of the derivatives that are useful as the compounds of the present invention as an effective component for a pharmaceutical agent can be determined by carrying out a safety pharmacology test regarding a central nervous system. Examples of safety pharmacology test regarding a central nervous system include FOB method (i.e., a method for evaluating overall function, Mattson, J. L. et al., J. American College of Technology 15 (3), pp. 239-254, 1996), modified Irwin method (i.e., a method for evaluating general symptoms and behavioral characteristics (Irwin, S. Comprehensive Observational Assessment (Berl.) 13,pp. 222-257, 1968)), etc. By running one, two or more tests based on these methods, effect of the compounds of the present invention on a central nervous system can be clearly identified so that their usefulness as an effective component of a pharmaceutical agent can be confirmed.

Usefulness of the derivatives that are useful as the compounds of the present invention as an effective component for a pharmaceutical agent can be determined by carrying out a safety pharmacology test regarding a respiratory system, for example. Examples of safety pharmacology test regarding a respiratory system include a measurement using an instrument for measuring respiratory function (i.e., a method which measures breathing number, amount of air per single breathing, amount of breathing air per minute or hour, (Drorbaugh, J. E. et al., Pediatrics, 16, pp. 81-87, 1955;Epstein, M. A. et al., Respir. Physiol., 32, pp. 105-120, 1978), or a measurement using a blood gas analyzer (i.e., a method which measures blood gas, hemoglobin oxygen saturation, etc., Matsuo, S. Medicina, 40, pp. 188, 2003), etc. By running one, two or more tests based on these methods, effect of the compounds of the present invention on a respiratory system can be clearly identified so that their usefulness as an effective component of a pharmaceutical agent can be confirmed.

Usefulness of the derivatives that are useful as the compounds of the present invention as an effective component of a pharmaceutical agent can be determined by carrying out a general toxicity test. Specifically, according to a general toxicity test, a compound which is either dissolved or suspended in an appropriate solvent is orally administered or intravenously administered of a single time or multiple times (for several days) to rodents such as rat, mouse, and the like or non-rodents such as monkey, dog and the like as a subject animal, and then animal's general state or any change in clinical chemistry or tissue in terms of pathology, etc. is determined. By identifying general toxicity of a compound based on this method, usefulness of the compounds of the present invention as an effective component for a pharmaceutical agent can be confirmed.

Usefulness of the derivatives that are useful as the compounds of the present invention as an effective component for a pharmaceutical agent can be determined by carrying out a sexual reproduction toxicity test. The test is to determine any side effect caused by a compound on sexual reproduction process by using rodents such as rat, mouse, and the like or non-rodents such as monkey, dog and the like (Guidelines for Non-clinical test of pharmaceuticals—Explanation, 2002, YAKUJI NIPPO LIMITED 2002, 1-6:Sexual Reproduction Toxicity Test, etc.). With respect to a sexual reproduction toxicity test, a test relating to development of an early embryo from fertilization to implantation, a test relating to development before and after birth and an activity of a mother, a test relating to development of an embryo and a fetus (see, [3] Sexual Reproduction Toxicity Test under "Guidelines for Toxicity Test for Pharmaceuticals", Pharmaceuticals Examination, Vol. 1834, 2000), etc. can be mentioned. By identifying sexual reproduction toxicity of the compounds of the present invention based on this method, usefulness of a compound as an effective component for a pharmaceutical agent can be confirmed.

Usefulness of the derivatives that are useful as the compounds of the present invention as an effective component for a pharmaceutical agent can be determined by carrying out an inhibition or induction test of cytochrome P450 enzyme (Gomez-Lechon, M. J. et al., Curr. Drug Metab. 5(5), pp. 443-462, 2004). Examples of the test include a method of determining in vitro an inhibitory effect of a compound on an enzyme activity by using cytochrome P450 enzyme of each molecular species that is either purified from a cell or prepared using a genetic recombinant, or a microsome as a human P450 expression system (Miller, V. P. et al., Ann. N.Y. Acad. Sci., 919,pp. 26-32, 2000), a method of determining expression of cytochrome P450 enzyme for each molecular species or variation in enzyme activity by using a human liver microsome or cell homogenate (Hengstler, J. G. et al., Drug Metab. Rev., 32,pp. 81-118, 2000), a method of examining compound's activity of inducing the enzyme by extracting the RNA from human liver cells that have been exposed to the compound and comparing the amount of mRNA expression with that of a control (Kato, M. et al., Drug Metab. Pharmacokinet., 20(4), pp. 236-243, 2005), etc. By running one, two or more tests based on these methods, effect of the compounds of the present invention on induction or inhibition of cytochrome P450 enzyme can be clearly identified so that their usefulness as an effective component of a pharmaceutical agent can be confirmed.

Usefulness of the derivatives that are useful as the compounds of the present invention as an effective component for a pharmaceutical agent can be determined by carrying out a cell permeation test, for example. Examples of the test include a method of determining compound's ability of penetrating cell membrane under in vitro cell culture system by using CaCO-2,for example (Delie, F. et al., Crit. Rev. Ther. Drug Carrier Syst., 14,pp. 221-286, 1997;Yamashita, S. et al., Eur. J. Pham. Sci., 10,pp. 195-204, 2000;Ingels, F. M. et al., J. Pham. Sci., 92,pp. 1545-1558, 2003), or a method of determining compound's ability of penetrating cell membrane under in vitro cell culture system by using MDCK cell (Irvine, J. D. et al., J. Pham. Sci., 88,pp. 28-33, 1999) etc. By running one, two or more tests based on these methods, the compounds' ability of penetrating cell membrane can be clearly identified so that their usefulness as an effective component of a pharmaceutical agent can be confirmed.

Usefulness of the derivatives that are useful as the compounds of the present invention as an effective component for a pharmaceutical agent can be determined by carrying out a drug transporter ATPase assay using ATP-Binding Cassette (ABC) transporter, for example. Examples of the assay include a method of determining whether or not a compound is a substrate for P-gp by using P-glycoprotein (P-gp) baculovirus expression system (Germann, U. A., Methods Enzymol., 292,pp. 427-41, 1998), etc. Further, determination can be also carried out based on a transport assay using oocytes obtained from *Xenopus laevis*,as a solute carrier (SLC) transporter. With respect to transport assay, oocytes which express OATP2 can be used to confirm whether or not the compound is a substrate for OATP2 (Tamai I. et al., Pharm Res. 2001 September; 18(9): 1262-1269). By identifying the compounds' activity on ABC transporter or SLC transporter based on this method, usefulness of the compounds of the present invention as an effective component for a pharmaceutical agent can be confirmed.

Usefulness of the derivatives that are useful as the compounds of the present invention as an effective component for a pharmaceutical agent can be determined by carrying out oral absorptivity test, or example. Examples of the assay include a method of determining blood transfer property of a compound after oral administration using LC-MS/MS method by preparing a certain amount of a compound dissolved or suspended in a solvent, orally administering it to a rodent, a monkey or a dog and measuring blood concentration of the compound over time (Harada Kenichi et al., eds. "Newest aspects in mass spectrometry for biological sciences", 2002,Kodansha Scientific, etc.). By identifying compound's oral absorptivity based on this method, usefulness of the compounds of the present invention as an effective component for a pharmaceutical agent can be confirmed.

Usefulness of the derivatives that are useful as the compounds of the present invention as an effective component for a pharmaceutical agent can be determined by carrying out a blood concentration time profile test, for example. Examples of the test include a method of determining blood concentration profile of a compound using LC-MS/MS method by orally or parenterally (e.g., intravenous, intramuscular, intraperitoneal, subcutaneous, or trans-dermal administration, or administration into an eye or via nose, etc.) administering the compound to a rodent, a monkey or a dog and measuring blood concentration of the compound over time (Harada Kenichi et al., eds. "Newest aspects in mass spectrometry for biological sciences", 2002,Kodansha Scientific, etc.). By identifying compound's blood concentration time profile based on this method, usefulness of the compounds of the present invention as an effective component for a pharmaceutical agent can be confirmed.

Usefulness of the derivatives that are useful as the compounds of the present invention as an effective component for a pharmaceutical agent can be determined by carrying out a metabolism test, for example. Examples of the test include a method of determining stability in blood (i.e., a method by which in vivo metabolism clearance of a compound is calculated by measuring its metabolism rate in a liver microsome of a humor other animal; Shou, W. Z. et al., J. Mass Spectrom., 40(10), pp. 1347-1356, 2005;Li, C. et al., Drug Metab. Dispos., 34(6), 901-905, 2006), a metabolite molecular species test, a reactive metabolite testing method, etc. By running one, two or more tests based on these methods, the compounds' metabolic profile can be clearly identified so that their usefulness as an effective component of a pharmaceutical agent can be confirmed.

Usefulness of the derivatives that are useful as the compounds of the present invention as an effective component for a pharmaceutical agent can be determined by carrying out a dissolution test, for example. Examples of the test include a method of determining solubility based on turbidity (Lipinski, C. A. et al., Adv. Drug Deliv. Rev., 23,pp. 3-26, 1997; Bevan, C. D. et al., Anal. Chem., 72, pp. 1781-1787, 2000), etc. By identifying compound's dissolution property based on this method, usefulness of the compounds of the present invention as an effective component for a pharmaceutical agent can be confirmed.

Usefulness of the derivatives that are useful as the compounds of the present invention as an effective component for a pharmaceutical agent can be determined by examining problems associated with an upper gastrointestinal tract or a kidney, etc., for example. With respect to a pharmacological test for an upper gastrointestinal tract, compound's effect on gastric mucosal membrane using a fasted rat model having damaged gastric mucosal membrane can be mentioned. With respect to a pharmacological test for kidney function, a method of measuring renal blood flow amount and glomerular filtration rate [Physiology, $18^{th}$ ed. Bunkoto, 1986,Chapter 17] can be mentioned. By running one, two or more tests based on these methods, the compounds' effect on an upper gastrointestinal tract or a kidney function can be clearly identified so that their usefulness as an effective component of a pharmaceutical agent can be confirmed.

With respect to the pharmaceutical agent of the present invention, the compounds of the present invention or a mixture including two or more kinds of them can be used by themselves. However, it is preferable that to the compounds of the present invention or to a mixture including two or more kinds of them, one or at least two kinds of pharmacologically acceptable carriers are added to prepare a pharmaceutical composition for administration. Types of the pharmacologically acceptable carriers are not specifically limited, but include an excipient, a binder, a disintegrating agent, a lubricating agent, or an additive, etc. Examples of an excipient include D-mannitol and the like. Examples of a binding agent include carboxymethylcellulose and the like. Examples of a disintegrating agent include cornstarch and the like. Examples of a lubricating agent include glycerin and the like. Examples of an additive include para oxybenzoic acid ester, and the like. Further, examples of an additive include a surfactant like polyoxyethylene sorbitan monooleate (Tween 80), HC60 and the like.

When the pharmaceutical agent of the present invention is administered to a human, it can be orally administered in form a tablet, powder, a granule, a capsule, a sugar-coated tablet, a liquid or syrup, etc. Further, it can be also administered via parenteral route in form including an injection solution, a linger's solution, a suppository, a trans-dermal or absorbing agent, etc.

Administration period of the pharmaceutical agent of the present invention is not specifically limited. However, when it is administered under the purpose of treatment, a period during which clinical sign of a disorder is found can be taken as a time period for the administration. In general, the administration is continued from several weeks to one year. However, depending on symptoms, it can be further administered, or can be continuously administered even after recovery from clinical symptoms. In addition, even when no clinical signs are observed, it can be administered for a prophylactic purpose based on clinician's judgment. Dosage of the pharmaceutical agent of the present invention is not specifically limited. For example, it can be generally in an effective amount of 0.01 to 2000 mg per day for an adult, a single or divided in several portions. Administration frequency can be from once a month to everyday. Preferably, it is once a week to three times a week, or five times a week, or can be administered everyday. Single time dosage, administration period, and administration frequency, etc. may be either increased or decreased according to age, body weight, overall health of a subject, or disorder to be treated and severeness of the disorder.

Combining the compounds of the present invention with other pharmaceutical agents and using the combination within the limit that advantageous effect such as obtainment of a desired pharmaceutical effect at maximum level and/or reduced side effect also fall within the scope of the present invention. Examples of a pharmaceutical agent which can be used in combination of the compounds of the present invention to supplement or enhance the prophylactic and/or therapeutic activity of the compounds of the present invention for an overactive bladder include an anti-cholinergic agent, an $\alpha1$ inhibitor, an agonist for $\beta3$ receptor, an antagonist for neurokinin receptor, a calcium channel opener, an antagonist for P2X3 receptor, a blocker for serotonin 1A receptor, a blocker for NMDA receptor, an agent for inhibiting synthesis of prostaglandin, imipramine hydrochloride, flavoxate hydrochloride, capsaicin, resiniferatoxin, botulinum toxin, an anti-diuretic agent and the like.

The anti-cholinergic agent used for the present invention is an antagonist for muscarinic receptor, and for example, the antagonistic agent for muscarinic receptor that is descried in the literature (Yakurigaku Zasshi, 126, p 199-206 (2006)) is preferable. Specifically, oxybutynin, propiverine, tolterodine, solifenacin and imidafenacin can be mentioned as a preferred example. Among these, propiverine, tolterodine or solifenacin is particularly preferred.

The $\alpha1$ inhibitor used for the present invention is an inhibitor for adrenaline $\alpha1$ receptor and examples include the inhibitor for adrenaline $\alpha1$ receptor that is disclosed in the literature (Yakurigaku Zasshi, 126,p 199-206 (2006)). Specific examples include prazosin, terazosin, tamsulosin, naftopidil, alfuzosin, doxazosin, or silodosin. Among these, tamsulosin, naftopidil, or silodosin is particularly preferred.

Administration time for the above described agents for combination use is not specifically limited. The pharmaceutical agent of the present invention and the agents for combination use can be administered to a subject either simultaneously or with a time interval. Dose of the agents for combination use can be similar to those that are clinically used. It can be appropriately selected according to a subject to be administered, an administration route, a disorder to be treated, and type of a combination of the pharmaceutical agent of the present invention and the agents for combination use.

The administration form of the agents for combination use is not specifically limited as long as the pharmaceutical agent of the present invention and the agents for combination use are present as a combination at the time of administration. Such administration form includes, for example 1) administering a single formulation that is obtained by the formulating the compounds of the present invention as an effective component of the pharmaceutical agent of the present invention together with the agents for combination use, 2) administering simultaneously two kinds of the formulations that are obtained by separate formulation of the pharmaceutical agent of the present invention and the agents for combination use via the same administration route, 3) administering with time interval two kinds of the formulations that are obtained by separate formulation of the pharmaceutical agent of the present invention and the agents for combination use via the same administration route, 4) administering simultaneously two kinds of the formulations that are obtained by separate formulation of the pharmaceutical agent of the present invention and the agents for combination use via different administration routes, and 5) administering with time interval two kinds of the formulations that are obtained by separate formulation of the pharmaceutical agent of the present invention and the agents for combination use via different administration routes (for example, the pharmaceutical agent of the present invention is administered first followed by the administration of the agents for combination use, and vice versa) and the like.

The mixing ratio between the pharmaceutical agent of the present invention and the agents for combination use can be appropriately selected according to a subject to be administered, an administration route, a disorder to be treated, and the like.

EXAMPLE

Herein below, the present invention will be explained in greater detail in view of the Examples. However, scope of the present invention is not limited to them.

Regarding the Examples described below, various analysis was carried out according to the following descriptions, unless specifically described otherwise.

For thin layer chromatography (TLC), TLC plate manufactured by Merck Co., Germany was used (Precoated Silica Gel 60 F254). After development using chloroform:methanol (1:0 to 1:1), or hexane:ethyl acetate (1:0 to 0:1), UV ray (254 nm or 365 nm) illumination was carried out, followed by chromogenic reaction using iodine vapor, p-anisic aldehyde solution, phosphorous molybdenum acid (ethanol solution), ninhydrin, or dinitrophenyl hydrazine hydrochloride solution for identification. For drying of an organic solvent, anhydrous magnesium sulfate or anhydrous sodium sulfate was used. For column chromatography, multiflap YFLC (manufactured by Yamazen) was used and either Hi-Flash Column (40 µm; manufactured by Yamazen) series or Purif Pack-Si series (manufactured by MORITE) was used as a column. For flash column chromatography, silica gel 60N (globule form, neutral, 40 to 100 µm, manufactured by Kanto Chemical Formula Company, Japan) was used. For preparative thin layer chromatography (herein below, abbreviated as "PTLC"), one or multiple PLC plates of silica gel 60 F254 (20×20 cm, layer thickness 2 mm, manufactured by Merck Co.) were used depending on the amount of a sample. For HPLC purification, LC-10A system (manufactured by Shimadzu Corporation) was used in conjunction with Develosil C-30-UG-5 column (manufactured by NOMURA CHEMICAL CO., LTD). As an elution solution, water-acetonitrile solution including 0.1% acetic acid was used. For the HPLC purification, a target compound was obtained by removing the solvent via freeze drying, unless specifically described otherwise. For nuclear magnetic resonance (NMR) spectrum measurement, AL-300 (FT-NMR, manufactured by JEOL Co.) was used. As a solvent, deuterated chloroform was used, unless specifically described otherwise. For measurement of chemical shift, tetramethylsilane (TMS) was employed as an internal standard. The chemical shift value was expressed in δ (ppm). In addition, a coupling constant was expressed in J (Hz).

As for "LCMS", liquid chromatography mass analysis spectrum (LC-MS) was used to obtain mass spectrum. For the analysis, three apparatuses (A), (B) and (C) described below were used separately.

(A) As a mass spectrometer, ZMD type mass spectrometer (manufactured by Micromass, England) was used and ionization was carried out based on an electrospray method (ESI) for the measurement. The liquid chromatography instrument used was Waters 600 LC system, manufactured by Waters Company. As a separation column, Develosil C30-UG-5 (50× 4.6 mm, manufactured by NOMURA CHEMICAL CO., LTD) was used.

(B) As a mass spectrometer, Platform-LC type mass spectrometer (manufactured by Micromass, England) was used and ionization was carried out based on an electrospray method (ESI) for the measurement. The liquid chromatography instrument manufactured by GILSON, France was used. As a separation column, Develosil C30-UG-5 (50×4.6 mm, manufactured by NOMURA CHEMICAL CO., LTD) was used.

(C) As a mass spectrometer, Quadrupole type mass spectrometer, i.e., UPLC/SQD system (manufactured by Waters Company) was used and ionization was carried out based on an electrospray method (ESI) for the measurement. The liquid chromatography instrument used was Acquity Ultra Performance LC system, manufactured by Waters Company. As a separation column, ACQUITY UPLC BEH (C18 2.1×50 mm 1.7 μm, manufactured by Waters Company) was used.

With respect to the Examples and the Reference examples in which specific descriptions are given for LC condition, the measurements were carried out by using any one of the above described apparatuses and in accordance with the following solvent condition. In addition, "m/z" indicates mass spectrum data (both M+H and M−H are described).

LC condition 1:(A-1)
Apparatus used: (A)
Flow rate: 2 ml/min
Solvent: Solution A=water including 0.1% (v/v) acetic acid, Solution B=acetonitrile including 0.1% (v/v) acetic acid
From 0 minute to 5 minutes: Linear gradient from [Solution A 95%+Solution B 5% (v/v)] to [Solution A 2%+Solution B 98% (v/v)]
From 5 minutes to 6 minutes: Maintain at [Solution A 2%+Solution B 98% (v/v)]
From 6 minutes to 7.5 minutes: Maintain at [Solution A 95%+Solution B 5% (v/v)]
LC condition 2:(B-1)
Apparatus used: (B)
Solvent: Solution A=water including 0.1% (v/v) acetic acid, Solution B=acetonitrile including 0.1% (v/v) acetic acid
From 0 minute to 5 minutes: Linear gradient from [Solution A 95%+Solution B 5% (v/v)] to [Solution A 0%+Solution B 100% (v/v)]
From 5 minutes to 9 minutes: Maintain at [Solution A 0%+Solution B 100% (v/v)]
From 9 minutes to 10 minutes: Maintain at [Solution A 95%+Solution B 5% (v/v)]
LC condition: (C-1)
Apparatus used: (C)
Flow rate: 0.6 ml/min
Solvent: Solution A=water including 0.1% (v/v) acetic acid, Solution B=acetonitrile including 0.1% (v/v) acetic acid
From 0 minute to 2 minutes: Linear gradient from [Solution A 95%+Solution B 5% (v/v)] to [Solution A 10%+Solution B 90% (v/v)]
From 2 minutes to 2.5 minutes: Linear gradient from [Solution A 10%+Solution B 90% (v/v)] to [Solution A 2%+Solution B 98% (v/v)]
From 2.5 minutes to 2.6 minutes: Linear gradient from [Solution A 2%+Solution B 98% (v/v)] to [Solution A 95%+Solution B 5% (v/v)]
From 2.6 minutes to 3.2 minutes: Maintain at [Solution A 95%+Solution B 5% (v/v)]
LC condition: (A-2)
Apparatus used: (A)
Flow rate: 2 ml/min
Solvent: Solution A=water including 0.1% (v/v) acetic acid, Solution B=acetonitrile including 0.1% (v/v) acetic acid
From 0 minutes to 5 minutes: Linear gradient from [Solution A 50%+Solution B 50% (v/v)] to [Solution A 2%+Solution B 98% (v/v)]
From 5 minutes to 6 minutes: Maintain at [Solution A 2%+Solution B 98% (v/v)]
From 6 minutes to 7.5 minutes: Maintain at [Solution A 50%+Solution B 50% (v/v)]

Reference Example 1

3,5-Diphenyl-1H-pyrazole

To ethanol (22 mL, manufactured by Wako Pure Chemical Industries, Ltd.) solution of 1,3-diphenyl-1,3-propanedione (500 mg, manufactured by Tokyo Chemical Industry Co., Ltd.), hydrazine hydrate (228 mg, manufactured by Tokyo Chemical Industry Co., Ltd.) was added and stirred for one hour at room temperature. To the reaction solution, water (20 mL) was added followed by extraction with ethyl acetate (3×20 mL), washing with brine (20 mL) and drying over $MgSO_4$. The solvent was evaporated. The obtained residue was purified by silica gel column chromatography (hexane: ethyl acetate=8:1) to give the title compound (480 mg). LC-MS: HPLC retention time 4.63 minutes, m/z 221(M+H), Condition A-1.

Reference Example 2

1-{3-(Methoxymethoxy)phenyl} propan-1-ol

To tetrahydrofuran (80 mL, manufactured by Wako Pure Chemical Industries, Ltd.) solution of 3-(methoxymethoxy) benzaldehyde (2.0 g) which had been synthesized according to the method of the literature (B. Michael et al., Org. Lett. 2006, 8, 3745-3748), ethyl magnesium bromide (24 mL, 0.91M tetrahydrofuran solution, manufactured by Kanto Chemical Formula Company) was added at 0° C. followed by stirring at room temperature for 1 hour. To the reaction solution, water (50 mL) was added followed by extraction with ethyl acetate (3×50 mL), washing with brine (100 mL) and drying over $MgSO_4$. The solvent was evaporated to give the title compound (1.65 g).

Reference Example 3

1-{3-(Methoxymethoxy)phenyl}propan-1-one

To dichloromethane (80 mL, manufactured by Wako Pure Chemical Industries, Ltd.) solution of the compound of Reference Example 2 (1.65 g), pyridinium chlorochromate (3.62 g, manufactured by Acros Organics) was added followed by stirring at room temperature for 3 hours. Upon the completion of the reaction, unreacted pyridinium chlorochromate was removed by filtration, water (50 mL) was added to the filtrate followed by extraction with ethyl acetate (3×50 mL), washing with brine (100 mL) and drying over $MgSO_4$. The solvent was evaporated to give the title compound (251 mg).

Reference Example 4

1-{3-(Methoxymethoxy)phenyl}-2-methyl-3-phenyl-propan-1,3-dione

To toluene (13 mL, manufactured by Kanto Chemical Formula Company) solution of the compound of Reference example 3 (251 mg), lithium hexamethyldisilazane (850 μL, 1.6M tetrahydrofuran solution, manufactured by Aldrich Company) was added under ice cooling. After stirring for 1 minute, benzoyl chloride (90 μL, manufactured by Wako Pure Chemical Industries, Ltd.) was added at the same temperature and stirred for 30 minutes. To the reaction solution, 1M hydrochloric acid (10 mL, manufactured by Kanto Chemical Formula Company) was added, followed by extraction with diethyl ether (3×20 mL), washing with brine (40 mL) and drying over $MgSO_4$. The solvent was evaporated to give the title compound (384 mg). LC-MS:HPLC retention time 4.46 minutes, m/z 299 (M+H), Condition B-1.

Reference Example 5

2-Nitroso-1,3-diphenylpropanedione

To dimethyl sulfoxide (158 mL, manufactured by Kanto Chemical Formula Company) solution of 2-bromo-1,3-diphenylpropan-1,3-dione (9.55 g) which had been synthesized according to the method of the literature (T. H. L. Quyen et al., J. Chem. Soc. Dalton Trans., 1997, 643-648), sodium nitrite (10.9 g, manufactured by Aldrich Company) and urea (15.2 g, manufactured by Kanto Chemical Formula Company) were added followed by stirring overnight at room temperature. To the reaction solution, water (200 mL) was added followed by extraction with ethyl acetate (3×200 mL), washing with brine (400 mL) and drying over $MgSO_4$. The solvent was evaporated. The obtained residue was purified by silica gel column chromatography (hexane:ethyl acetate=70:30) to give the title compound (4.25 g). LC-MS:HPLC retention time 1.52 minutes, m/z 252 (M+H), Condition C-1.

Reference Example 6

2-Methyl-3-iodo-3-phenylpropionitrile

To tetrahydrofuran (27 mL, manufactured by Kanto Chemical Formula Company) solution of propionitrile (770 mg, manufactured by Wako Pure Chemical Industries, Ltd.), sodium ethoxide (1.24 g, manufactured by Kanto Chemical Formula Company) was added at room temperature followed by stirring for 5 minutes at room temperature. To the reaction solution, ethyl benzoate (2.32 g, manufactured by Tokyo Chemical Industry Co., Ltd.) was added and refluxed for 12 hours. The reaction solution was cooled to room temperature and 1M hydrochloric acid (20 mL, manufactured by Kanto Chemical Formula Company) was added thereto. The mixture was stirred at the same temperature for 1 hour. The mixture solution was extracted with ethyl acetate (3×20 mL), washed with brine (20 mL) and dried over $MgSO_4$. The solvent was evaporated. The obtained residue was purified by silica gel column chromatography (hexane:ethyl acetate=6:1) to give the title compound (2.06 g). LC-MS:HPLC retention time 4.11 minutes, m/z 158 (M–H), Condition A-1.

Reference Example 7

Ethyl 2-(5-Amino-4-methyl-3-phenyl-1H-pyrazol-1-yl)thiazole-4-carboxylic acid

To ethanol (47 mL, manufactured by Wako Pure Chemical Industries, Ltd.) solution of the compound of Reference example 6 (2.06 g), thiosemicarbazide (1.20 g, manufactured by Tokyo Chemical Industry Co., Ltd.) was added at room temperature followed by reflux under heating for 1 hour. Ethyl bromopyruvic acid (2.16 mL, manufactured by Wako Pure Chemical Industries, Ltd.) was further added and refluxed under heating for 4 hours. The reaction solution was cooled to room temperature and concentrated under reduced pressure. To the obtained residue, water (20 mL) was added followed by extraction with ethyl acetate (3×20 mL), washing with brine (20 mL) and drying over $MgSO_4$. The solvent was evaporated. The obtained residue was purified by silica gel column chromatography (hexane:ethyl acetate=4:1) to give the title compound (679 mg). LC-MS:HPLC retention time 5.44 minutes, m/z 329 (M+H), Condition A-1.

Reference Example 8

Ethyl 2-(5-iodo-4-methyl-3-phenyl-1H-pyrazol-1-yl)thiazole-4-carboxylic acid

To acetonitrile (17 mL, manufactured by Wako Pure Chemical Industries, Ltd.) solution of the compound of Reference example 7 (572 mg), t-butyl nitrous acid (554 μL, manufactured by Acros Organics) and iodine (1.17 g, manufactured by Kanto Chemical Formula Company) were added followed by reflux under heating for 2 hours. The reaction solution was cooled to room temperature and concentrated under reduced pressure. To the obtained residue, saturated aqueous solution of sodium thiosulfate (20 mL) was added followed by extraction with ethyl acetate (3×20 mL), washing with brine (20 mL) and drying over $MgSO_4$. The solvent was evaporated. The obtained residue was purified by silica gel column chromatography (hexane:ethyl acetate=9:1) to give the title compound (495 mg). LC-MS:HPLC retention time 6.05 minutes, m/z 440 (M+H), Condition B-1.

Reference Example 9

Methyl 2-amino-5-methylthiazole-4-carboxylic acid

To N,N-dimethylformamide (10 mL, manufactured by Kanto Chemical Formula Company) solution of methyl 2-amino-5-bromothiazole-4-carboxylic acid (240 mg, manufactured by Combi-Block Company), tetramethyl tin (693 μg, manufactured by Tokyo Chemical Industry Co., Ltd.) and tetrakis triphenyl phosphine palladium (118 mg, manufactured by Kanto Chemical Formula Company) were added and stirred overnight at 120° C. To the reaction solution, water (20 mL) was added followed by extraction with ethyl acetate (2×30 mL), washing with brine (20 mL) and drying over $MgSO_4$. The solvent was evaporated. The obtained residue was purified by silica gel column chromatography (chloroform:methanol=20:1) to give the title compound (43.3 mg). LC-MS:HPLC retention time 1.76 minutes, m/z 173 (M+H), Condition B-1.

Reference Example 10

Methyl 2-bromo-5-methylthiazole-4-carboxylic acid

To acetonitrile (15 mL, manufactured by Kanto Chemical Formula Company) solution of the compound of Reference example 9 (267 mg), t-butyl nitrous acid (493 µL, manufactured by Acros Organics) and copper bromide (II) (915 mg, manufactured by Kanto Chemical Formula Company) were added at room temperature and refluxed under heating for 6 hours. The reaction solution was cooled to room temperature, and water (20 mL) was added followed by extraction with ethyl acetate (2×30 mL), washing with brine (20 mL) and drying over $MgSO_4$. The solvent was evaporated. The obtained residue was purified by silica gel column chromatography (hexane:ethyl acetate=4:1) to give the title compound (277 mg). LC-MS:HPLC retention time 3.30 minutes, m/z 236 (M+H), Condition B-1.

Reference Example 11

Methyl 2-bromo-5-ethylthiazole-4-carboxylic acid

To acetonitrile (20 mL, manufactured by Kanto Chemical Formula Company) solution of methyl 2-amino-5-ethylthiazole-4-carboxylic acid (373 mg, manufactured by Bionet), t-butyl nitrous acid (636 µL, manufactured by Acros Organics) and copper bromide (II) (1.19 g, manufactured by Kanto Chemical Formula Company) were added at room temperature and refluxed under heating for 2.5 hours. The reaction solution was cooled to room temperature, water (10 mL) was added followed by extraction with ethyl acetate (2×30 mL), washing with brine (20 mL) and drying over $MgSO_4$. The solvent was evaporated. The obtained residue was purified by silica gel column chromatography (hexane:ethyl acetate=4:1) to give the title compound (389 mg). LC-MS:HPLC retention time 3.87 minutes, m/z 250 (M+H), Condition B-1.

Reference Example 12

Ethyl 2-{(trimethylsilyl)ethynyl}thiazole-4-carboxylic acid

To tetrahydrofuran (500 µL, manufactured by Kanto Chemical Formula Company) solution of ethyl 2-bromo-4-thiazaol carboxylic acid (213 mg) which had been synthesized according to the method of the literature (T. R. Kelly et al., J. Org. Chem. 1996, 61, 4623-4633), trimethylsilylacetylene (147 mg, manufactured by Tokyo Chemical Industry Co., Ltd.), dichlorobis(triphenylphosphine) palladium (35 mg, manufactured by Kanto Chemical Formula Company), triphenylphosphine (7 mg, manufactured by Wako Pure Chemical Industries, Ltd.) and triethylamine (210 µL, manufactured by Wako Pure Chemical Industries, Ltd.) were added and stirred at the same temperature for 20 minutes. To the reaction solution, copper iodide (8 mg, manufactured by Kanto Chemical Formula Company) was added and further stirred at 60° C. for two hours. The reaction solution was cooled to room temperature, water (10 mL) was added followed by extraction with ethyl acetate (3×10 mL), washing with brine (20 mL) and drying over $MgSO_4$. The solvent was evaporated. The obtained residue was purified by silica gel column chromatography (hexane:ethyl acetate=4:1) to give the title compound (77.7 mg). LC-MS:HPLC retention time 4.91 minutes, m/z 254 (M+H), Condition B-1.

Reference Example 13

Ethyl 2-ethynylthiazole-4-carboxylic acid

To tetrahydrofuran (1.8 mL, manufactured by Kanto Chemical Formula Company) solution of the compound of Reference example 12 (78 mg), tetrabutyl ammonium fluoride (401 mg, manufactured by Tokyo Chemical Industry Co., Ltd.) was added and stirred at room temperature for 1 hour. To the reaction solution, saturated aqueous ammonium chloride solution (10 mL) was added followed by extraction with ethyl acetate (3×10 mL), washing with brine (20 mL) and drying over $MgSO_4$. The solvent was evaporated. The obtained residue was purified by silica gel column chromatography (hexane:ethyl acetate=4:1) to give the title compound (30.5 mg). LC-MS:HPLC retention time 3.06 minutes, m/z 182 (M+H), Condition B-1.

Reference Example 14

Ethyl (Z)-2-(2-bromovinyl)thiazole-4-carboxylic acid

Reference Example 15

Ethyl (E)-2-(2-bromovinyl)thiazole-4-carboxylic acid

To tetrahydrofuran (883 µL, manufactured by Kanto Chemical Formula Company) solution of the compound of Reference example 13 (40 mg), zirconocene chloride hydride (85 mg, manufactured by Tokyo Chemical Industry Co., Ltd.) was added and stirred at the same temperature for 3 hours. Then, bromine (17 mg, manufactured by Wako Pure Chemical Industries, Ltd.) was added and the mixture was further stirred for 2 hours at 0° C. To the reaction solution, saturated aqueous sodium thiosulfate solution (10 mL) was added followed by extraction with ethyl acetate (3×10 mL), washing with brine (20 mL) and drying over $MgSO_4$. The solvent was evaporated. The obtained residue was purified by PTLC (hexane: ethyl acetate=2:1) to give the target compound (i.e., 30 mg of (Z)-form and 15 mg of (E)-form). (Z)-form; LC-MS:HPLC retention time 3.74 minutes, m/z 262 (M+H), Condition B-1.(E)-form; LC-MS:HPLC retention time 3.91 minutes, m/z 262 (M+H), Condition B-1.

Example 1

Ethyl 2-(3,5-diphenyl-1H-pyrazol-1-yl)-thiazole-4-carboxylic acid

To N,N-dimethylformamide (9 mL, manufactured by Kanto Chemical Formula Company) solution of the compound of Reference example 11 (200 mg), sodium hydride (added with 40% mineral oil, 80 mg, manufactured by Kanto Chemical Formula Company) was added under ice cooling and stirred at the same temperature for 15 minutes. Subsequently, to the reaction solution, ethyl 2-bromo-4-thiazole carboxylic acid (648 mg) which had been synthesized according to the method described in the literature (T. R. Kelly et al., J. Org. Chem. 1996, 61, 4623-4633) was added and stirred at 150° C. for 14 hours. The reaction solution was cooled to room temperature. Then water (10 mL) was added followed by extraction with ethyl acetate (3×10 mL), washing with brine (10 mL) and drying over $MgSO_4$. The solvent was evaporated. The obtained residue was purified by silica gel column chromatography (hexane:ethyl acetate=6:1) to give the title compound (149 mg). LC-MS:HPLC retention time 5.67 minutes, m/z 376 (M+H), Condition A-1.

Example 2

2-(3,5-Diphenyl-1H-pyrazol-1-yl)thiazole-4-carboxylic acid

To ethanol (9 mL, manufactured by Wako Pure Chemical Industries, Ltd.) solution of the compound of Example 1 (53 mg), 5M aqueous solution of sodium hydroxide (1 mL, manufactured by Kanto Chemical Formula Company) was added and stirred at room temperature for 12 hours. After adding 5M hydrochloric acid (1 mL, manufactured by Kanto Chemical Formula Company) to the reaction solution, extraction was carried out with ethyl acetate (3×10 mL) followed by washing with brine (10 mL) and drying over $MgSO_4$. The solvent was evaporated. The obtained residue was purified by silica gel column chromatography (hexane:ethyl acetate=1:3) to give the title compound (32.0 mg). LC-MS:HPLC retention time 5.05 minutes, m/z 348 (M+H), Condition A-1.

Example 3

Ethyl 2-(4-hydroxy-3,5-diphenyl-1H-pyrazol-1-yl)thiazole-4-carboxylic acid

To ethanol (50 mL, manufactured by Wako Pure Chemical Industries, Ltd.) solution of 2-hydroxy-1,3-diphenyl-propan-1,3-dione (3.36 g) which had been synthesized according to the method of the literature (A. H. Blatt et. al, J. Am. Chem. Soc. 1936, 58, 81-84.), thiosemicarbazide (1.30 g, manufactured by Tokyo Chemical Industry Co., Ltd.) was added followed by stirring under heating 80° C. for 2 hours. Ethyl bromopyruvic acid (2.33 mL, manufactured by Wako Pure Chemical Industries, Ltd.) was further added to the reaction solution, which was then stirred at 80° C. for 12 hours. The reaction solution was cooled to room temperature. Water (20 mL) was added followed by extraction with ethyl acetate (3×30 mL), washing with brine (30 mL) and drying over $MgSO_4$. The solvent was evaporated. The obtained residue was purified by silica gel column chromatography (hexane:ethyl acetate=5:1) to give the title compound (1.68 g). LC-MS:HPLC retention time 5.37 minutes, m/z 392 (M+H), Condition B-1.

Example 4

Ethyl 2-[4-methoxy-3,5-diphenyl-1H-pyrazol-1-yl]thiazole-4-carboxylic acid

To N,N-dimethylformamide (4 mL, manufactured by Kanto Chemical Formula Company) solution of the compound of Example 3 (20 mg), sodium hydride (added with 40% mineral oil, 50 mg, manufactured by Kanto Chemical Formula Company) was added under ice cooling and stirred at the same temperature for 15 minutes. Subsequently, to the reaction solution, iodomethane (22 mg, manufactured by Tokyo Chemical Industry Co., Ltd.) was added and stirred at the same temperature for 4 hours. Then water (10 mL) was added followed by extraction with diethyl ether (3×10 mL), washing with brine (10 mL) and drying over $MgSO_4$. The solvent was evaporated. The obtained residue was purified by silica gel column chromatography (hexane:ethyl acetate=9:1) to give the title compound (12.8 mg). LC-MS:HPLC retention time 5.64 minutes, m/z 406 (M+H), Condition A-1.

Example 5

Ethyl 2-(4-methyl-3,5-diphenyl-1H-pyrazol-1-yl)thiazole-4-carboxylic acid

To mesitylene (5 mL, manufactured by Kanto Chemical Formula Company) solution of 4-methyl-3,5-diphenyl-1H-pyrazole (1.17 g) which had been synthesized according to the method of the literature (C. Francesca et al., J. Chem. Soc. Perkin Trans. 1 1994, 18, 2533-2536.), potassium phosphate (2.23 g, manufactured by Wako Pure Chemical Industries, Ltd.), (1S, 2S)-(+)-N,N-dimethylcyclohexane-1,2-diamine (71 mg, manufactured by Tokyo Chemical Industry Co., Ltd.), copper iodide (48 mg, manufactured by Kanto Chemical Formula Company) and ethyl 2-bromo-4-thiazole carboxylic acid (1.19 g) which had been synthesized according to the method of the literature (T. R. Kelly et al., J. Org. Chem. 1996, 61, 4623-4633) were added and stirred at 180° C. for 12 hours. The reaction solution was cooled to room temperature. Then water (20 mL) was added followed by extraction with ethyl acetate (3×20 mL), washing with brine (20 mL) and drying over $MgSO_4$. The solvent was evaporated. The obtained residue was purified by silica gel column chromatography (hexane:ethyl acetate=9:1) to give the title compound (313 mg). LC-MS:HPLC retention time 6.06 minutes, m/z 390 (M+H), Condition B-1.

Example 6

2-{3-(3-Hydroxyphenyl)-4-methyl-5-phenyl-1H-pyrazol-1-yl}thiazole-4-carboxylic acid To ethanol (500 μL, manufactured by Wako Pure Chemical Industries, Ltd.) solution of ethyl 2-[3-{3-(methoxymethoxy)phenyl}-4-methyl-5-phenyl-1H-pyrazol-1-yl]thiazole-4-carboxylic acid (40 mg), which had been obtained from the compound of Reference example 4 according to the method of Reference example 1 and then the method of Example 5, 5M hydrochloric acid (0.5 mL, manufactured by Kanto Chemical Formula Company) was added and stirred at room temperature for three hours. To the reaction solution, 5M aqueous sodium hydroxide solution (1 mL, manufactured by Kanto Chemical Formula Company) was added and the mixture was further stirred at room temperature for 3 hours. Then 5M hydrochloric acid (0.5 mL, manufactured by Kanto Chemical Formula Company) was added for neutralization followed by extraction with ethyl acetate (3×10 mL), washing with brine (10 mL) and drying over $MgSO_4$. The solvent was evaporated. The obtained residue was purified by PTLC (hexane:ethyl acetate=1:3) to give the title compound (7.0 mg). LC-MS:HPLC retention time 4.52 minutes, m/z 378 (M+H), Condition A-1.

Example 7

Ethyl 2-(4-amino-3,5-diphenyl-1H-pyrazol-1-yl)thiazole-4-carboxylic acid

To ethanol (20 mL, manufactured by Wako Pure Chemical Industries, Ltd.) solution of the compound of Reference example 5 (500 mg), thiosemicarbazide (734 mg, manufactured by Tokyo Chemical Industry Co., Ltd.) was added followed by stirring under heating 80° C. for 2 hours. Ethyl bromopyruvic acid (328 μL, manufactured by Wako Pure Chemical Industries, Ltd.) was further added and stirred at 80° C. for 12 hours. The reaction solution was cooled to room temperature. Water (20 mL) was added followed by extraction with ethyl acetate (3×30 mL), washing with brine (30 mL) and drying over MgSO$_4$. The solvent was evaporated. The obtained residue was purified by silica gel column chromatography (hexane:ethyl acetate=7:3) to give the title compound (215 mg). LC-MS:HPLC retention time 5.34 minutes, m/z 391 (M+H), Condition B-1.

Example 8

Ethyl 2-(4-chloro-3,5-diphenyl-1H-pyrazol-1-yl) thiazole-4-carboxylic acid

To acetonitrile (800 µL, manufactured by Wako Pure Chemical Industries, Ltd.) solution of the compound of Example 7 (26.8 mg), t-butyl nitrous acid (26 µL, manufactured by Acros Organics) and copper bromide (II) (36 mg, manufactured by Kanto Chemical Formula Company) were added at room temperature and refluxed under heating for 2 hours. The reaction solution was cooled to room temperature, and then saturated aqueous solution of sodium thiosulfate (20 mL) was added followed by extraction with ethyl acetate (3×20 mL), washing with brine (20 mL) and drying over MgSO$_4$. The solvent was evaporated. The obtained residue was purified by silica gel column chromatography (hexane:ethyl acetate=4:1) to give the title compound (12.8 mg). LC-MS:HPLC retention time 6.23 minutes, m/z 410 (M+H), Condition B-1.

Example 9

Ethyl 2-(4-methyl-3-phenyl-5-thiophen-2-yl)thiazole-4-carboxylic acid

To 1,4-dioxane solution (455 µL, manufactured by Kanto Chemical Formula Company) of the compound of Reference example 8 (20 mg), 2M aqueous solution of sodium carbonate (10 µL, manufactured by Kanto Chemical Formula Company) and bis(dibenzylideneacetone)palladium (4.2 mg, manufactured by Aldrich Company), tri-o-tolylphosphine (5.6 mg, manufactured by Kanto Chemical Formula Company), 2-thiophene boronic acid (29 mg, manufactured by Maybridge) were added and stirred at 80° C. for 4 hours. The reaction solution was cooled to room temperature, and then saturated aqueous solution of sodium hydrogen carbonate (1 mL) was added followed by extraction with ethyl acetate (3×5 mL), washing with brine (5 mL) and drying over MgSO$_4$. The solvent was evaporated. The obtained residue was purified by silica gel column chromatography (hexane:ethyl acetate=5:1) to give the title compound (6.9 mg). LC-MS:HPLC retention time 5.92 minutes, m/z 396 (M+H), Condition A-1.

Example 10

Ethyl 2-(1',4-dimethyl-5-phenyl-1'H,2H-3,4'-bipyrazol-2-yl)thiazole-4-carboxylic acid To mixture solution of N,N-dimethylformamide (910 µL, manufactured by Kanto Chemical Formula Company) and water (10:1 mixture) including the compound of Reference example 8 (100 mg), potassium phosphate (145 mg, manufactured by Wako Pure Chemical Industries, Ltd.), tri-o-tolylphosphine (20.8 mg, manufactured by Kanto Chemical Formula Company), bis(dibenzylideneacetone)palladium (21 mg, manufactured by Aldrich Company) and 1-methyl-4-(4,4,5,5-tetramethyl-1,3,2-dioxaborolan-2-yl)-1H-pyrazole (142 mg, manufactured by Boron Molecular) were added and stirred at 80° C. for 12 hours. The reaction solution was cooled to room temperature, and water (20 mL) was added. After stirring at room temperature for one hour, extraction was carried out with ethyl acetate (3×20 mL), followed by washing with brine (20 mL) and drying over MgSO$_4$. The solvent was evaporated. The obtained residue was purified by silica gel column chromatography (hexane:ethyl acetate=6:1) to give the title compound (43.3 mg). LC-MS:HPLC retention time 5.27 minutes, m/z 394 (M+H), Condition B-1.

Example 11

Ethyl 2-(4-methyl-3-phenyl-5-(pyrrolidin-1-yl)-1H-pyrazol-1-yl)thiazole-4-carboxylic acid To N,N-dimethylformamide solution (170 µL, manufactured by Kanto Chemical Formula Company) including the compound of Reference example 8 (30 mg), cesium carbonate (47 mg, manufactured by Wako Pure Chemical Industries, Ltd.), copper iodide (I) (1 mg, manufactured by Kanto Chemical Formula Company), pyrrolidine (10 mg, manufactured by Wako Pure Chemical Industries, Ltd.) and 2-acetyl-cyclohexanone (2 mg, manufactured by Aldrich Company) were added and stirred at 80° C. overnight. The reaction solution was cooled to room temperature, and water (1 mL) was added followed by extraction with ethyl acetate (3×5 mL), washing with brine (5 mL) and drying over MgSO$_4$. The solvent was evaporated. The obtained residue was purified by silica gel column chromatography (hexane:ethyl acetate=5:1) to give the title compound (3.4 mg). LC-MS:HPLC retention time 6.34 minutes, m/z 383 (M+H), Condition B-1.

Example 12

5-(4-Methyl-3,5-diphenyl-1H-pyrazol-1-yl)picolinic acid

To N,N-dimethylacetamide (500 µL, manufactured by Kanto Chemical Formula Company) solution of 4-methyl-3,5-diphenyl-1H-pyrazole (48 mg) which had been synthesized according to the method of the literature (C. Francesca et al., J. Chem. Soc. Perkin Trans. 1 1994, 18, 2533-2536.), potassium phosphate (87.5 mg, manufactured by Wako Pure Chemical Industries, Ltd.), (1S, 2S)-(+)-N,N-dimethylcyclohexane-1,2-diamine (11.7 mg, manufactured by Tokyo Chemical Industry Co., Ltd.), copper iodide (7.8 mg, manufactured by Kanto Chemical Formula Company) and methyl 5-bromo-picolinic acid (44.5 mg, manufactured by Combi-Block Company) were added and the mixture was irradiated with microwave at 185° C. for 45 minutes. The solution was cooled to the room temperature and water (1 mL) was added followed by extraction with ethyl acetate (3×2 mL), washing with brine (5 mL) and drying over MgSO$_4$. The solvent was evaporated. The obtained residue was purified by silica gel column chromatography (hexane:ethyl acetate=85:15) to give the title compound (21.5 mg). LC-MS:HPLC retention time 1.91 minutes, m/z 370 (M+H), Condition C-1.

Example 13

Ethyl 2-{2-(4-methyl-3,5-diphenyl-1H-pyrazol-1-yl) thiazol-4-yl}acetic acid

To mesitylene (500 µL, manufactured by Kanto Chemical Formula Company) solution of ethyl(2-chloro-4-thiazolyl) acetic acid (206 mg) which had been synthesized according to the method of the literature (EP 2002-705433), potassium phosphate (446 mg, manufactured by Wako Pure Chemical Industries, Ltd.), MO-PHOS (35 mg, manufactured by Takasago International Corporation), palladium acetate (11 mg, manufactured by Kanto Chemical Formula Company) and 4-methyl-3,5-diphenyl-1H-pyrazole (234 mg) which had been synthesized according to the method of the literature (C. Francesca et al., J. Chem. Soc. Perkin Trans. 1 1994, 18, 2533-2536.) were added and the mixture was stirred at 180° C. overnight. The reaction solution was cooled to room temperature, and water (1 mL) was added followed by extraction with ethyl acetate (3×2 mL), washing with brine (10 mL) and drying over $MgSO_4$. The solvent was evaporated. The obtained residue was purified by silica gel column chromatography (hexane:ethyl acetate=2:1) to give the title compound (73 mg). LC-MS:HPLC retention time 5.83 minutes, m/z 404 (M+H), Condition B-1.

Example 14

2-{(4-Methyl-3,5-diphenyl-1H-pyrazol-1-yl) methyl}thiazole-4-carboxylic acid

To N,N-dimethylformamide (1 mL, manufactured by Kanto Chemical Formula Company) solution of 4-methyl-3,5-diphenyl-1H-pyrazole (40 mg) which had been synthesized according to the method of the literature (C. Francesca et al., J. Chem. Soc. Perkin Trans. 1 1994, 18, 2533-2536.), sodium hydride (added with 40% mineral oil, 7.5 mg, manufactured by Kanto Chemical Formula Company) was added under ice cooling and stirred at the same temperature for 5 minutes. Subsequently, to the reaction solution, ethyl 2-bromomethylthiazole-4-carboxylic acid (43 mg) which had been synthesized according to the method described in the literature (K. Benno et al., Liebigs. Ann. Chem. 1981, 4, 623-632.) was added and stirred at room temperature overnight. Then, water (1 mL) was added to the reaction solution, followed by extraction with ethyl acetate (3×2 mL), washing with brine (10 mL) and drying over $MgSO_4$. The solvent was evaporated. The obtained residue was purified by PTLC (hexane:ethyl acetate=2:1) to give the tile compound (5.5 mg). LC-MS:HPLC retention time 4.62 minutes, m/z 376 (M+H), Condition B-1.

Reference Example 16

{2-(4-Methyl-3,5-diphenyl-1H-pyrazol-1-yl)-thiazol-4-yl}methanol

To tetrahydrofuran (5 mL, manufactured by Wako Pure Chemical Industries, Ltd.) solution of the compound of Example 5 (182 mg), lithium aluminum hydride (36 mg, manufactured by Kanto Chemical Formula Company) was added under ice cooling and stirred at the same temperature for one hour. To the reaction solution, saturated aqueous solution of ammonium chloride (1 mL) was added dropwise, magnesium sulfate was further added and then the mixture was stirred at room temperature for 1 hour followed by Celite filtration. The solvent was evaporated. The obtained residue was purified by silica gel column chromatography (hexane: ethyl acetate=9:1) to give the title compound (158 mg). LC-MS:HPLC retention time 4.98 minutes, m/z 348 (M+H), Condition B-1.

Reference Example 17

2-(4-Methyl-3,5-diphenyl-1H-pyrazol-1-yl)thiazole-4-carbaldehyde

To dichloromethane (7 mL, manufactured by Kanto Chemical Formula Company) solution of the compound of Reference example 16 (158 mg), Dess-Martin Periodinane (594 mg, manufactured by LANCASTER) was added and then the mixture was stirred at room temperature for 1 hour. Water (10 mL) was added to the reaction solution followed by extraction with dichloromethane (3×10 mL), washing with brine (20 mL) and drying over $MgSO_4$. The solvent was evaporated to give the title compound (91 mg). LC-MS: HPLC retention time 5.66 minutes, m/z 346 (M+H), Condition B-1.

Example 15

Ethyl (E)-3-{2-(4-methyl-3,5-diphenyl-1H-pyrazol-1-yl)thiazol-4-yl}acrylic acid

To tetrahydrofuran (2.6 mL, manufactured by Kanto Chemical Formula Company) solution of the compound of Reference example 17 (91 mg), potassium hexamethyldisilazane (278 μL, 1.9M tetrahydrofuran solution, manufactured by Tokyo Chemical Industry Co., Ltd.) and ethyldiethyl phosphonic acid (105 μL, manufactured by Tokyo Chemical Industry Co., Ltd.) were added at 0° C. and then the mixture was stirred at the same temperature overnight. To the reaction solution, 1M hydrochloric acid (10 mL) was added, followed by extraction with ethyl acetate (3×10 mL), washing with brine (20 mL) and drying over $MgSO_4$. The solvent was evaporated. The obtained residue was purified by silica gel column chromatography (hexane:ethyl acetate=6:1) to give the title compound (57 mg). LC-MS:HPLC retention time 7.14 minutes, m/z 416 (M+H), Condition B-1.

Example 16

Ethyl 3-{2-(4-methyl-3,5-diphenyl-1H-pyrazol-1-yl) thiazol-4-yl}propionic acid

To tetrahydrofuran (200 μL, manufactured by Wako Pure Chemical Industries, Ltd.) and methanol (200 μL, manufactured by Wako Pure Chemical Industries, Ltd.) solution of the compound of Example 15 (17 mg), 10% palladium carbon (18 mg, manufactured by Merck) was added and then the mixture was stirred overnight under hydrogen atmosphere. Upon the completion of the reaction, 10% palladium carbon was removed by filtration and the solvent was evaporated to give the title compound (13.7 mg). LC-MS:HPLC retention time 6.23 minutes, m/z 418 (M+H), Condition B-1.

Example 17

Ethyl 2-{5-(4-aminophenyl)-4-methyl-3-phenyl-1H-pyrazol-1-yl}thiazole-4-carboxylic acid To dichloromethane (500 μL, manufactured by Wako Pure Chemical Industries, Ltd.) solution of ethyl 2-[5-{4-(t-butoxycarbonylamino)phenyl}-4-methyl-3-phenyl-1H-pyrazol-1-yl]thiazole-4-carboxylic acid (18.4 mg) which had been synthesized according to the method of Example 10, trifluoroacetic acid (42 μL, manufactured by Wako Pure Chemical Industries, Ltd.) was added and then the mixture was stirred at room temperature for 3 hours. Then, the solvent was evaporated and the resulting residue was purified by PTLC (hexane:ethyl acetate=2:1) to give the title compound (5.6 mg). LC-MS:HPLC retention time 4.77 minutes, m/z 405 (M+H), Condition A-1.

Example 18

2-{4-Methyl-3-phenyl-5-(1H-pyrrolo-2-yl)-1H-pyrazol-1-yl}-1,3-thiazole-4-carboxylic acid To ethanol (500 μL, manufactured by Wako Pure Chemical Industries, Ltd.) solution of ethyl 2-[5-{1-(t-butoxycarbonyl)-1H-pyrrol-2-yl}-4-methyl-3-phenyl-1H-pyrazol-1-yl] thiazole-4-carboxylic acid (20 mg) which had been synthesized according to the method of Example 10, 5M hydrochloric acid (0.5 mL, manufactured by Kanto Chemical Formula Company) was added and then the mixture was at room temperature for three hours. Then, to the reaction solution, 5M aqueous sodium hydroxide solution (1 mL, manufactured by Kanto Chemical Formula Company) was further added and then the mixture was stirred again for three more hours at the same temperature. 5N hydrochloric acid (0.5 mL, manufactured by Kanto Chemical Formula Company) was added for the neutralization followed by extraction with ethyl acetate (3×10 mL), washing with brine (1 mL) and drying over $MgSO_4$. The solvent was evaporated. The obtained residue was purified by PTLC (hexane:ethyl acetate=2:1) to give the title compound (1.1 mg). LC-MS:HPLC retention time 4.46 minutes, m/z 378 (M+H), Condition A-1.

Example 19

2-{4-Methyl-3-phenyl-5-(1H-pyrrol-3-yl)-1H-pyrazol-1-yl}-1,3-thiazole-4-carboxylic acid To ethanol (500 μL, manufactured by Wako Pure Chemical Industries, Ltd.) solution of ethyl 2-[4-methyl-3-phenyl-5-{1-(triisopropylsilyl)-1H-pyrrol-3-yl}-1H-pyrazol-1-yl] thiazole-4-carboxylic acid (5.2 mg) which had been synthesized according to the method of Example 10, 5M aqueous sodium hydroxide solution (0.5 mL, manufactured by Kanto Chemical Formula Company) was added, and then the mixture was stirred at room temperature for three hours. Then, to the reaction solution, 5M aqueous hydrochloric acid (0.5 mL, manufactured by Kanto Chemical Formula Company) was further added for neutralization followed by extraction with ethyl acetate (3×10 mL), washing with brine (10 mL) and drying over $MgSO_4$. The solvent was evaporated. The obtained residue was purified by silica gel column chromatography (hexane:ethyl acetate=1:3) to give the title compound (1.8 mg). LC-MS:HPLC retention time 5.28 minutes, m/z 351 (M+H), Condition A-1.

Reference Example Nos. 18 to 27

Preparation of the compounds of Reference example Nos. 18 to 27 is described below. Detailed information regarding Reference example Nos. 18 to 27 is given in Table 1. Meaning of the symbols included in Table 1 is as follows.

"Ref."; Reference example number, "Str."; compound of Reference example, "S. M. 1"; starting material for the preparation of a corresponding compound of Reference example. Symbols included in "S. M. 1" column indicate the following starting materials. "IM. 1"; 2-methyl-1,3-diphenylpropan-1,3-dione (prepared according to the method described in Tetrahedron Lett. 43, 2945-2948 (2002)), "IM. 2"; 1-(2-methoxymethoxyphenyl)-3-phenylpropan-1,3-dione (prepared according to the method described in Synthesis 3, 178-183 (1988)). In addition, for the commercially available reagents, they indicate the reagents which correspond to the symbol described in "Reagent" column of Table 2.

"LC-MS" means data obtained from liquid chromatography mass analysis spectrum (m/z). Specifically, it consists of "method", "R. T.", and "MS" described below.

"method"; LCMS condition. Condition "B-1" corresponds to the "LCMS" apparatus and Condition (B-1) described above. Similarly, condition "C-1" corresponds to the "LCMS" apparatus and Condition (C-1) described above.;

"R. T."; retention time in LCMS (unit; min).;

"MS"; mass spectrum data (both M+H and M−H are described), with the proviso that, "N.D" indicates that it was impossible to detect molecular ion peaks.

"Synth. Method"; method for preparing the corresponding compound of Reference example. Symbols included in "Synth. Method" column indicate the preparation methods as described below. "A" is the preparation method shown in Reference example 1, and "D" is the preparation method shown in Reference example 4.

Symbols that are included in Table 2 have meanings as follows.

"Reagent"; symbols which correspond to the reagent that is used in "S. M. 1" column of Table 1, "Structure"; structure of a reagent, "Supl."; supplier of a reagent used: With respect to the manufacturers of the reagents used, they are sometimes described with the following abbreviations—manufactured by Tokyo Chemical Industry Co., Ltd.; "TCI", manufactured by Aldrich Company; "Ald", manufactured by Wako Pure Chemical Industries, Ltd.; "WAKO", manufactured by Alfa Aesar Co.; "AAesar".

TABLE 1

| Ref. | Str. | S.M.1 | Synth. Method | LC-MS method | R.T. | MS |
|------|------|-------|---------------|--------|------|-----|
| 18 | MOMO—⟨phenyl⟩—pyrazole(N-NH)—⟨phenyl⟩ | IM.1 | A | B-1 | 4.60 | 281 (M + H) |
| 19 | ⟨phenyl⟩—pyrazole(N-NH, methyl)—⟨phenyl⟩ | IM.2 | A | B-1 | 4.45 | 235 (M + H) |

TABLE 1-continued

| Ref. | Str. | S.M.1 | Synth. Method | LC-MS method | R.T. | MS |
|---|---|---|---|---|---|---|
| 20 | | Ph1 | D, A | B-1 | 4.58 | 249 (M + H) |
| 21 | | Ph2 | D, A | B-1 | 4.82 | 263 (M + H) |
| 22 | | Ph3 | D, A | B-1 | 4.74 | 263 (M + H) |
| 23 | | Ph4 | D, A | B-1 | 4.86 | 297 (M + H) |
| 24 | | Ph5 | D, A | C-1 | 1.61 | 233 (M + H) |
| 25 | | Ph6 | D, A | C-1 | 1.76 | 247 (M + H) |
| 26 | | Ph7 | D, A | C-1 | 1.72 | 235 (M + H) |
| 27 | | Ph8 | D, A | C-1 | 1.73 | 277 (M + H) |

TABLE 2

| Reagent | Structure | Supl. |
|---|---|---|
| Ph1 | phenyl propyl ketone | TCI |
| Ph2 | phenyl butyl ketone | TCI |
| Ph3 | phenyl isobutyl ketone | TCI |
| Ph4 | 1,2-diphenylethanone | WAKO |
| Ph5 | 1-indanone | TCI |
| Ph6 | 1-tetralone | TCI |
| Ph7 | 3(2H)-benzofuranone | AAesar |
| Ph8 | 7-methoxy-1-tetralone | Ald |

Example Nos. 20 to 128

Preparation of the compounds of Example Nos. 20 to is described below. Detailed information regarding Example Nos. 20 to 128 is given in Table 3. Meaning of the symbols included in Table 3 is as follows.

"Exp."; example number, "Str."; compound of Example, "S. M. 1" and "S. M. 2"; starting materials for the preparation of corresponding compounds of Examples. Symbols described in "S. M. 1" and "S. M. 2" columns indicate the following starting materials. "IM. 3"; 2-fluoro-1,3-diphenyl-propan-1,3-dione (prepared according to the method described in Tetrahedron 45, 6003-6010 (1989)), "IM. 4"; ethyl 2-bromo-4-thiazole carboxylic acid (prepared according to the method described in J. Org. Chem. 61, 4623-4633 (1996)). In addition, when starting materials are the compounds described in Examples or Reference examples of the present invention, they are indicated with such Example number or Reference example number (i.e., "Exp. Example number" for Example number and "Ref. Reference example number" for Reference example number; for example "Ref. 2" indicates the compound of Reference example 2.). In addition, for the commercially available reagents, they indicate the reagents which correspond to the symbols described in "Reagent" column of Table 4. When there is only one starting material, only the corresponding starting material is described.

"LC-MS" means data obtained from liquid chromatography mass analysis spectrum (m/z). Specifically, it consists of "method", "R. T.", and "MS" described below.

"method"; LCMS condition. Condition "A-1" corresponds to the "LCMS" apparatus and Condition (A-1) described above. Similarly, condition "B-1" corresponds to the "LCMS" apparatus and Condition (B-1) described above. Similarly, condition "C-1" corresponds to the "LCMS" apparatus and Condition (C-1) described above. Further, condition "A-2" corresponds to the "LCMS" apparatus and Condition (A-2) described above.;

"R. T."; retention time in LCMS (unit; min).;

"MS"; mass spectrum data (both M+H and M−H are described), with the proviso that, "N.D" indicates that it was impossible to detect molecular ion peaks.

"Synth. Method"; method for preparing the corresponding compound of Example. Symbols included in "Synth. Method" column indicate the preparation methods as described below. "A" is the preparation method shown in Reference example 1, "B" is the preparation method shown in Reference example 2, "C" is the preparation method shown in Reference example 3, "D" is the preparation method shown in Reference example 4, "a" is the preparation method shown in Example 1, "b" is the preparation method shown in Example 2, "c" is the preparation method shown in Example 3, "d" is the preparation method shown in Example 4, "e" is the preparation method shown in Example 5, "f" is the preparation method shown in Example 6, "g" is the preparation method shown in Example 8, "h" is the preparation method shown in Example 9, "i" is the preparation method shown in Example 10, "j" is the preparation method shown in Example 12, and "k" is the preparation method shown in Example 14, and compounds can be synthesized with reference to the corresponding examples.

Symbols included in Table 4 have the meanings as follows.

"Reagent"; symbols which correspond to the reagents used in "S. M. 1" and "S. M. 2" columns of Table 1, "Structure"; structure of reagent, "Supl."; manufacturer of the reagent used: With respect to the manufacturers of the reagents used, they are sometimes described with the following abbreviations—manufactured by Tokyo Chemical Industry Co., Ltd.; "TCI", manufactured by Aldrich Company; "Ald", manufactured by Kanto Chemical Formula Company; "KANTO", manufactured by Wako Pure Chemical Industries, Ltd.; "WAKO", manufactured by Lancaster, Co.; "LANC", manufactured by Acros Organics; "Acros", manufactured by Alfa Aesar Co.; "AAesar", manufactured by Boron Molecule ; "B Mol", manufactured by Combi-Block; "Comb", manufactured by Fluoro Chem; "Fchem", manufactured by Frontier; "Front", manufactured by Ryscor; "Rysc".

Further, abbreviations included in paragraphs and tables have the meanings as follows. Me:methyl, Et:ethyl, CHO: formyl, COOH:carboxy, $NH_2$:amino, $CF_3$:trifluoromethyl, F:fluoro, Cl:chloro, Br:bromo, I:iodo, OMe:methoxy, OH:hydroxy, MOM:methoxymethoxy.

Numbers given before each substituent indicate substitution position. Numbers given with "-" (hyphen) before an aromatic ring indicate substitution position of the aromatic ring. The term "(Z)" described in chemical names or structures indicates that substituents on a double bond are in Z configuration. The term "(E)" indicates that they are in E configuration.

TABLE 3

| Exp. | Str. | S.M.1 | S.M.2 | Synth. Method | LC-MS method | R.T. | MS |
|---|---|---|---|---|---|---|---|
| 20 | | Ref. 18 | IM.4 | a, b | A-1 | 4.32 | 364 (M + H) |
| 21 | | Exp. 3 | — | b | A-1 | 4.50 | 364 (M + H) |
| 22 | | Exp. 4 | — | b | A-1 | 5.08 | 378 (M + H) |
| 23 | | Exp. 3 | Ah1 | d, b | A-1 | 5.56 | 406 (M + H) |
| 24 | | Exp. 3 | Ah2 | d, b | A-1 | 5.43 | 406 (M + H) |

TABLE 3-continued

| Exp. | Str. | S.M.1 | S.M.2 | Synth. Method | LC-MS method | R.T. | MS |
|---|---|---|---|---|---|---|---|
| 25 | | Exp. 3 | Ah3 | d, b | A-1 | 5.82 | 420 (M + H) |
| 26 | | Exp. 3 | Ah4 | d, b | A-1 | 5.82 | 420 (M + H) |
| 27 | | Exp. 3 | Ah5 | d, b | A-1 | 6.03 | 434 (M + H) |
| 28 | | Exp. 3 | Ah6 | d, b | A-1 | 5.68 | 454 (M + H) |

TABLE 3-continued

| Exp. | Str. | S.M.1 | S.M.2 | Synth. Method | LC-MS method | R.T. | MS |
|---|---|---|---|---|---|---|---|
| 29 | | Exp. 3 | Ah7 | d, b | A-1 | 7.21 | 476 (M + H) |
| 30 | | Ref. 19 | IM.4 | e, b | A-1 | 5.23 | 362 (M + H) |
| 31 | | Ref. 20 | IM.4 | a, b | B-1 | 5.24 | 376 (M + H) |
| 32 | | Ref. 21 | IM.4 | e, b | B-1 | 5.42 | 390 (M + H) |
| 33 | | Ref. 22 | IM.4 | e, b | B-1 | 5.36 | 390 (M + H) |

TABLE 3-continued

| Exp. | Str. | S.M.1 | S.M.2 | Synth. Method | LC-MS method | R.T. | MS |
|---|---|---|---|---|---|---|---|
| 34 | | Ref. 23 | IM.4 | e, b | B-1 | 5.35 | 424 (M + H) |
| 35 | | Exp. 7 | — | b | A-1 | 4.30 | 363 (M + H) |
| 36 | | IM.3 | — | c, b | B-1 | 5.32 | 366 (M + H) |
| 37 | | Exp. 8 | — | b | A-1 | 5.35 | 383 (M + H) |
| 38 | | Exp. 7 | — | g, b | A-1 | 5.29 | 425 (M + H) |

TABLE 3-continued

| Exp. | Str. | S.M.1 | S.M.2 | Synth. Method | LC-MS method | R.T. | MS |
|---|---|---|---|---|---|---|---|
| 39 | | Exp. 7 | — | g, b | A-1 | 5.28 | 474 (M + H) |
| 40 | | Ref. 8 | Ba1 | i, b | C-1 | 1.82 | 380 (M + H) |
| 41 | | Ref. 8 | Ba2 | i, b | A-1 | 5.16 | 376 (M + H) |
| 42 | | Ref. 8 | Ba3 | h, b | B-1 | 5.17 | 392 (M + H) |
| 43 | | Ref. 8 | Ba4 | i, b | B-1 | 4.34 | 406 (M + H) |

TABLE 3-continued

| Exp. | Str. | S.M.1 | S.M.2 | Synth. Method | LC-MS method | R.T. | MS |
|---|---|---|---|---|---|---|---|
| 44 | | Ref. 8 | Ba5 | i, b | A-2 | 1.31 | 380 (M + H) |
| 45 | | Ref. 8 | Ba6 | i, b | A-1 | 5.38 | 430 (M + H) |
| 46 | | Ref. 8 | Ba7 | i, b | A-2 | 1.50 | 376 (M + H) |
| 47 | | Ref. 8 | Ba8 | i, b | A-2 | 2.48 | 438 (M + H) |
| 48 | | Ref. 8 | Ba9 | i, b | A-1 | 4.36 | 378 (M + H) |

TABLE 3-continued

| Exp. | Str. | S.M.1 | S.M.2 | Synth. Method | LC-MS method | R.T. | MS |
|---|---|---|---|---|---|---|---|
| 49 | | Ref. 8 | Ba10 | h, b | A-1 | 4.78 | 392 (M + H) |
| 50 | | Ref. 8 | Ba11 | i, b | A-2 | 0.67 | 406 (M + H) |
| 51 | | Ref. 8 | Ba12 | i, b | A-2 | 1.04 | 387 (M + H) |
| 52 | | Ref. 8 | Ba13 | i, b | A-2 | 1.04 | 404 (M + H) |
| 53 | | Ref. 8 | Ba14 | i, b | A-2 | 0.63 | 433 (M + H) |

TABLE 3-continued
| Exp. | Str. | S.M.1 | S.M.2 | Synth. Method | LC-MS method | R.T. | MS |
|---|---|---|---|---|---|---|---|
| 54 | 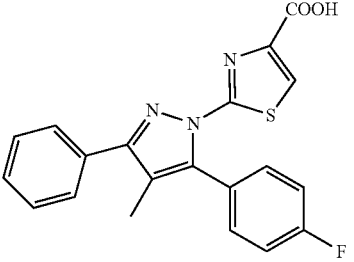 | Ref. 8 | Ba15 | i, b | A-2 | 1.31 | 380 (M + H) |
| 55 | 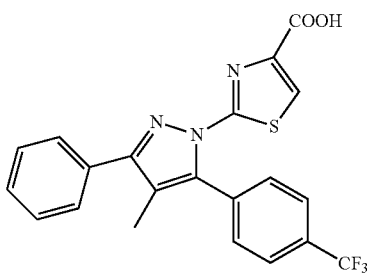 | Ref. 8 | Ba16 | i, b | A-2 | 1.85 | 430 (M + H) |
| 56 | 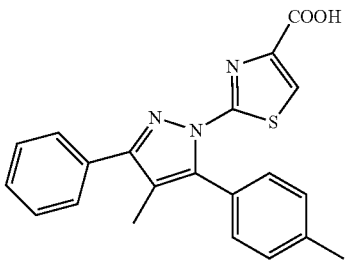 | Ref. 8 | Ba17 | i, b | C-1 | 1.91 | 376 (M + H) |
| 57 | 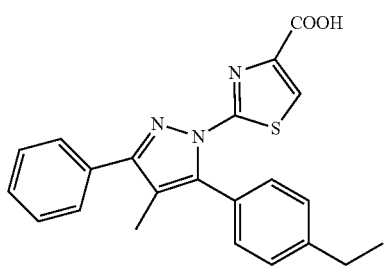 | Ref. 8 | Ba18 | i, b | A-1 | 5.56 | 390 (M + H) |
| 58 | 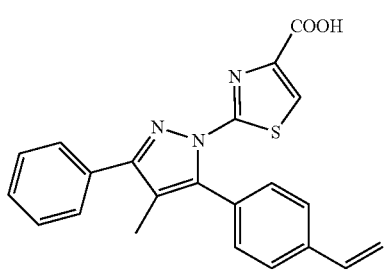 | Ref. 8 | Ba19 | i, b | A-2 | 1.74 | 388 (M + H) |

TABLE 3-continued

| Exp. | Str. | S.M.1 | S.M.2 | Synth. Method | LC-MS method | R.T. | MS |
|---|---|---|---|---|---|---|---|
| 59 | | Ref. 8 | Ba20 | i, b | A-2 | 2.94 | 418 (M + H) |
| 60 | | Ref. 8 | Ba21 | i, b | A-2 | 4.22 | 444 (M + H) |
| 61 | | Ref. 8 | Ba22 | i, b | A-2 | 2.98 | 438 (M + H) |
| 62 | | Ref. 8 | Ba23 | i, b | A-2 | 1.29 | 392 (M + H) |
| 63 | | Ref. 8 | Ba24 | i, b | A-2 | 2.05 | 446 (M + H) |

TABLE 3-continued

| Exp. | Str. | S.M.1 | S.M.2 | Synth. Method | LC-MS method | R.T. | MS |
|---|---|---|---|---|---|---|---|
| 64 | | Ref. 8 | Ba25 | i, b | A-2 | 2.75 | 454 (M + H) |
| 65 | | Ref. 8 | Ba26 | i, b | A-2 | 2.77 | 4.68 (M + H) |
| 66 | | Ref. 8 | Ba27 | i, b | A-2 | 1.29 | 406 (M + H) |
| 67 | | Exp. 17 | — | b | A-1 | 4.36 | 377 (M + H) |
| 68 | | Ref. 8 | Ba28 | i, b | A-2 | 0.69 | 455 (M + H) |

TABLE 3-continued

| Exp. | Str. | S.M.1 | S.M.2 | Synth. Method | LC-MS method | R.T. | MS |
|---|---|---|---|---|---|---|---|
| 69 | | Ref. 8 | Ba29 | i, b | A-2 | 1.72 | 408 (M + H) |
| 70 | | Ref. 8 | Ba30 | i, b | A-2 | 0.58 | 424 (M + H) |
| 71 | | Ref. 8 | Ba31 | i, b | A-2 | 0.72 | 440 (M + H) |
| 72 | | Ref. 8 | Ba32 | i, b | A-1 | 4.44 | 441 (M + H) |
| 73 | | Ref. 8 | Ba33 | i, b | A-2 | 1.10 | 404 (M + H) |

TABLE 3-continued

| Exp. | Str. | S.M.1 | S.M.2 | Synth. Method | LC-MS method | R.T. | MS |
|---|---|---|---|---|---|---|---|
| 74 | | Ref. 8 | Ba34 | i, b | A-2 | 2.30 | 466 (M + H) |
| 75 | | Ref. 8 | Ba35 | i, b | A-2 | 0.51 | 405 (M + H) |
| 76 | | Ref. 8 | Ba36 | i, b | A-2 | 1.47 | 481 (M + H) |
| 77 | | Ref. 8 | Ba37 | i, b | A-2 | 0.72 | 432 (M + H) |
| 78 | | Ref. 8 | Ba38 | i, b | A-2 | 1.11 | 406 (M + H) |

TABLE 3-continued

| Exp. | Str. | S.M.1 | S.M.2 | Synth. Method | LC-MS method | R.T. | MS |
|---|---|---|---|---|---|---|---|
| 79 | | Ref. 8 | Ba39 | i, b | A-2 | 1.10 | 422 (M + H) |
| 80 | | Ref. 8 | Ba40 | i, b | C-1 | 1.88 | 398 (M + H) |
| 81 | | Ref. 8 | Ba41 | i, b | C-1 | 1.81 | 410 (M + H) |
| 82 | | Ref. 8 | Ba42 | i, b | C-1 | 1.87 | 398 (M + H) |
| 83 | | Ref. 8 | Ba43 | i, b | C-1 | 1.87 | 398 (M + H) |

TABLE 3-continued

| Exp. | Str. | S.M.1 | S.M.2 | Synth. Method | LC-MS method | R.T. | MS |
|---|---|---|---|---|---|---|---|
| 84 | | Ref. 8 | Ba44 | i, b | C-1 | 1.88 | 398 (M + H) |
| 85 | | Ref. 8 | Ba45 | i, b | C-1 | 1.91 | 394 (M + H) |
| 86 | | Ref. 8 | Ba46 | i, b | C-1 | 1.94 | 394 (M + H) |
| 87 | | Ref. 8 | Ba47 | h, b | C-1 | 1.83 | 410 (M + H) |
| 88 | | Ref. 8 | Ba48 | h, b | C-1 | 1.86 | 398 (M + H) |

TABLE 3-continued

| Exp. | Str. | S.M.1 | S.M.2 | Synth. Method | LC-MS method | R.T. | MS |
|---|---|---|---|---|---|---|---|
| 89 | | Ref. 8 | Ba49 | h, b | C-1 | 1.92 | 416 (M + H) |
| 90 | | Ref. 8 | Ba50 | h, b | C-1 | 1.92 | 416 (M + H) |
| 91 | | Exp. 9 | — | b | A-1 | 5.18 | 368 (M + H) |
| 92 | | Ref. 8 | Ba51 | h, b | A-1 | 5.02 | 368 (M + H) |
| 93 | | Ref. 8 | Ba52 | i, b | C-1 | 189 | 382 (M + H) |

TABLE 3-continued

| Exp. | Str. | S.M.1 | S.M.2 | Synth. Method | LC-MS method | R.T. | MS |
|---|---|---|---|---|---|---|---|
| 94 | | Ref. 8 | Ba53 | h, b | A-1 | 4.87 | 352 (M + H) |
| 95 | | Ref. 8 | Ba54 | h, b | A-1 | 4.80 | 352 (M + H) |
| 96 | | Ref. 8 | Ba55 | i, b | A-1 | 4.37 | 366 (M + H) |
| 97 | | Ref. 8 | Ba56 | i, b | A-2 | 1.44 | 394 (M + H) |
| 98 | | Ref. 8 | Ba57 | i, b | A-2 | 0.60 | 363 (M + H) |

TABLE 3-continued

| Exp. | Str. | S.M.1 | S.M.2 | Synth. Method | LC-MS method | R.T. | MS |
|---|---|---|---|---|---|---|---|
| 99 | | Ref. 8 | Ba58 | i, b | A-2 | 1.11 | 393 (M + H) |
| 100 | | Ref. 8 | Ba59 | i, b | B-1 | 4.69 | 423 (M + H) |
| 101 | | Ref. 8 | Ba60 | i, b | B-1 | 3.97 | 364 (M + H) |
| 102 | | Ref. 8 | Ba61 | i, b | B-1 | 4.69 | 424 (M + H) |
| 103 | | Ref. 8 | Ba62 | i, b | A-2 | 2.08 | 412 (M + H) |

TABLE 3-continued

| Exp. | Str. | S.M.1 | S.M.2 | Synth. Method | LC-MS method | R.T. | MS |
|---|---|---|---|---|---|---|---|
| 104 | | Ref. 8 | Ba63 | i, b | A-1 | 4.81 | 413 (M + H) |
| 105 | | Ref. 8 | Ba64 | i, b | A-2 | 1.01 | 413 (M + H) |
| 106 | | Ref. 8 | Ba65 | h, b | A-1 | 5.11 | 401 (M + H) |
| 107 | | Ref. 8 | Ba66 | h, b | A-1 | 5.44 | 415 (M + H) |
| 108 | | Ref. 8 | Ba67 | h, b | A-1 | 5.35 | 404 (M + H) |

TABLE 3-continued

| Exp. | Str. | S.M.1 | S.M.2 | Synth. Method | LC-MS method | R.T. | MS |
|---|---|---|---|---|---|---|---|
| 109 | (structure) | Ref. 8 | Ba68 | i, b | A-2 | 1.88 | 402 (M + H) |
| 110 | (structure) | Ref. 8 | Ba69 | i, b | A-2 | 2.02 | 366 (M + H) |
| 111 | (structure) | Ref. 8 | Ba70 | i, b | C-1 | 1.78 | 368 (M + H) |
| 112 | (structure) | Exp. 11 | — | b | C-1 | 0.75 | 355 (M + H) |
| 113 | (structure) | Ref. 8 | Ba71 | i, b | C-1 | 195 | 352 (M + H) |

TABLE 3-continued
| Exp. | Str. | S.M.1 | S.M.2 | Synth. Method | LC-MS method | R.T. | MS |
|---|---|---|---|---|---|---|---|
| 114 | 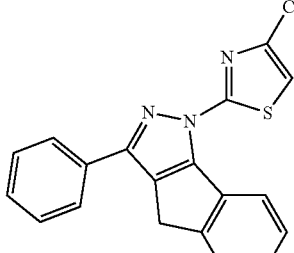 | Ref. 24 | — | e, b | C-1 | 1.70 | 360 (M + H) |
| 115 | 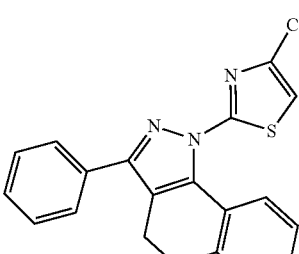 | Ref. 25 | — | e, b | B-1 | 5.35 | 374 (M + H) |
| 116 | 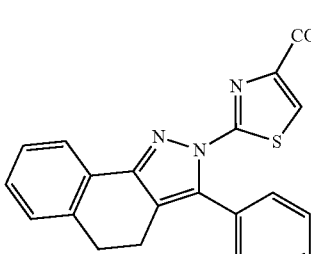 | Ref. 25 | — | e, b | B-1 | 5.50 | 374 (M + H) |
| 117 | 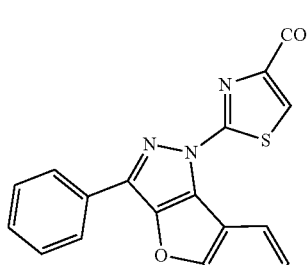 | Ref. 26 | — | e, b | C-1 | 2.11 | 362 (M + H) |
| 118 | 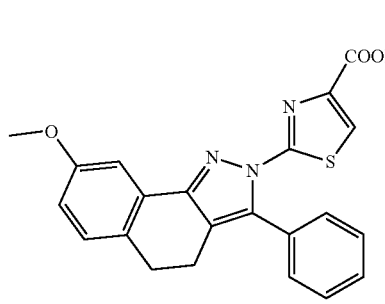 | Ref. 27 | — | e, b | C-1 | 1.92 | 404 (M + H) |

TABLE 3-continued

| Exp. | Str. | S.M.1 | S.M.2 | Synth. Method | LC-MS method | R.T. | MS |
|---|---|---|---|---|---|---|---|
| 119 | | Ref. 19 | Ref. 11 | e, b | B-1 | 5.93 | 390 (M + H) |
| 120 | | Ref. 19 | Ref. 10 | e, b | B-1 | 5.64 | 376 (M + H) |
| 121 | | Ref. 19 | G1 | A, j, b | B-1 | 5.33 | 361 (M + H) |
| 122 | | Ref. 19 | G2 | A, j, b | C-1 | 1.02 | 356 (M + H) |
| 123 | | Ref. 19 | G3 | A, j, b | C-1 | 1.79 | 356 (M + H) |

TABLE 3-continued

| Exp. | Str. | S.M.1 | S.M.2 | Synth. Method | LC-MS method | R.T. | MS |
|---|---|---|---|---|---|---|---|
| 124 | | Exp. 13 | — | b | A-1 | 5.11 | 376 (M + H) |
| 125 | | Exp. 15 | — | b | A-1 | 5.54 | 388 (M + H) |
| 126 | | Exp. 16 | — | b | A-1 | 5.24 | 390 (M + H) |
| 127 | | Ref. 19 | Ref. 14 | A, d, b | A-1 | 5.20 | 388 (M + H) |
| 128 | | Ref. 19 | Ref. 15 | A, d, b | A-1 | 5.14 | 388 (M + H) |

TABLE 4

| Reagent | Structure | Supl. |
|---|---|---|
| Ah1 | n-propyl iodide | TCI |
| Ah2 | isopropyl iodide | TCI |
| Ah3 | n-butyl iodide | KANTO |
| Ah4 | isobutyl iodide | TCI |
| Ah5 | isopentyl iodide | KANTO |
| Ah6 | benzyl bromide | Ald |
| Ah7 | n-octyl iodide | KANTO |
| Ba1 | 2-fluorophenylboronic acid | Ald |
| Ba2 | 2-methylphenylboronic acid | Ald |
| Ba3 | 2-methoxyphenylboronic acid | Ald |
| Ba4 | 2-(methoxycarbonyl)phenylboronic acid | WAKO |
| Ba5 | 3-fluorophenylboronic acid | Ald |
| Ba6 | 3-(trifluoromethyl)phenylboronic acid | WAKO |
| Ba7 | 3-methylphenylboronic acid | Ald |
| Ba8 | 3-biphenylboronic acid | Ald |
| Ba9 | 3-hydroxyphenylboronic acid | Comb |
| Ba10 | 3-(hydroxymethyl)phenylboronic acid | Ald |
| Ba11 | 3-(methoxycarbonyl)phenylboronic acid | Comb |
| Ba12 | 3-cyanophenylboronic acid | Comb |
| Ba13 | 3-acetylphenylboronic acid | Ald |
| Ba14 | 3-(N,N-dimethylcarbamoyl)phenylboronic acid | LANC |
| Ba15 | 4-fluorophenylboronic acid | TCI |

TABLE 4-continued

| Reagent | Structure | Supl. |
|---|---|---|
| Ba16 | 4-(trifluoromethyl)phenylboronic acid | WAKO |
| Ba17 | 4-methylphenylboronic acid | Ald |
| Ba18 | 4-ethylphenylboronic acid | Ald |
| Ba19 | 4-vinylphenylboronic acid | TCI |
| Ba20 | 4-tert-butylphenylboronic acid | LANC |
| Ba21 | 4-cyclohexylphenylboronic acid | LANC |
| Ba22 | biphenyl-4-ylboronic acid | LANC |
| Ba23 | 4-methoxyphenylboronic acid | Ald |
| Ba24 | 4-(trifluoromethoxy)phenylboronic acid | Ald |
| Ba25 | 4-phenoxyphenylboronic acid | Ald |
| Ba26 | 4-(benzyloxy)phenylboronic acid | LANC |
| Ba27 | 4-(methoxymethyl)phenylboronic acid | Front |
| Ba28 | 4-(methylsulfonamido)phenylboronic acid | Rysc |
| Ba29 | 4-(methylthio)phenylboronic acid | Ald |
| Ba30 | 4-(methylsulfinyl)phenylboronic acid | LANC |
| Ba31 | 4-(methylsulfonyl)phenylboronic acid | Acros |
| Ba32 | 4-(4,4,5,5-tetramethyl-1,3,2-dioxaborolan-2-yl)benzenesulfonamide | Front |

TABLE 4-continued

| Reagent | Structure | Supl. |
|---|---|---|
| Ba33 | 4-acetylphenylboronic acid | WAKO |
| Ba34 | 4-benzoylphenylboronic acid | WAKO |
| Ba35 | 4-carbamoylphenylboronic acid | Rysc |
| Ba36 | 4-(phenylcarbamoyl)phenylboronic acid | Comb |
| Ba37 | 4-[(E)-3-methoxy-3-oxoprop-1-en-1-yl]phenylboronic acid | Comb |
| Ba38 | benzo[d][1,3]dioxol-5-ylboronic acid | Ald |
| Ba39 | 2,4-dimethoxyphenylboronic acid | Ald |
| Ba40 | 3,5-difluorophenylboronic acid | Ald |
| Ba41 | 5-fluoro-2-methoxyphenylboronic acid | Ald |
| Ba42 | 2,4-difluorophenylboronic acid | Ald |
| Ba43 | 2,3-difluorophenylboronic acid | Ald |
| Ba44 | 3,4-difluorophenylboronic acid | Ald |
| Ba45 | 4-fluoro-2-methylphenylboronic acid | WAKO |
| Ba46 | 4-fluoro-3-methylphenylboronic acid | Ald |
| Ba47 | 3-fluoro-4-methoxyphenylboronic acid | WAKO |
| Ba48 | 2,5-difluorophenylboronic acid | Ald |

TABLE 4-continued
| Reagent | Structure | Supl. |
|---|---|---|
| Ba49 | 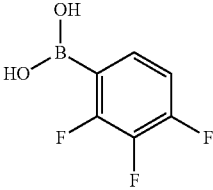 | Ald |
| Ba50 | 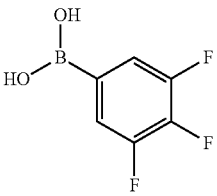 | WAKO |
| Ba51 | 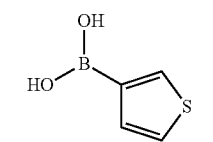 | LANC |
| Ba52 | 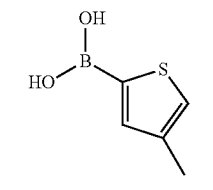 | Front |
| Ba53 | 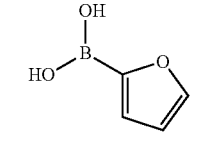 | TCI |
| Ba54 | 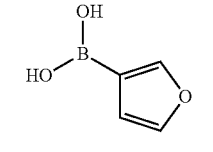 | Ald |
| Ba55 | 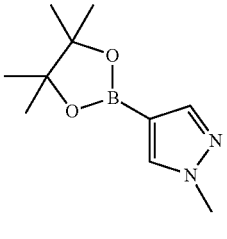 | BMol |
| Ba56 | 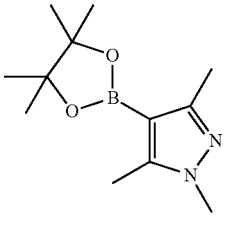 | BMol |
| Ba57 | 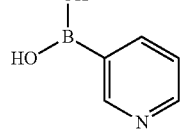 | WAKO |
| Ba58 | 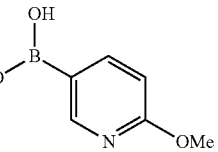 | WAKO |
| Ba59 | 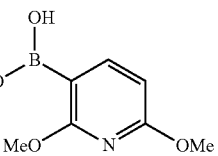 | BMol |
| Ba60 | 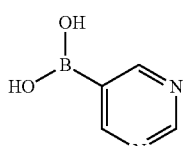 | Front |
| Ba61 | 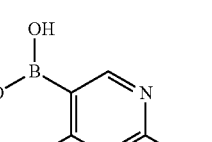 | Front |
| Ba62 | 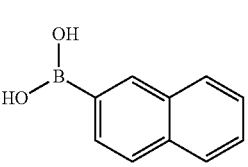 | TCI |
| Ba63 | 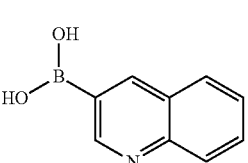 | WAKO |
| Ba64 | 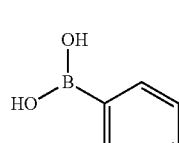 | Front |
| Ba65 | 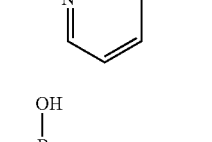 | Front |

TABLE 4-continued

| Reagent | Structure | Supl. |
|---|---|---|
| Ba66 | 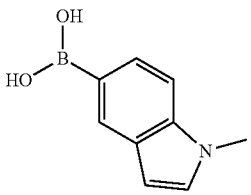 | WAKO |
| Ba67 | 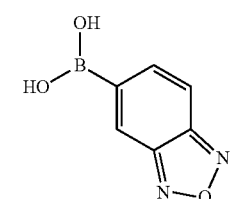 | Front |
| Ba68 | 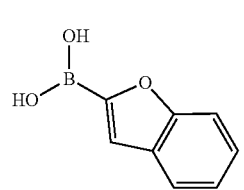 | LANC |
| Ba69 | 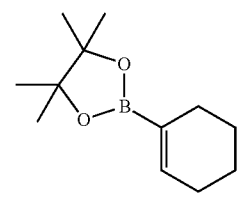 | WAKO |
| Ba70 | 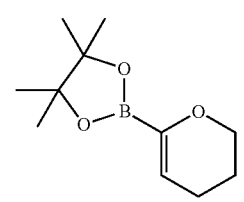 | Front |
| Ba71 | 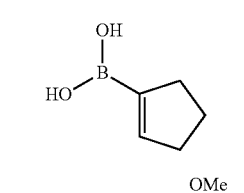 | Comb |
| G1 | 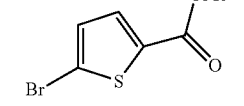 | AAesar |
| G2 | 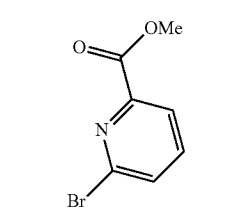 | Ald |
| G3 | 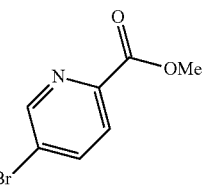 | Comb |

Example 129

Methyl 2-(4-amino-3,5-diphenyl-1H-pyrazol-1-yl)thiazole-4-carboxylic acid

To methanol (10 mL, manufactured by Wako Pure Chemical Industries, Ltd.) solution of the compound of Example 30 (250 mg), para-toluene sulfonic acid hydrate (12 mg, manufactured by Tokyo Chemical Industry Co., Ltd.) was added. After stirring at room temperature for 1 hour, hydrazine hydrate (73 µL, manufactured by Tokyo Chemical Industry Co., Ltd.) was added and refluxed overnight. The solvent was evaporated. The obtained residue was purified by silica gel column chromatography (hexane:ethyl acetate=70:30) to give the title compound (259 mg). LC-MS:HPLC retention time 1.43 minutes, m/z (M+H) 377, Condition C-1.

Example 130

Methyl 2-{4-(methylamino)-3,5-diphenyl-1H-pyrazol-1-yl}thiazole-4-carboxylic acid

Example 131

Methyl 2-{4-(dimethylamino)-3,5-diphenyl-1H-pyrazol-1-yl}thiazole-4-carboxylic acid To dichloroethane (350 µL, manufactured by Kanto Kagaku Company) solution of the compound of Example 4 (50 mg), 36% aqueous solution of formaldehyde (33 mg, manufactured by Kanto Kagaku Company) was added. After stirring at room temperature for 1 hour, the solvent of the reaction solution was evaporated. Then, dichloroethane (350 µL, manufactured by Kanto Kagaku Company), acetic acid (100 µL, manufactured by Wako Pure Chemical Industries, Ltd.), and sodium triacetoxy boron hydride (89 mg, manufactured by Aldrich Company) were added and the mixture was stirred at room temperature overnight. Water (10 mL) was added to the reaction solution followed by extraction with ethyl acetate (3×10 mL), washing with brine (10 mL) and drying over MgSO$_4$. The solvent was evaporated. The obtained residue was purified by silica gel column chromatography (hexane:ethyl acetate=9:1). As a result, a monomethyl form and a dimethyl form, as a highly polar or a weakly polar compound, were obtained in an amount of 4.5 mg and 11.7 mg, respectively. Monomethyl form (Example 130): LC-MS:HPLC retention time 1.70 minutes, m/z (M+H) 391, Condition C-1. Dimethyl form (Example 131): LC-MS:HPLC retention time 2.03 minutes, m/z (M+H) 405, Condition C-1.

Example 132

Methyl 2-(4-iodo-3,5-diphenyl-1H-pyrazol-1-yl)thiazole-4-carboxylic acid

To acetonitrile (5.0 mL, manufactured by Wako Pure Chemical Industries, Ltd.) solution of the compound of Example 4 (200 mg), t-butyl nitrous acid (191 μL, manufactured by Acros Organics) and iodine (405 mg, manufactured by Kanto Kagaku Company) were added followed by reflux under heating for 1 hour. The reaction solution was cooled to room temperature. Then, water (15 mL) was added to the mixture followed by extraction with ethyl acetate (3×20 mL), washing with brine (20 mL) and drying over $MgSO_4$. The solvent was evaporated. The obtained residue was purified by silica gel column chromatography (hexane:ethyl acetate=80:20) to give the title compound (130 mg). LC-MS:HPLC retention time 1.90 minutes, m/z (M+H) 488, Condition C-1.

Example 133

Methyl 2-{3,5-diphenyl-4-(trifluoromethyl)-1H-pyrazol-1-yl}thiazole-4-carboxylic acid To N,N-dimethylformamide (1.5 mL, manufactured by Kanto Kagaku Company) solution of the compound of Example 132 (130 mg), copper iodide (I) (15 mg, manufactured by Kanto Kagaku Company) and methyl 2,2-difluoro-2-(fluorosulfonyl)acetic acid (86 μL, manufactured by Wako Pure Chemical Industries, Ltd.) were added and stirred at 100° C. overnight. To the reaction solution, water (5 mL) was added followed by extraction with ethyl acetate (3×10 mL), washing with brine (10 mL) and drying over $MgSO_4$. The solvent was evaporated. The obtained residue was purified by silica gel column chromatography (hexane:ethyl acetate=80:20) to give the title compound (49.5 mg). LC-MS:HPLC retention time 1.85 minutes, m/z (M+H) 430, Condition C-1.

Example 134 to 136

Preparation of the compounds of Example Nos. 134 to 136 is described below. Detailed information regarding Example Nos. 134 to 136 is given in Table 5. Meaning of the symbols included in Table 5 is as follows.

"Exp."; Example number, "Str."; Example compound, "S. M."; Starting material for preparation of a corresponding compound.

In addition, when starting materials are the compounds described in Examples or Reference examples of the present invention, they are indicated with such Example number or Reference example number (i.e., "Exp. Example number" for Example number).

"LCMS" means data obtained from liquid chromatography mass analysis spectrum (m/z). Specifically, it consists of "method", "R. T.", and "MS" described below.

"method"; LCMS condition. Condition "A-1" corresponds to the "LCMS" apparatus and Condition (A-1) described above.

"R. T."; retention time in LCMS (unit; min).;

"MS"; mass spectrum data (both M+H and M−H are described), with the proviso that, "N.D" indicates that it was impossible to detect molecular ion peaks.

"Synth. Method"; method for preparing the corresponding compound of Example. Symbols included in "Synth. Method" column indicate the preparation methods as described below. "b" is the preparation method shown in Example 2, and compounds can be synthesized with reference to the corresponding examples.

TABLE 5

| Exp. | Str. | S.M. | Synth. Method | LC-MS method | R.T. | MS |
|---|---|---|---|---|---|---|
| 134 | | Exp 133 | b | C-1 | 1.48 | 416 (M + H) |
| 135 | | Exp 130 | b | C-1 | 1.30 | 377 (M + H) |
| 136 | | Exp 131 | b | C-1 | 1.67 | 391 (M + H) |

Test Example 1

Measurement of an Antagonist Activity by Using Cells Expressing Human EP1 Receptor In order to investigate the EP1 receptor antagonist activity of the compounds of the present invention, a reporter activity was measured by using HEK293 cells in which human EP1 receptor has been stably expressed.

(1) Measurement Method

As a result of searching Refseq Database for prostaglandin E receptor, genetic information of human EP1 (NM_000955) receptor was obtained. Based on this sequence information, human EP1 receptor gene was cloned by PCR using human cDNA as a template and by other general method to give human EP1 receptor. Then, HEK293 in which the receptor is stably expressed was established, together with a reporter gene (SRE-Luciferase) in which serum responsible element (SRE) is added at the upstream region of firefly luciferase gene. The resulting cells were added to a 96 well plate ($5 \times 10^4$ cells/well) and cultured for one day. To the plate, PGE2 (200 nM, final concentration 10 nM) and the test compound (in an amount of 1/20, 20× of the final concentration) were added to initiate the reaction. After allowing the reaction to proceed at 37° C. for 6 hours, the medium was aspirated off, added with a luminescent agent and the reporter activity was measured.

(2) Measurement Result

The compounds which had been tested were expressed as "Exp. example number" using the example number. Same expression system is used below.

The representative compounds of the present invention showed an excellent antagonist activity during the antagonist activity measurement test using the cells expressing human EP1 receptor.

According to the antagonist activity measurement test using the cells expressing human EP1 receptor, the compounds which had been tested (Test compound No.: Exp. 30, Exp. 35, Exp. 36, Exp. 37, Exp. 38, Exp. 44, Exp. 54, Exp. 80, Exp. 92, Exp. 94, Exp. 95, Exp. 105, Exp. 110, Exp. 111, Exp. 114, Exp. 116, Exp. 117) showed $IC_{50}$ value the same or less than 0.1 µM. Further, other compounds which had been also tested (Test compound Nos.: Exp. 20, Exp. 39, Exp. 48, Exp. 88, Exp. 90, Exp. 91, Exp. 128) showed $IC_{50}$ value of 0.3 to 0.1 µM, according to the antagonist activity measurement test using the cells expressing human EP1 receptor. Still further, other compounds which had been also tested (Test compound Nos.: Exp. 14, Exp. 42, Exp. 127) showed $IC_{50}$ value of 1.0 to 0.3 µM, according to the antagonist activity measurement test using the cells expressing human EP1 receptor.

Test Example 2

Measurement of an Antagonist Activity by Using Cells Expressing Human EP1 Receptor In order to investigate the EP1 receptor antagonist activity of the compounds of the present invention, intracellular $Ca^{2+}$ was measured by using HEK293 cells in which human EP1 receptor has been stably expressed.

(1) Measurement Method

Cells expressing human EP1 receptor were suspended in an assay buffer to the concentration of $5 \times 10^6$ cells/ml, added with Puronic F-127 (final concentration 0.2%), and Fura 2-AM (final concentration 5 uM), followed by incubation at 37° C. for 30 minutes. After washing twice with the assay buffer, the cells were again suspended in the assay buffer to $1 \times 10^6$ cells/60 ul, and then transferred to a 96 well UV plate ($1 \times 10^6$ cells/60 ul/well). Thereafter, by using a fluorescent chemical screening system (FDSS4000, Hamamatsu Photonics K.K.), intracellular $Ca^{2+}$ concentration was measured after adding 20 ul of each of the test compounds and PGE2 (5× of the final concentration for both). $Ca^{2+}$ concentration was measured by determining fluorescence intensity after irradiation with two excitation wavelengths, i.e., 340 and 380 nm.

Furthermore, EP1 antagonist activity was calculated as a ratio (%) of inhibiting increase in intracellular $Ca^{2+}$ concentration by PGE2 (10 nM).

Assay buffer: 20 mM HEPES/KOH (pH 7.4), 115 mM NaCl, 5.4 mM KCl, 0.8 mM $MgCl_2$, 0.8 mM $CaCl_2$, 13.8 mM D-glucose, 0.1% BSA (2) Measurement Result The representative compounds of the present invention showed an excellent antagonist activity during the intracellular $Ca^{2+}$ assay.

According to the intracellular $Ca^{2+}$ assay, the compounds which had been tested (Test compound Nos.: Exp. 35, Exp. 38, Exp. 111, Exp. 114, Exp. 116) showed $IC_{50}$ value the same or less than 0.3 µM. Further, other compounds which had been also tested (Test compound Nos.: Exp. 30, Exp. 36, Exp. 37, Exp. 94, Exp. 95) showed $IC_{50}$ value of 1.0 to 0.3 µM, according to the intracellular $Ca^{2+}$ assay. Still further, other compounds which had been also tested (Test compound Nos.: Exp. 20, Exp. 39) showed $IC_{50}$ value of 3.0 to 1.0 µM, according to the intracellular $Ca^{2+}$ assay.

Test Example 3

Receptor Binding Test Using Cells Expressing Human EP1 Receptor

Inhibitory activity of the test compounds on binding of [$^3$H]PGE2 in HEK293 cells stably expressing human EP1 receptor was measured.

(1) Measurement Method

HEK293 cells which stably express human EP1 receptor were established by using the gene for human EP1 receptor, and then a membrane fraction was prepared therefrom. Thus-prepared membrane fraction was incubated at 30° C. for 90 minutes with a reaction solution (200 µL/well) which includes the test compound and [$^3$H]PGE2. Upon the completion of the reaction, the reaction solution was aspirated off under reduced pressure, and the [$^3$H]PGE2 bound to the membrane fraction was trapped by using Unifilter Plateg F/C (manufactured by Packard) and the bound radioactivity was counted with a liquid scintillator.

Kd value was obtained from a Scatchard plot. Non-specific binding was obtained from the binding in the presence of an excess amount (10 µM) of non-labeled PGE2. For the measurement of an inhibitory activity of the test compound on [$^3$H]PGE2 binding, [$^3$H]PGE2 (1 nM) and various concentrations of the test compound were added. Meanwhile, for all of the reactions, the buffer as described below was used.

Buffer;10 mM MES/NaOH (pH 6.0), 10 mM $MgCl_2$, 1 mM EDTA, 0.1% BSA

Dissociation constant of the compounds, i.e., Ki, was obtained according to the following equation. In this regard, [C] indicates the concentration of [$^3$H]PGE2 that was used for binding inhibition test (1 nM for the present test).

$$Ki = IC50/(1+[C]/Kd)$$

(2) Measurement Result

The representative compounds of the present invention showed an excellent activity during the [$^3$H]PGE2 binding inhibition test.

According to the [$^3$H]PGE2 binding inhibition test, the compounds which had been tested (Test compound Nos.: Exp. 30, Exp. 35) showed Ki value the same or less than 0.3 µM.

Test Example 4

Activity of Relaxing Rat Bladder Smooth Muscle

An activity of relaxing rat bladder smooth muscle can be determined with reference to the method established by Maggi, et al. (Eur. J. Pharmacol. 152, p. 273-279 (1988)). Specifically, a smooth muscle specimen is prepared from a bladder isolated from a male SD rat, and isometric contracting power is measured in an organ bath. After the contraction with $3\times10^{-7}$M PGE2, the compound to be tested is dissolved in DMSO and added to the organ bath with final concentration of $10^{-8}$M to $10^{-5}$M. As a result, a relaxing activity of the compound can be determined.

Test Example 5

Micturition Interval Prolongation in an Anesthetized Rat-I
Activity of prolonging micturition interval in an anesthetized rat can be determined with reference to the method established by Maggi, et al. (Eur. J. Pharmacol. 145, p. 105-112 (1988)). Specifically, a female SD rat is anesthetized with urethane and fixed in a flat position, and a catheter is inserted through an external urethral opening. Using a three-way stop cock, it is connected to a pressure transducer and a syringe pump. While infusing physiological saline including 100 µM PGE2 to the bladder at constant rate, cystometrogram is recorded. After confirming stabilized micturition interval, micturition threshold pressure and maximal voiding pressure, a solvent or the compound to be tested is administered to the left femoral vein so that an activity of prolonging micturition interval can be determined as an efficacy of the drug compound.

Test Example 6

Micturition Interval Prolongation in an Anesthetized Rat-II
Activity of prolonging micturition interval in an anesthetized rat was determined with reference to the method established by Maggi, et al. (Eur. J. Pharmacol. 145, p. 105-112 (1988)). Specifically, a female SD rat was anesthetized with urethane and fixed in a flat position, and a catheter was inserted through an external urethral opening. Using a three-way stop cock, it was connected to a pressure transducer and a syringe pump. While infusing physiological saline including 0.2% acetic acid to the bladder at constant rate, cystometrogram was recorded. After confirming stabilized micturition interval, micturition threshold pressure and maximal voiding pressure, a solvent or the compound to be tested was administered to the left femoral vein and an activity of prolonging micturition interval was determined as an efficacy of the drug compound. Each group included five animals. As a result, it was found that the representative compounds of the present invention have an excellent efficacy of prolonging micturition interval. Results are summarized in Table 5.

TABLE 6

| Test compound No. | Micturition interval prolonging activity |
|---|---|
| Exp. 30 | 25.8% |

Test Example 7

Micturition Interval Prolonging Activity in an Awaken Rat
Micturition interval prolonging activity in an awaken rat can be determined with reference to the method established by Shinozaki et al. (Biomed. Res. 26(1), p. 29-33 (2005)). Specifically, a rat bladder was exposed under anesthetization using halothane. To the vertex region of the bladder a catheter was inserted while the other end was taken out from the abdominal cavity and connected to a pressure transducer and an infusion pump. A catheter is also inserted to a jugular vein of the animal. The rat was put into a restraining cage and after awakened from the anesthetization, physiological saline was infused to the bladder via the bladder catheter and cystometrogram (herein below, abbreviated as "CMG") was recorded. Two to three hours later, the bladder infusion solution was replaced with physiological saline including 0.2% acetic acid and CMG recording was further carried out. One to two hours after the replacement of the infusion solution, a solvent or the compound to be tested was administered to the jugular vein and an activity of prolonging micturition interval by administration of acetic acid was determined as an efficacy of the drug compound.

Test Example 8

Micturition Frequency Measurement in a Rat (Awaken State)
Micturition frequency of a rat can be measured with reference to the method by Oka et al. (Jpn. J. Pharmacol. 87, p. 27-33 (2001)). Specifically, a rat is placed in a metabolic cage and discharged urine is continuously collected and weighed. Each different weight of urine can be regarded as micturition frequency and also difference in total weight can be regarded as total weight of discharged urine. In this regard, it was known, for example, that frequent micturition can be caused by intraperitoneal administration of cyclophosphamide (Lecci et al., Br. J. Pharmacol. 130, p. 331-338 (2000)), spinal cord injury (Kamo et al., Am. J. Physiol. Renal Physiol. 287, p. F434-F441 (2004)) or cerebral infarction by ligation of middle cerebral artery (Yokoyama et al., J. Urol., 174, p. 2032-2036 (2005)). To the frequent micturition model established accordingly, a solvent or a test compound is orally administered and a therapeutic effect of the compound can be determined in view of the decreased micturition frequency.

Test Example 9

Therapeutic Effect on Symptoms of Bladder Irritation and Overactive Bladder Caused by Bladder Outlet Obstruction
Bladder outlet obstruction (BOO) model can be established with reference to the method of Malmgren et al. (J. Urol. 137, p. 1291-1294 (1987)). After six weeks, the bladder of a BOO model rat is exposed under anesthetization. To the vertex region of the bladder a catheter was inserted while the other end was taken out from the backside of a cervical region. A catheter is also inserted to a jugular vein. Two days later, the rat is placed in a restraining cage, and physiological saline was infused via the bladder catheter and cystometrogram was recorded. A solvent or the test compound is intravenously infused and reduced number of non-voiding contraction (NVC) having almost no micturition is determined as an efficacy of the drug compound.

Test Example 10

By using a frequent micturition rat model in which frequent micturition is induced by infusion of prostaglandin E2 to a bladder (Takeda et al., Neurourol. Urodyn. 21, p. 558-565 (2002)), or infusion of ATP to a bladder (Atiemo et al. Urology 65, p. 622-626 (2005)), a therapeutic effect of a drug compound can be determined by following an increase in micturition frequency or an increase in infusion amount (bladder volume) in accordance with intravenous administration of a test compound during cystometry measurement. In addition, by following a decrease in micturition frequency after administering a test compound during the test for measuring micturition frequency, a therapeutic effect of a drug compound can be determined.

Test Example 11

Evaluation of an analgesic activity in a sciatic nerve ligation model (Bennett model).
Analgesic activity in a sciatic nerve ligation rat model (Bennett model) can be determined with reference to the method of Kawahara et al. (Anesth. Analg. 93, p. 1012-1017 (2001)).

[Model Establishment]

A male SD rat (200 to 250 g, Charles River Corporation, Japan) was anesthetized with sodium pentobarbital (50 mg/kg, i. p.), and being laid on its stomach, an incision is made right above the right femur. From the center femur region, biceps femoris is cut off and a sciatic nerve is exposed (about 5 mm) while being careful not to damage it. Using 4-0 braid silk thread (Nescosuture), in the center femur region, ligation is made at four positions at 1 mm interval from the peripheral side. For the ligation, neither surgical knot nor square knot is made. Only a single knot is made and the knot is gradually tightened to the level at which the hind leg can be slightly moved. Then, the muscular membrane and the skin are sewn. For a sham operation group, procedures are taken until the exposure of sciatic nerve and then muscular membrane and the skin are sewn.

[Measurement Method for Heat Irritation Test]

Measurement is carried out by using BASILE Planter Test (UGO BASILE 7370). To a right hind leg of an unconstrained rat, intrusive heat irritation is applied and a time spent until the escape behavior is made (response latency) is measured. Specifically, a rat is placed in a box for measurement and adapted for about 5 minutes. Next, a movable I.R. (infrared) generator is placed under a glass plate and I.R. irradiation is adjusted to be focused on the inside of six balls close to the sole of right foot of the rat. It is important to confirm that a close contact is made between the glass plate and hind foot. Subsequently, after starting heat irritation, response latency for the escape behavior, i.e., flinching of the leg, is measured. When escape behavior occurs, the switch is automatically turned off and the response time is counted.

[Measurement Method for Pressure Irritation Test]

Measurement is carried out by using an analgesy meter for pressure irritation test (UGO BASILE 7200). Specifically, the right leg of a rat is placed between a supporting board and a pressurizing needle and pressure is applied at constant rate of 16 g/s. When the rat feels pain and draws its leg responding to the pain, a pedal switch is stopped and the measurement value is recorded.

[Evaluation Schedule]

First, heat irritation test and pressure irritation test are performed before an operation. Seven days after the operation, a solvent or the test compound is administered once via an oral, an intravenous, an intraperitoneal or a subcutaneous route. 1, 2 and 24 hours after the administration, the same procedure is carried out. For the continuous oral administration group, a solvent or the test compound is administered one day after the operation, once a day for seven days. 1, 2 and 24 hours after the $7^{th}$-day administration, the heat irritation test and pressure irritation test are carried out.

Test Example 12

Evaluation of Analgesic Activity in a Freund's Complete Adjuvant Rat Model

An analgesic activity in a Freund's complete adjuvant rat model can be investigated with reference to the method of Giblin et al. (Bioorg. Med. Chem. Lett. 17, p. 385-389 (2007)).

[Model Establishment]

A male SD rat (150 to 200 g, Charles River Corporation, Japan) was anesthetized with sodium pentobarbital (50 mg/kg, i. p.). Inactivated tuberculosis bacteria (M. TUBERCULOSIS DES. H37 RA, DIFCO Laboratories) which is suspended in fluid paraffin (10.0 mg/mL concentration) is injected to the sole of left hind foot of the rat (0.05 mL volume).

[Measurement Method for Pain Stimulation Test]

Measurement is carried out by using Von Frey type apparatus for pain test (UGO BASILE 37400). A rat is placed a plastic cage with wire bottom and maintained in an unconstrained state. For adaptation, the rat is placed to the cage at least 20 minutes before the test. A filament which provides pressure irritation is adjusted to be focused on the inside of six balls close to the sole of left foot of the rat. A constant amount of pressure irritation is vertically applied. It is determined whether or not the rat exhibits an escape behavior responding to the pressure irritation. Thereafter, threshold value for the escape behavior is obtained.

[Evaluation Schedule]

First, one day before establishing a model, the pain stimulation test is carried out. In addition, having the model establishment day as Day 0, the pain stimulation test is carried out on Day 1, 3, 7, 9, 11, and 13. On Day 13 after model establishment, a solvent or the test compound is administered once via an oral, an intravenous, an intraperitoneal or a subcutaneous route and then the pain stimulation test is carried out until two hours after the administration. In case of a continuous administration, from Day 13 of the model establishment, a solvent or the test compound is administered twice per day for five days via an oral, an intravenous, an intraperitoneal or a subcutaneous route (administration frequency and administration period are not limited to these). From Day 14 after the model establishment, a pain stimulation test is carried out every day before the administration of a solvent or the test compound and it is continued 24 hours after the day of the termination of the administration.

Test Example 13

Evaluation of an Analgesic Activity in a Rat Model of Postoperative Pain

An analgesic activity in a rat model of postoperative pain can be determined in view of the method presented by Omote et al. (Anesth Analg. 92, p. 233-8 (2001)).

[Model Establishment]

A male SD rat (250 to 300 g, SLC Corporation, Japan) was anesthetized with 3% isofluran. To avoid any infection, the sole of right hind foot was sterilized with povidone iodine and penicillin-G (30,000U, Benzylpenicillin; Sigma-Aldrich Company) was injected intramuscularly to the triceps. Skin and fascia are cut from the region which is 0.5 cm apart from the heel to the tip of paw of a right hind limb of the rat (i.e., 1 cm long). After the incision, the skin and fascia are sewn together by using 5-0 nylon thread and the rat is put into a cage for recovery.

[Measurement Method for Pain Stimulation Test]

Measurement is carried out by using Von Frey type apparatus for pain test (UGO BASILE 37400). A rat is placed a plastic cage with wire bottom and maintained in an unconstrained state. For adaptation, the rat is placed to the cage at least 20 minutes before the test. A filament which provides pressure irritation is adjusted to be focused on the inside of six balls close to the sole of left foot of the rat. A constant amount of pressure irritation is vertically applied. It is then determined whether or not the rat exhibits an escape behavior responding to the pressure irritation. Thereafter, threshold value for the escape behavior is obtained.

[Administration of a Solvent and a Test Compound]

A rat is anesthetized with 1.5% isofluran. To the sole of the animal which received an operation, a solvent or the test compound is injected while being careful to avoid any leakage. Two and twenty-four hours after the operation, the solvent or the test compound is administered twice, respectively.

[Evaluation Schedule]

First, before the operation, the pain stimulation test is carried out to give a control value. Two and twenty-four hours after the operation but before the administration, the pain stimulation test was carried out and significant reduction in threshold value compared to the control value as a baseline is confirmed. Then, 15, 30, 45, 60, 90 or 120 minutes after each administration, the pain stimulation test is carried out and an analgesic effect of the test compound compared to the baseline value is obtained.

Test Example 14

Micturition Interval Prolongation in an Awaken Rat-II As a test animal, a male SD rat (Charles River Corporation, Japan) was used. The rat was anesthetized by isofluran inhalation (nitrous oxide:oxygen=7:3), and being laid on its stomach, it remained anesthetized by 2% isofluran inhalation. Then, an incision was made at the center region of the abdomen, and the bladder was exposed. A small incision was made to the vertex region of the bladder, and a polyethylene tube (PE-50: Becton Dickinson) was inserted to the bladder and fixed. One end of a cannula was subcutaneously directed to the backside of the animal, and after fixing the cannula to the abdomen wall, the incision was sealed. The cannula directed to the backside was connected to a seibel and the middle region was protected with a stainless spring. At the same time, a cannula which is used for jugular administration was inserted, directed subcutaneously to the backside and also protected by a spring. Two days after the operation, via the cannula placed inside the bladder, 0.3% acetic acid was injected to the bladder at the rate of 4.0 mL/hr to induce cystitis. Then, through one end of the tube that had been inserted to the bladder, physiological saline warmed to 37° C. was injected at the rate of 3.0 mL/hr using a three-way stop cock, while the other end was connected to a pressure transducer and cystometrogram was recorded continuously with pressure amplification. The discharged urine was collected in a vessel placed on a digital balance and change in the urine weight was measured at the same time. After confirming a stabilized micturition pattern, intravenous administration was carried out via the cannula placed in the jugular vein. Measurement was made for 60 minutes. Average value of the measurements for 30 minutes before the administration was taken as the pre-administration value, while average value of the measurements for 60 minutes right after the administration was taken as the post-administration value. Three animals were tested. As a result, it was found that the representative compound of the present invention, for example Example 35, showed at least 30% prolongation in micturition interval and increase in micturition volume.

The invention claimed is:
1. A compound represented by the formula (1) or a salt thereof:

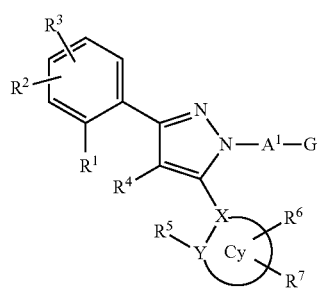

(1)

in the formula (1), Cy represents an aryl group, a saturated cyclic hydrocarbon group or a saturated heterocyclic group, X represents a carbon atom or a nitrogen atom, Y represents a carbon atom, a nitrogen atom, an oxygen atom, or a sulfur atom, $R^1$, $R^2$ and $R^3$ can be the same or different from each other, and each independently represents a hydrogen atom, a halogen atom, an alkyl group which may be substituted, an alkenyl group which may be substituted, an alkynyl group which may be substituted, an aryl group which may be substituted, an aralkyl group which may be substituted, a hydroxy group, an alkoxy group which may be substituted, an aryloxy group which may be substituted, an alkylthio group, an acyl group, an acyloxy group, an alkylsulfinyl group, an alkylsulfonyl group, an alkyl carbamyl group, —$N(R^{P1})(R^{P2})$ (where $R^{P1}$ and $R^{P2}$ can be the same or different from each other, and each independently represents a hydrogen atom, an alkyl group which may be substituted, or an aryl group an aryl group which may be substituted, or $R^{P1}$ and $R^{P2}$ together form a 3- to 7-membered ring to represent a cyclic amine of $N(R^{P1})(R^{P2})$), an acylamino group, an acyl(alkyl)amino group, an alkylsulfonylamino group, an alkylsulfonyl(alkyl)amino group, a carboxy group, —$CON(R^{P3})(R^{P4})$ (where $R^{P3}$ and $R^{P4}$ can be the same or different from each other, and each independently represents a hydrogen atom, an alkyl group which may be substituted, or an aryl group which may be substituted, or $R^{P3}$ and $R^{P4}$ together form a 3- to 7-membered ring to represent a cyclic amine of $N(R^{P3})(R^{P4})$) or —$COOR^{P5}$ (where $R^{P5}$ represents an alkyl group which may be substituted), $R^4$ represents a hydrogen atom, a halogen atom, an alkyl group which may be substituted, an alkenyl group which may be substituted, an alkynyl group which may be substituted, a hydroxy group, an alkoxy group which may be substituted, or —$N(R^{41})(R^{42})$ (where $R^{41}$ and $R^{42}$ can be the same or different from each other, and each independently represents a hydrogen atom, an alkyl group which may be substituted, or an aryl group which may be substituted, or $R^{41}$ and $R^{42}$ together form a 3- to 7-membered ring to represent a cyclic amine of $N(R^{41})(R^{42})$), $R^5$, $R^6$, and $R^7$ can be the same or different from each other, and all or part of them may be present, or none of them may be present (with the proviso that, when Y represents an oxygen atom or a sulfur atom, $R^5$ is not present), and when $R^5$, $R^6$, and $R^7$ are present, each independently represents a hydrogen atom, a halogen atom, an alkyl group which may be substituted, an alkenyl group which may be substituted, an alkynyl group which may be substituted, an aryl group which may be substituted, an aralkyl group which may be substituted, a hydroxy group, an alkoxy group which may be substituted, an aryloxy group which may be substituted, an alkylthio group, an acyl group, an acyloxy group, an alkylsulfinyl group, an alkylsulfonyl group, an alkyl carbamyl group, —$N(R^{Y1})(R^{Y2})$ (where $R^{Y1}$ and $R^{Y2}$ can be the same or different from each other, and each independently represents a hydrogen atom, an alkyl group which may be substituted, or an aryl group which may be substituted, or $R^{Y1}$ and $R^{Y2}$ together form a 3- to 7-membered ring to represent a cyclic amine of $N(R^{Y1})(R^{Y2})$), an acylamino group, an acyl(alkyl)amino group, an alkylsulfonylamino group, an alkylsulfonyl(alkyl)amino group, a carboxy group, —$CON(R^{Y3})(R^{Y4})$ (where $R^{Y3}$ and $R^{Y4}$ can be the same or different from each other, and each independently represents a hydrogen atom, an alkyl group which may be substituted, or an aryl group which may be substituted, or $R^{Y3}$ and $R^{Y4}$ together form a 3- to 7-membered ring to represent a cyclic amine of $N(R^{Y3})(R^{Y4})$) or —$COOR^{Y5}$ (where $R^{Y5}$ represents an alkyl group which may be substituted), or, $R^1$ and $R^4$ may together represent a ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom, or a nitrogen atom, or, $R^4$ and $R^5$ may together represent a ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom, or a nitrogen atom, $A^1$ represents a single bond, an alkylene group which may be substituted or an alkenylene group which may be substituted, G represents any one of the following formulas ($G^1$) to ($G^4$):

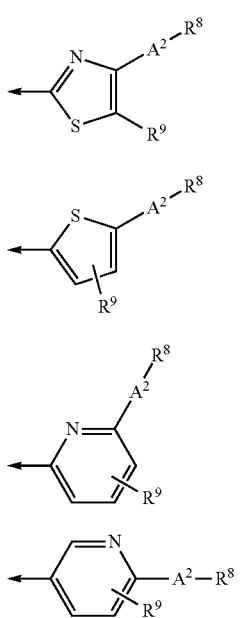

in the formulas ($G^1$) to ($G^4$), $A^2$ represents a single bond, an alkylene group, or an alkenylene group which may be substituted, $R^8$ represents a carboxy group, —$CON(R^{81})(R^{82})$ (where $R^{81}$ and $R^{82}$ can be the same or different from each other, and each independently represents a hydrogen atom, an alkyl group which may be substituted, or an aryl group which may be substituted, or $R^{81}$ and $R^{82}$ together form a 3- to 7-membered ring to represent a cyclic amine of $N(R^{81})(R^{82})$), —$COOR^{83}$ (where $R^{83}$ represents an alkyl group which may be substituted) or a tetrazol-5-yl group, and $R^9$ represents a hydrogen atom or an alkyl group which may be substituted.

2. The compound according to claim 1 or the salt thereof in which G is the formula ($G^1$).

3. The compound according to claim 1 or the salt thereof in which $R^8$ is a carboxy group.

4. The compound according to claim 1 or the salt thereof in which $A^2$ is a single bond.

5. The compound according to claim 1 or the salt thereof in which $A^1$ is a single bond, an alkylene group, or an alkenylene group.

6. The compound according to claim 1 or the salt thereof in which $A^1$ is a single bond.

7. The compound according to claim 1 or the salt thereof in which $A^1$ is a methylene group which may be substituted with a lower alkyl group.

8. The compound according to claim 1 or the salt thereof in which Cy is an aryl group.

9. The compound according to claim 1 or the salt thereof in which Cy is a phenyl group.

10. The compound according to claim 1 or the salt thereof in which Cy is a saturated heterocyclic group.

11. The compound according to claim 1 or the salt thereof in which $R^4$ is a halogen atom, an alkyl group which may be substituted, a hydroxy group, or an amino group.

12. The compound according to claim 1 or the salt thereof in which $R^1$, $R^2$, and $R^3$ are a group which is independently selected from a group consisting of a hydrogen atom, a halogen atom, an alkyl group which may be substituted, a hydroxy group, and an alkoxy group which may be substituted.

13. The compound according to claim 1 or the salt thereof in which $R^5$, $R^6$, and $R^7$ are a group which is independently selected from a group consisting of a hydrogen atom, a halogen atom, an alkyl group which may be substituted, a hydroxy group, and an alkoxy group which may be substituted.

14. The compound according to 1 or the salt thereof in which $R^5$, $R^6$, and $R^7$ are a group which is independently selected from a group consisting of a hydrogen atom, a halogen atom, an alkyl group which may be substituted, and an alkoxy group which may be substituted.

15. The compound according to claim 1 or the salt thereof in which $R^1$ and $R^4$ together represent a ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom, or a nitrogen atom.

16. The compound according to claim 1 or the salt thereof in which $R^4$ and $R^5$ together represent a ring which is selected from a group consisting of a partially unsaturated hydrocarbon ring which may be substituted and an unsaturated hydrocarbon ring which may be substituted, or a ring in which one of the ring-constituting carbon atoms in the ring is substituted with an oxygen atom, a sulfur atom, or a nitrogen atom.

17. The compound according to claim 1 or the salt thereof, which is represented by any of formula (1-1) to (1-5):

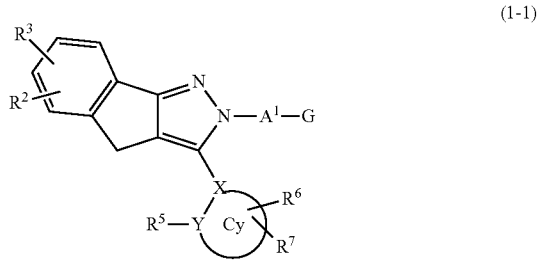

-continued
(1-2)
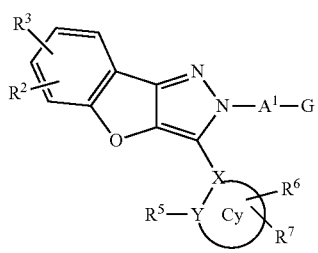
(1-3)
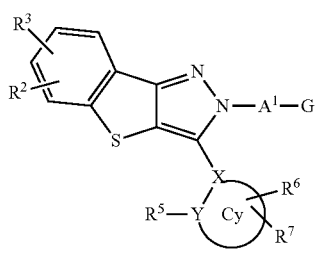
(1-4)
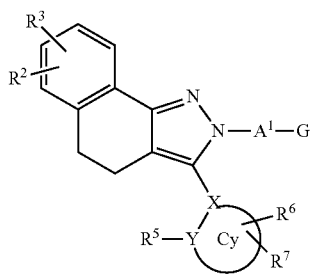
(1-5)
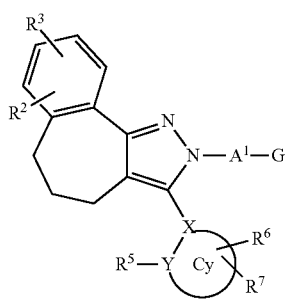
wherein Cy, X, Y, $R^2$, $R^3$, $R^5$, $R^6$, $R^7$, $A^1$ and G are as defined in claim 1.
18. The compound according to claim 1 or the salt thereof, which is represented by any of formula (1-6) to (1-10):
(1-6)
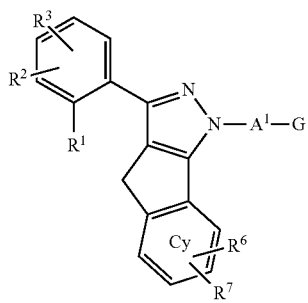
-continued
(1-7)
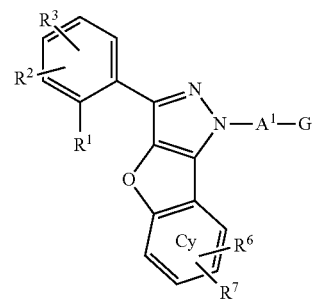
(1-8)
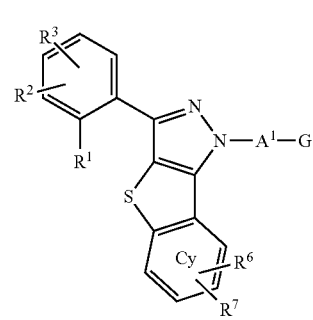
(1-9)
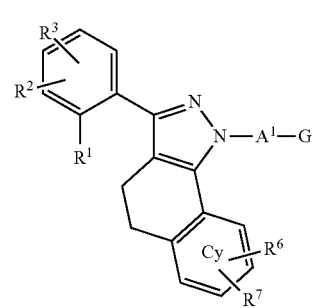
(1-10)
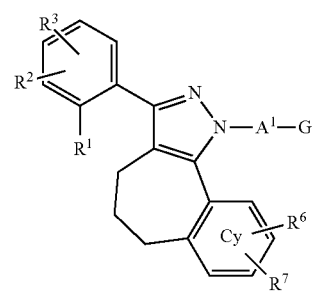
wherein Cy, $R^1$, $R^2$, $R^3$, $R^6$, $R^7$, $A^1$ and G are as defined in claim 1.
19. A compound selected from the group consisting of:
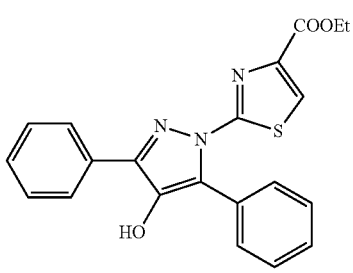

-continued
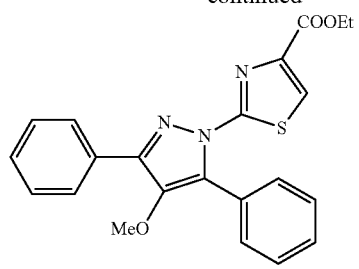
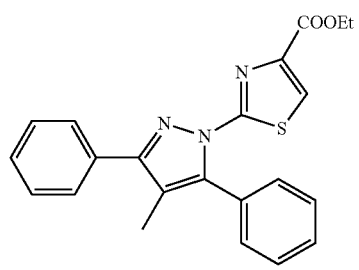
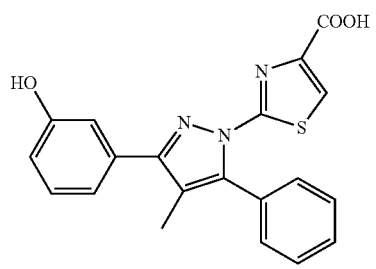
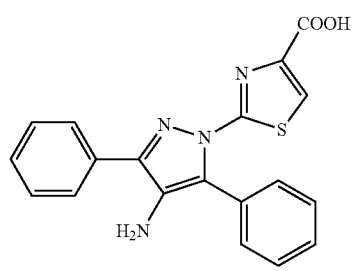
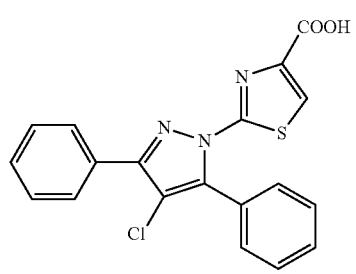
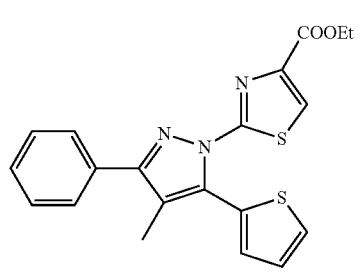
-continued
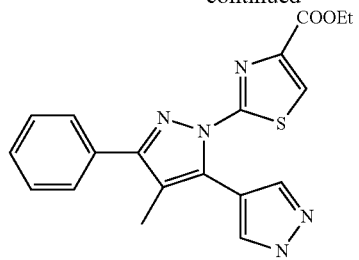
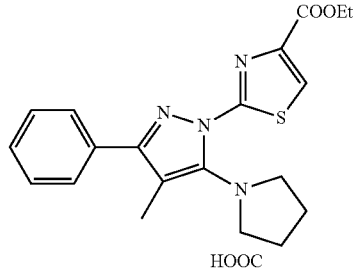
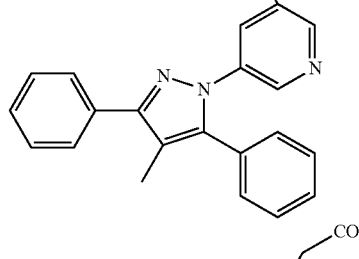
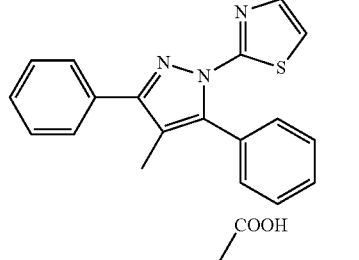
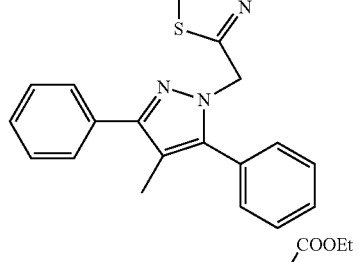
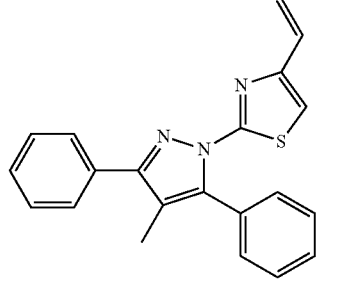

159
-continued
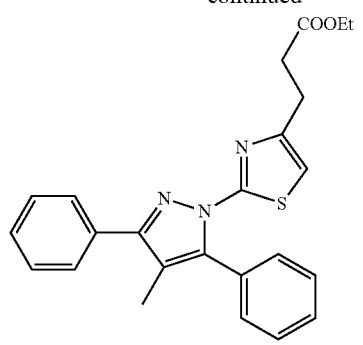
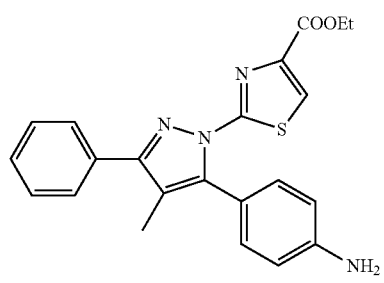
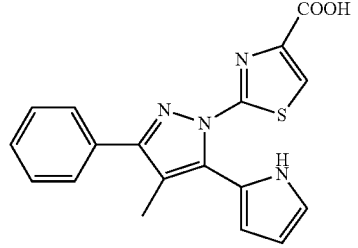
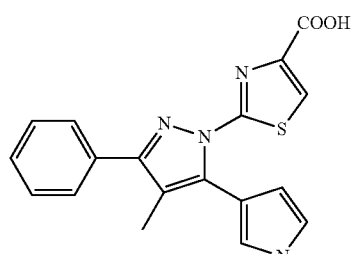
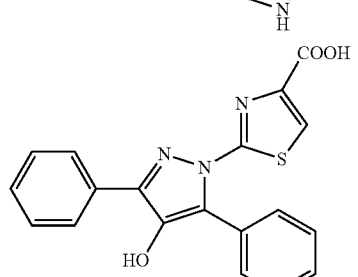
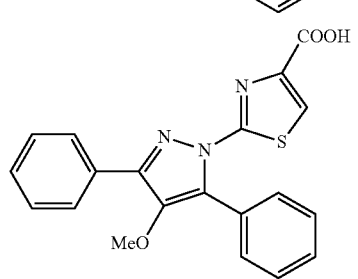
160
-continued
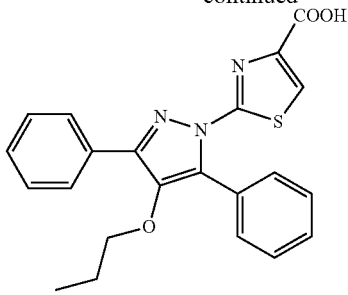
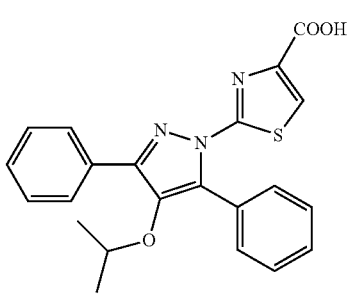
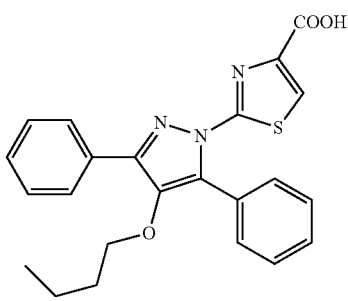
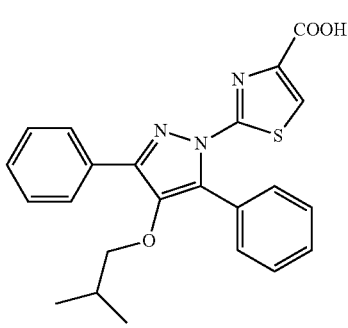
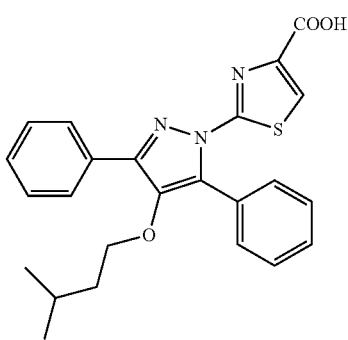

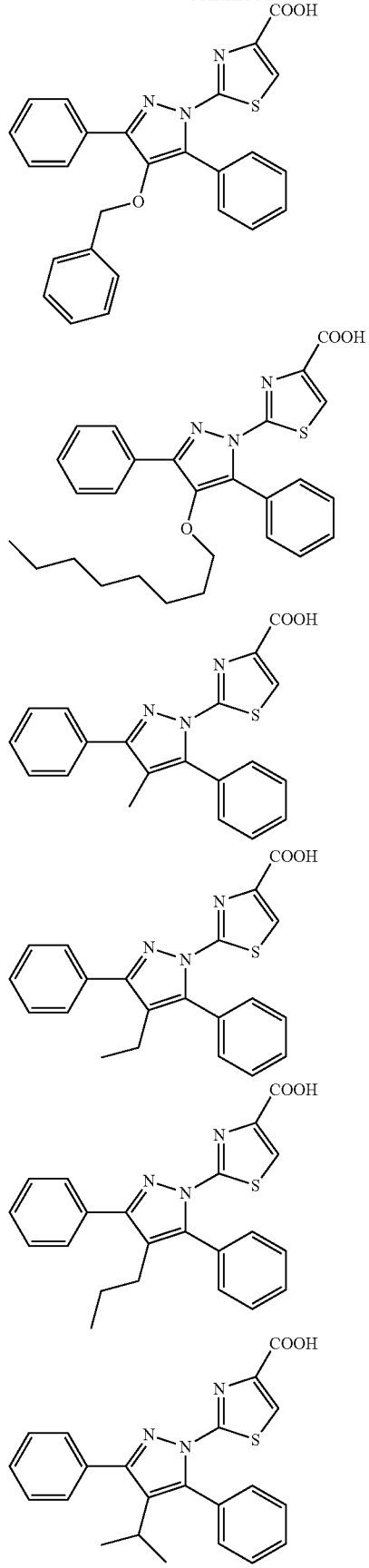
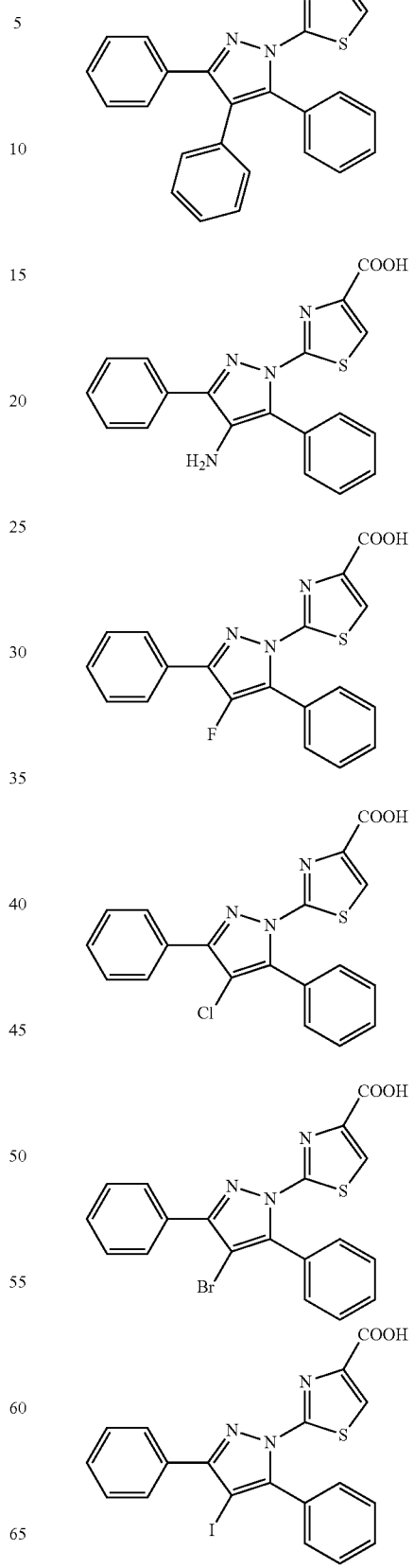

163 164
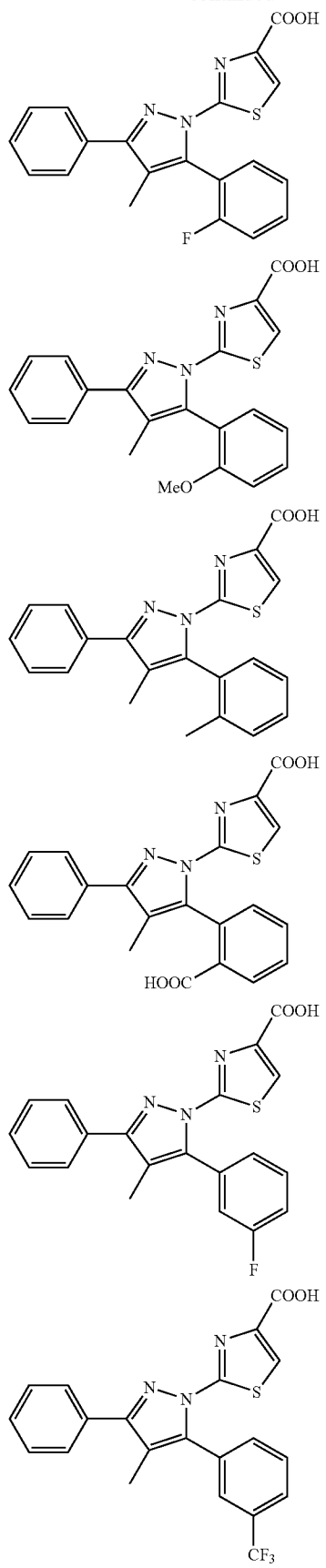
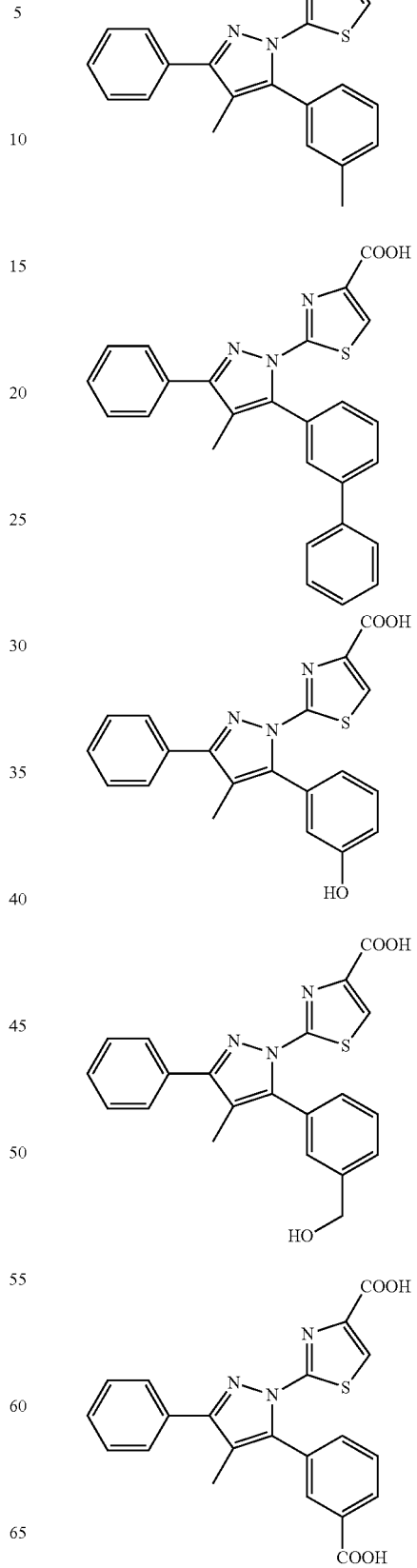

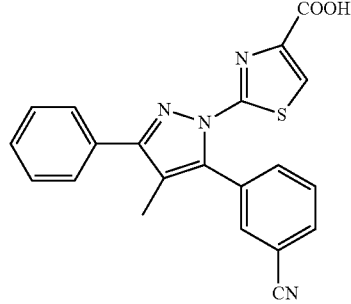
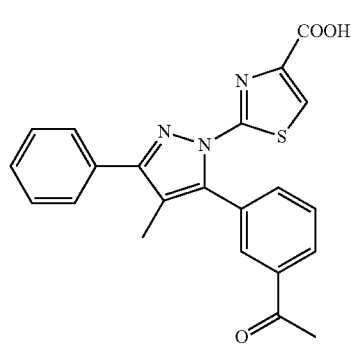
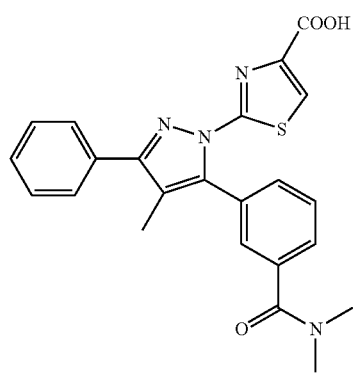
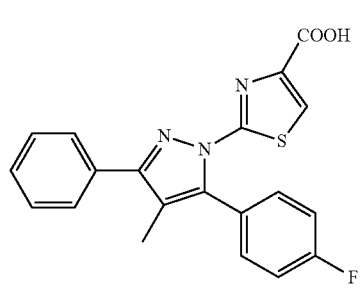
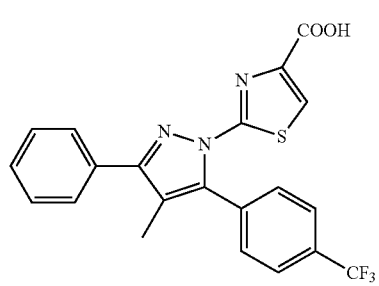
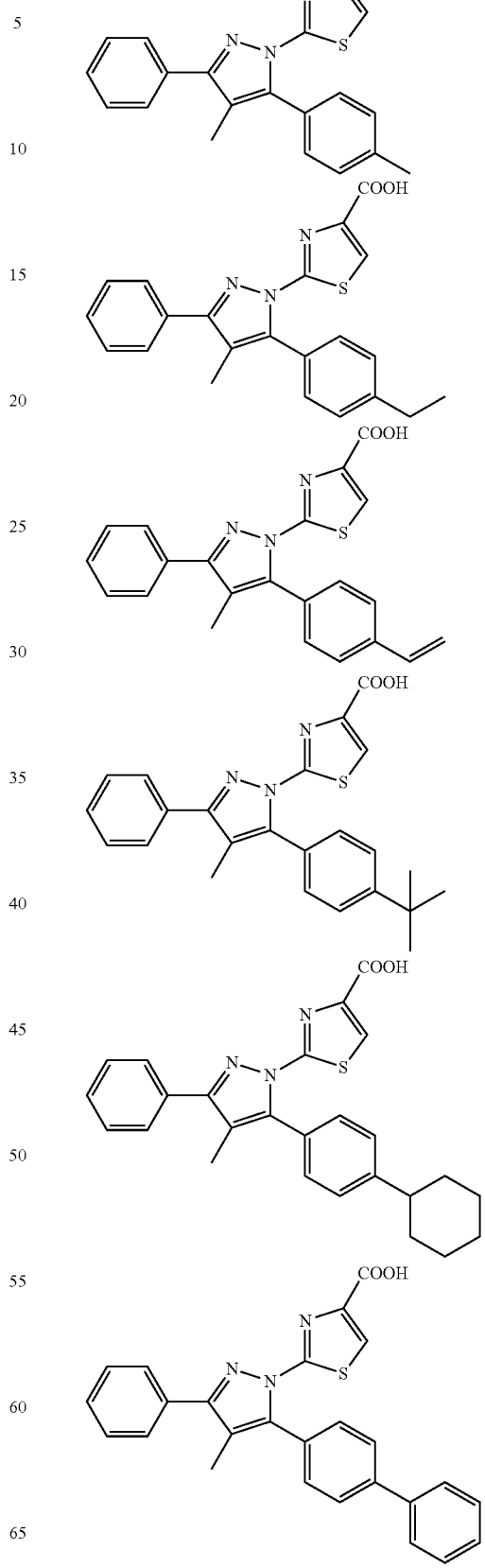

167
-continued
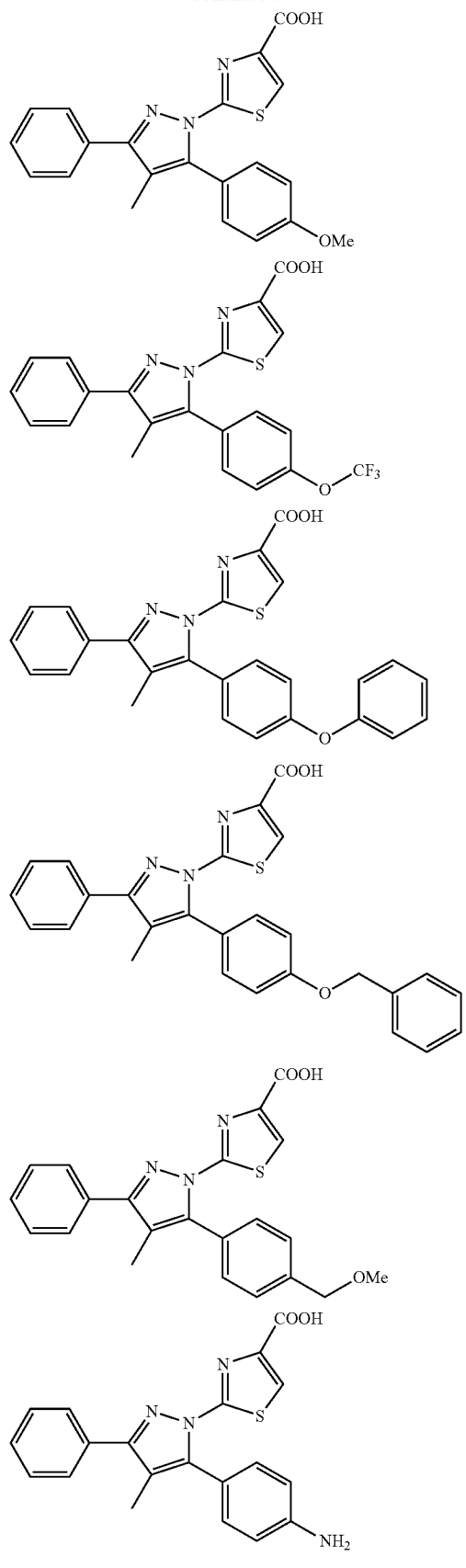
168
-continued
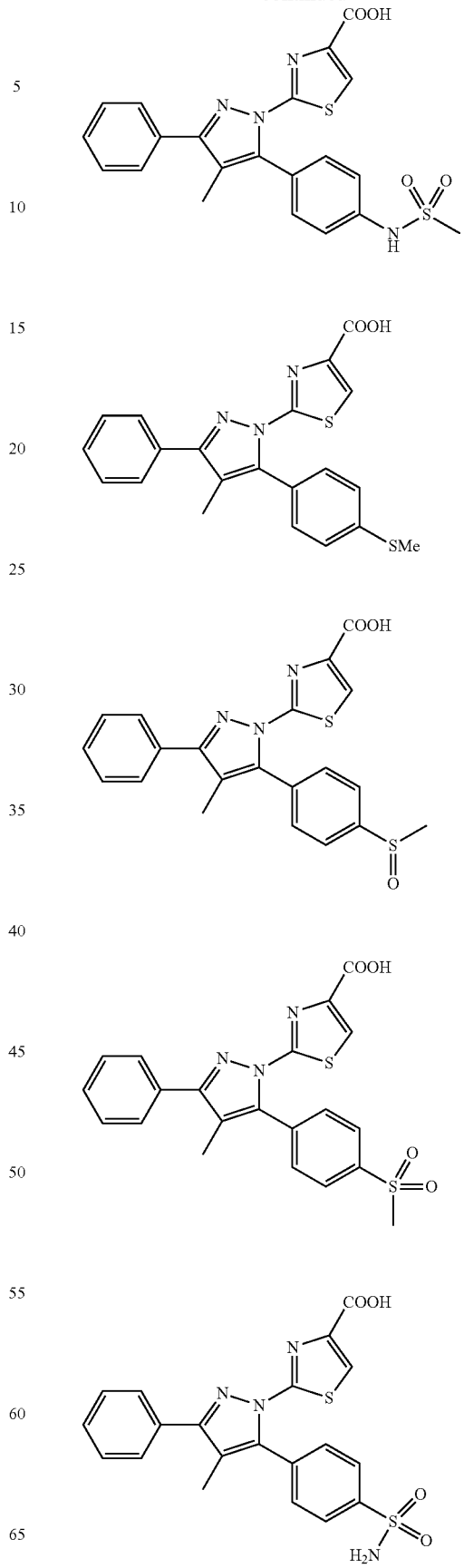

-continued
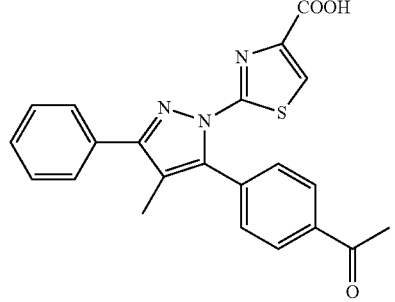
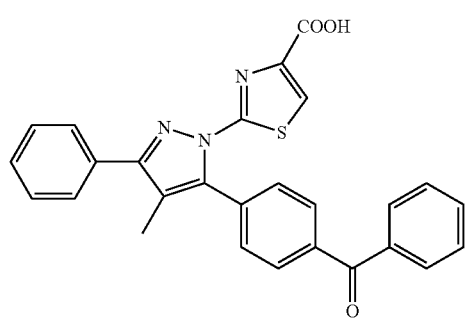
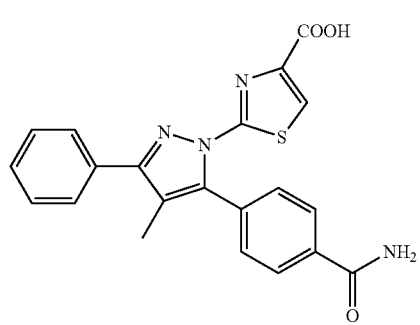
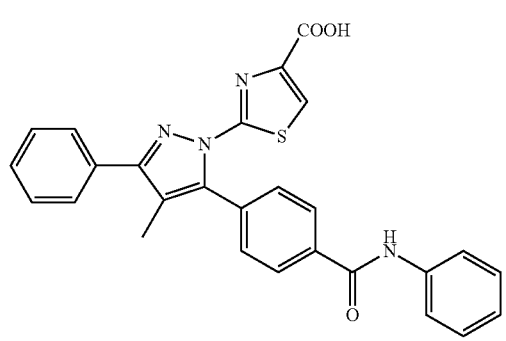
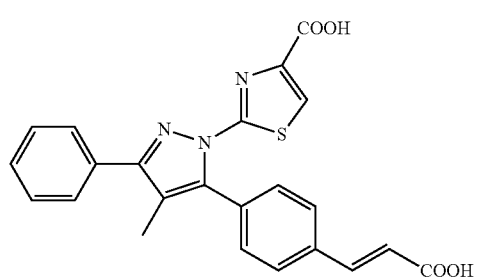
-continued
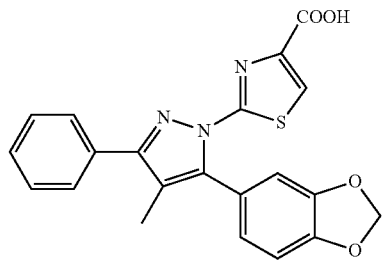
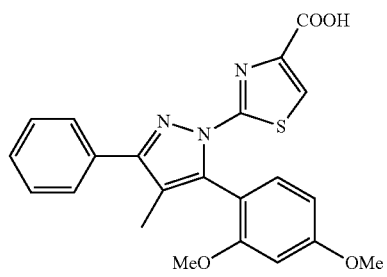
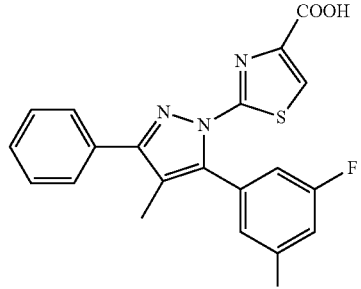
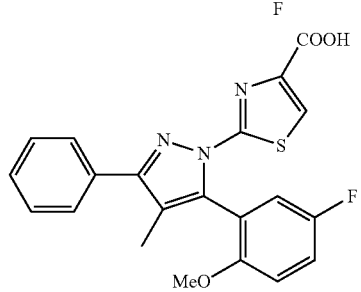
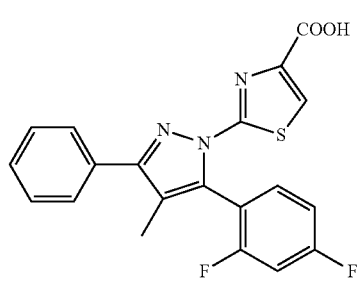
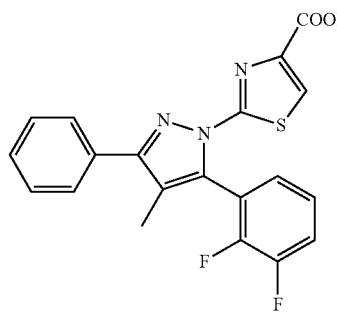

171
-continued
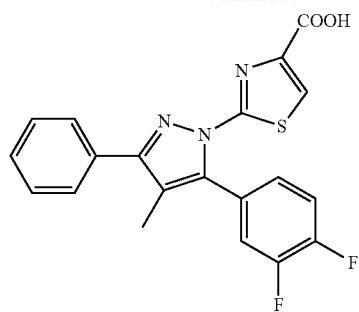
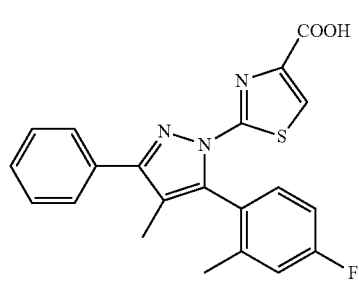
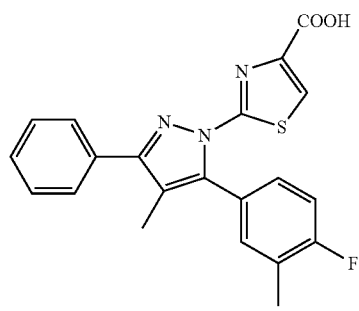
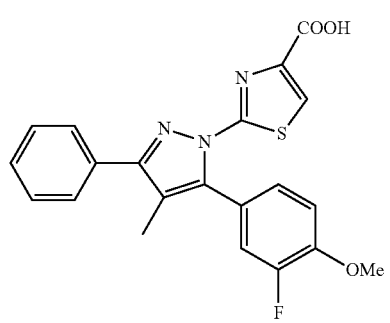
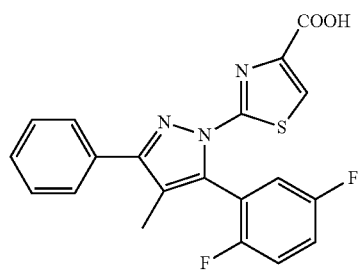
172
-continued
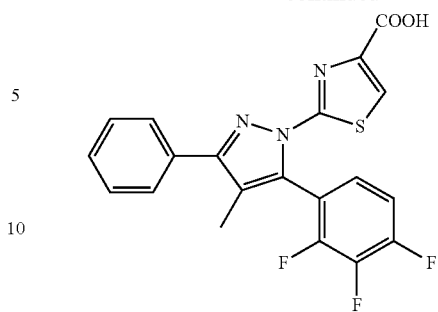
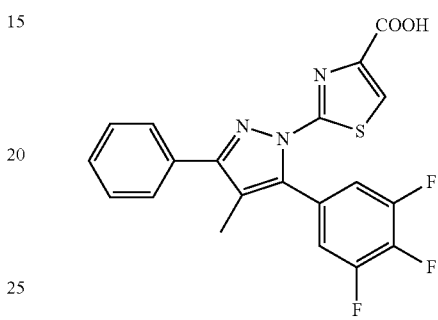
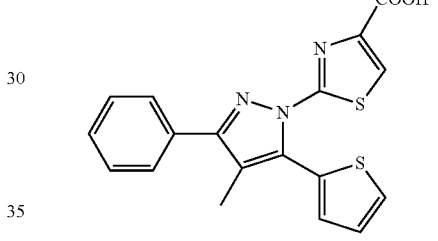
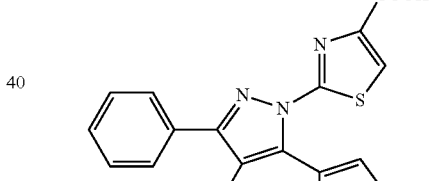
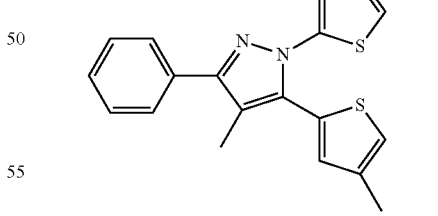
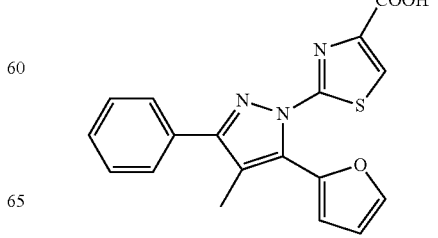

173
-continued
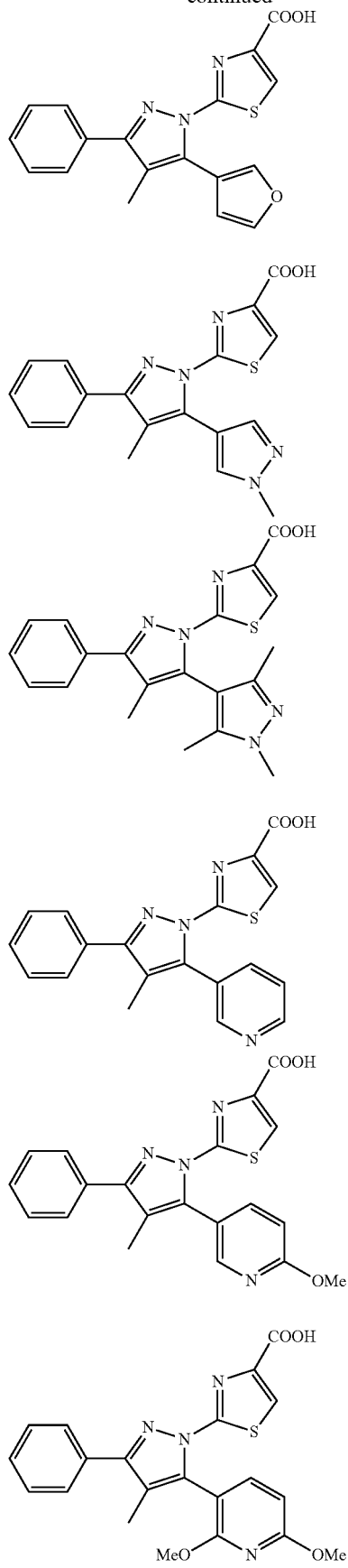
174
-continued
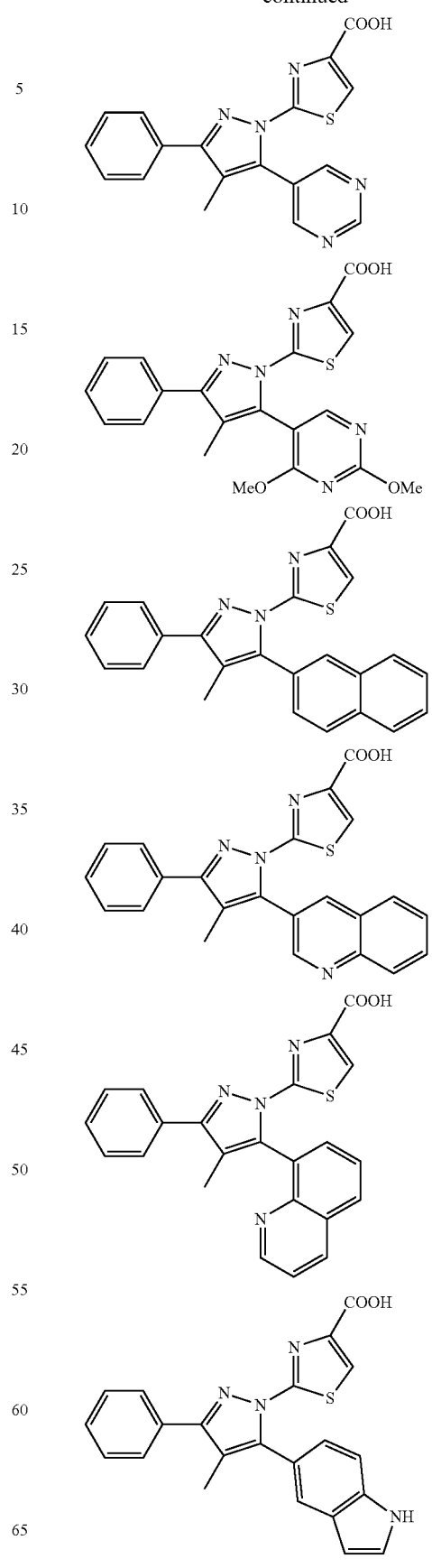

175
-continued
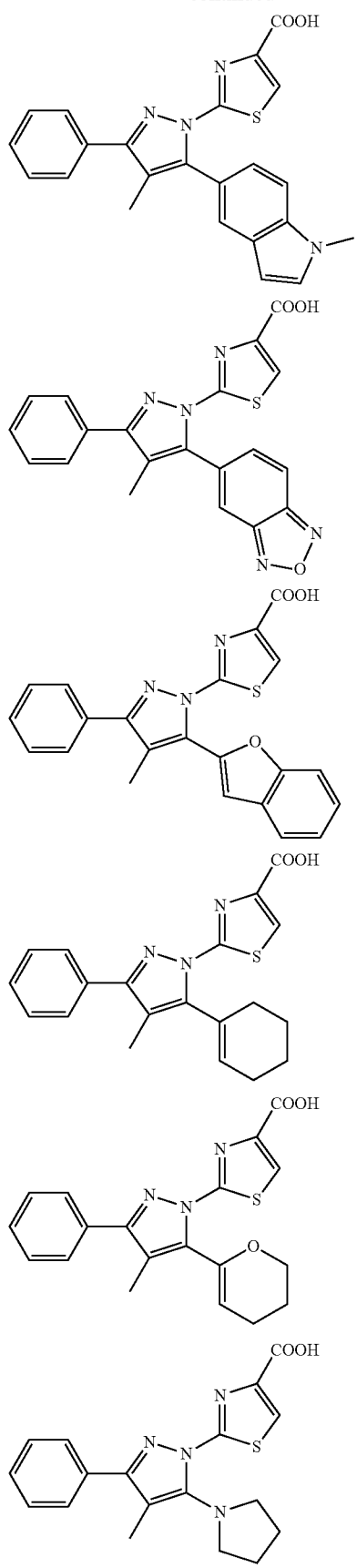
176
-continued
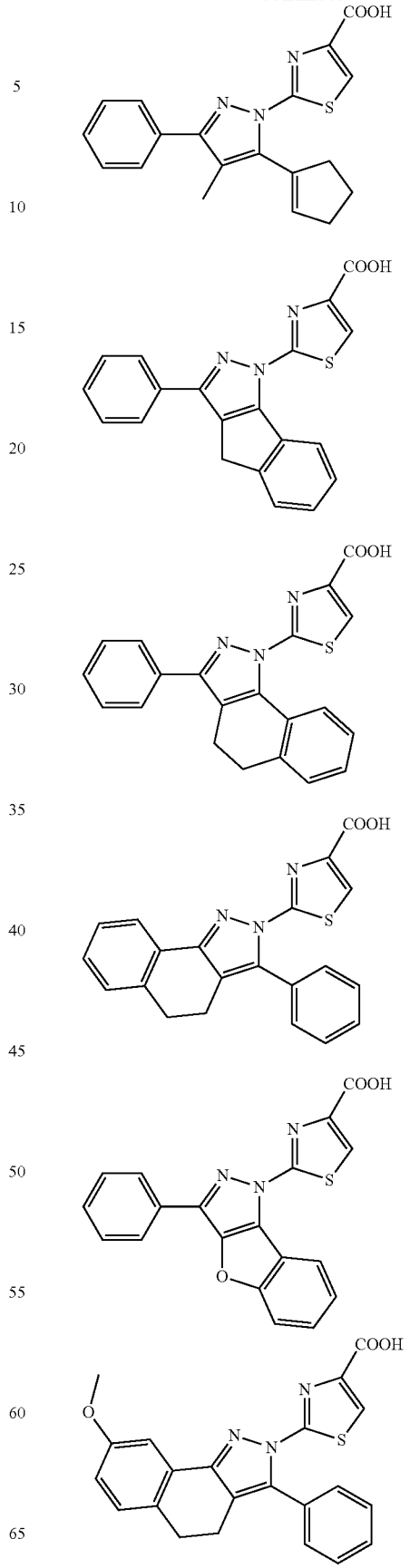

177
-continued
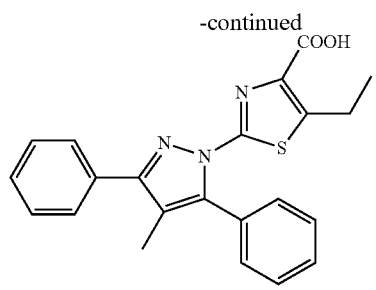
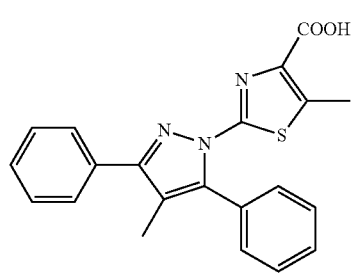
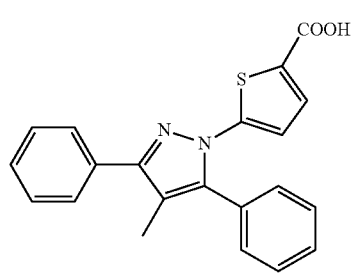
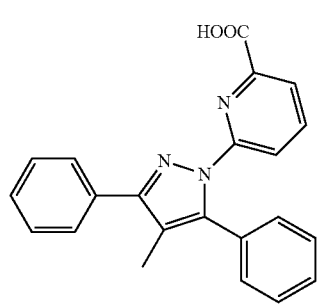
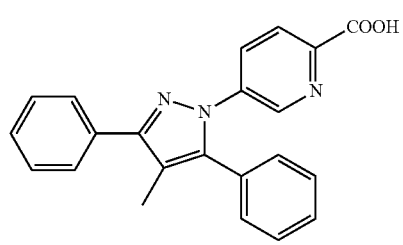
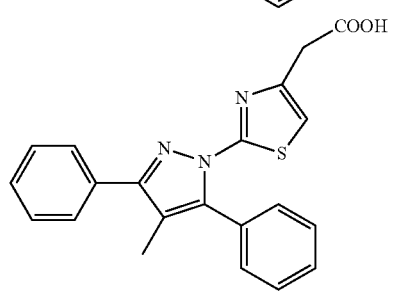
178
-continued
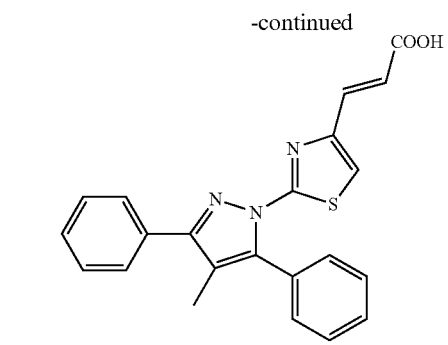
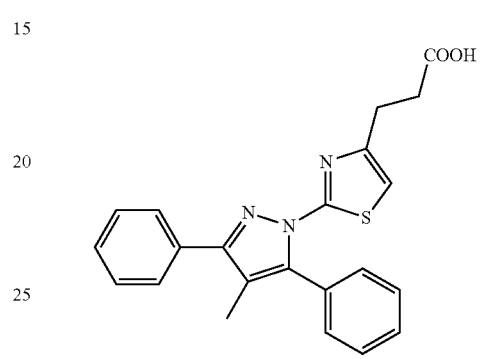
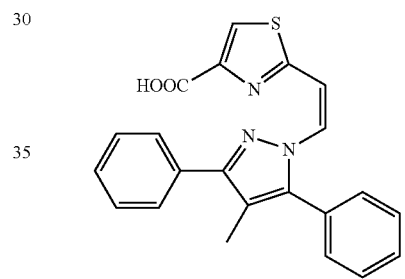
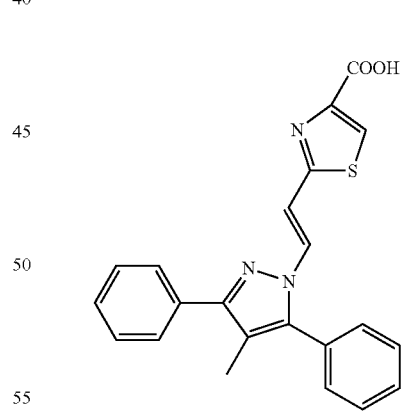
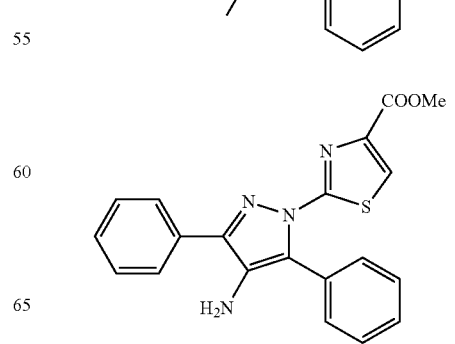

-continued
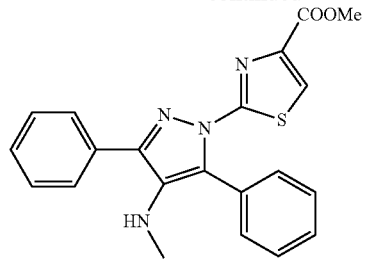
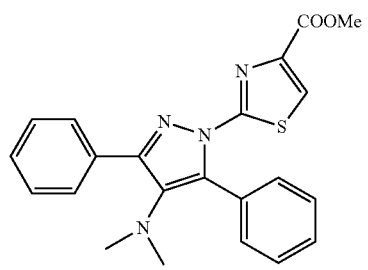
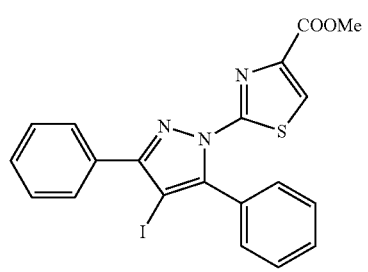
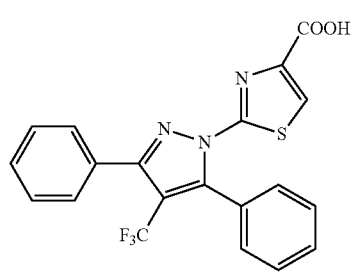
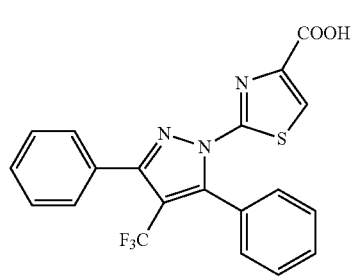
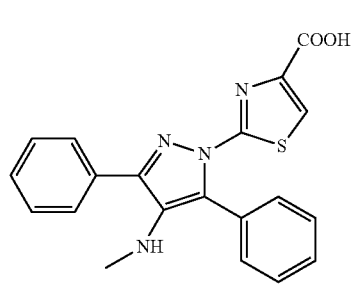
-continued
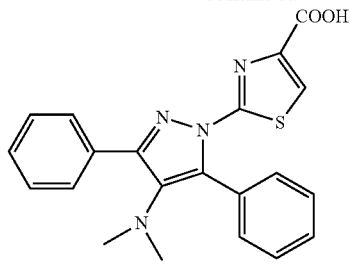
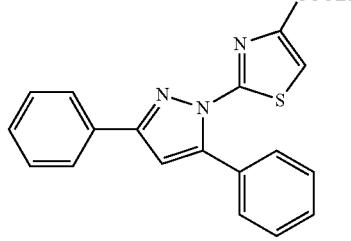
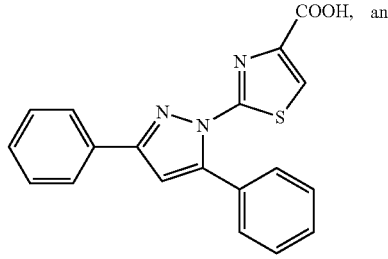
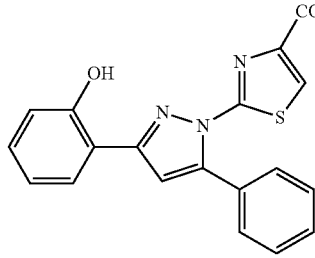
or a salt thereof.
20. A compound selected from the group consisting of:
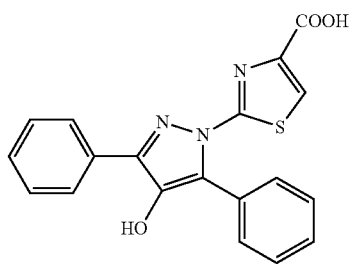
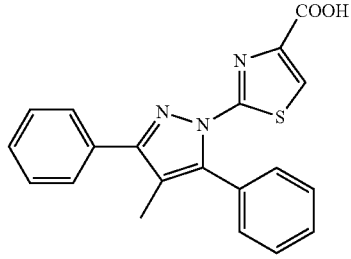

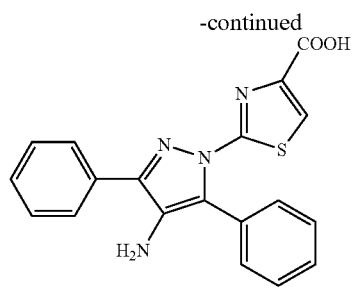
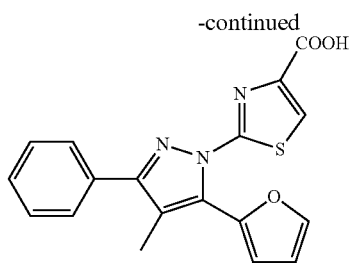
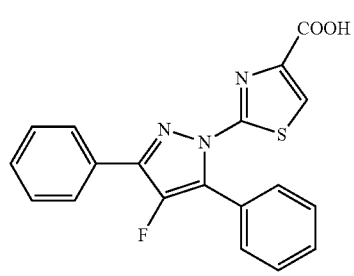
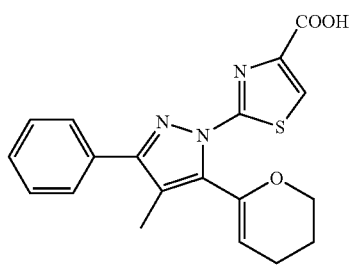
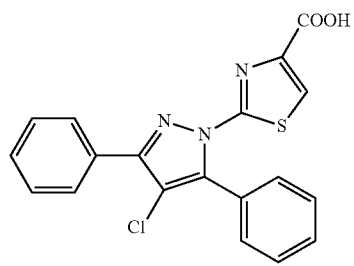
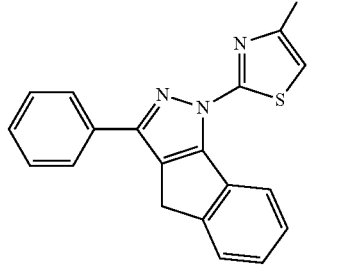
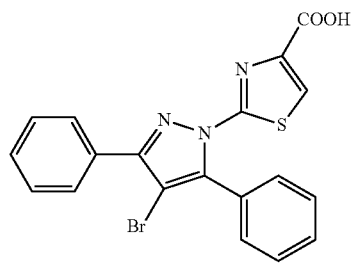
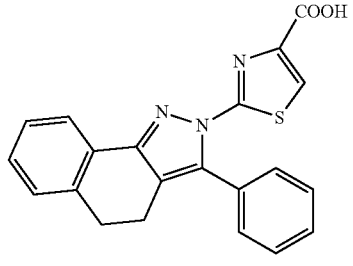
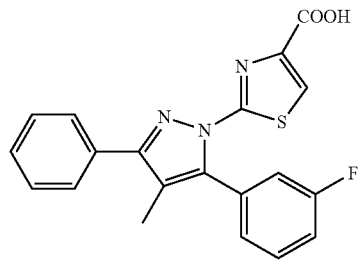
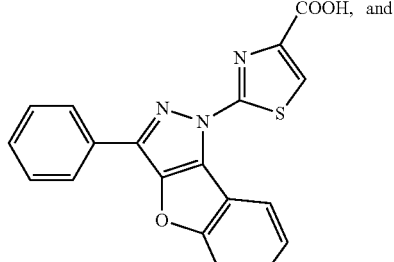
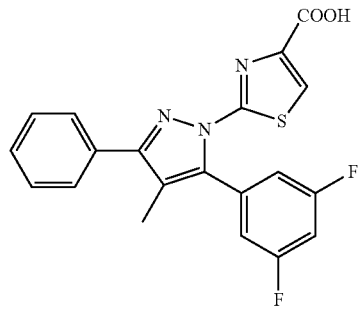
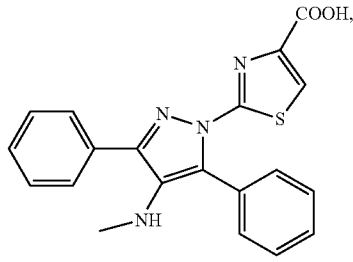
or a salt thereof.

21. A compound selected from the group consisting of:

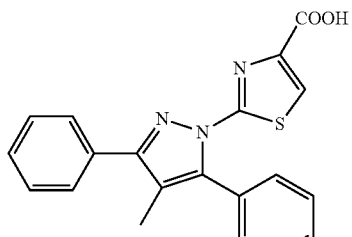

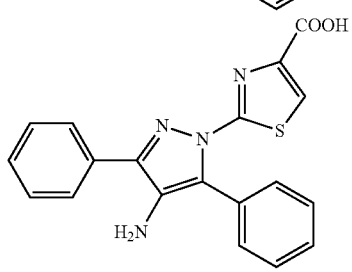

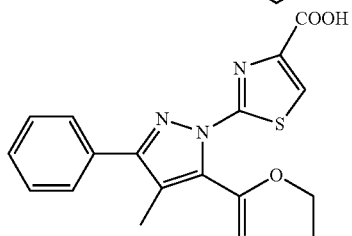

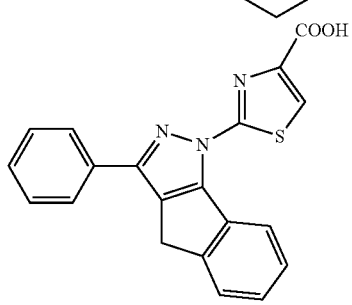

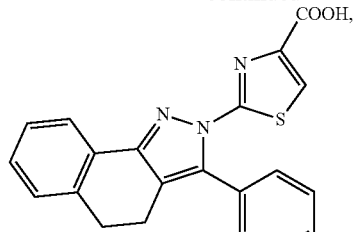

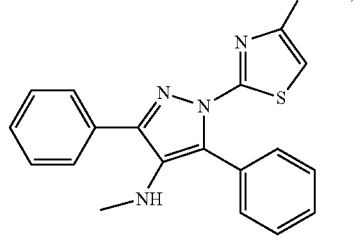

or a salt thereof.

22. A pharmaceutical composition comprising the compound according to any one of claim 1-16 or 17-21, or a pharmaceutically acceptable salt thereof, and at least one pharmacologically acceptable carrier.

23. The pharmaceutical composition according to claim 22, which is formulated for treatment of overactive bladder.

24. The pharmaceutical composition according to claim 22, formulated as an EP1 antagonist composition.

25. A method of making a pharmaceutical composition for treatment of overactive bladder comprising formulating the compound according to any one of claim 1-16 or 17-21 or a pharmaceutically acceptable salt thereof, with at least one pharmacologically acceptable carrier.

26. A method for the treatment of overactive bladder in a mammal, comprising administering to the mammal the compound according to any one of claim 1-16 or 17-21, or a pharmaceutically acceptable salt thereof, in an amount effective for the treatment of overactive bladder.

* * * * *